United States Patent
Tahari et al.

(10) Patent No.: US 10,131,673 B2
(45) Date of Patent: Nov. 20, 2018

(54) PIPERIDINE SUBSTITUTED TRICYCLIC PYRAZOLO[1,5-A]PYRIMIDINE DERIVATIVES WITH INHIBITORY ACTIVITY ON THE REPLICATION OF THE RESPIRATORY SYNCYTIAL VIRUS (RSV)

(71) Applicant: JANSSEN SCIENCES IRELAND UC, Little Island, Co Cork (IE)

(72) Inventors: Abdellah Tahari, Beerse (BE); Sandrine Marie Helene Vendeville, Beerse (BE); Tim Hugo Maria Jonckers, Beerse (BE); Pierre Jean-Marie Bernard Raboisson, Beerse (BE); Samuël Dominique Demin, Beerse (BE); Lili Hu, Beerse (BE)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

(21) Appl. No.: 15/534,458

(22) PCT Filed: Dec. 7, 2015

(86) PCT No.: PCT/EP2015/078796
§ 371 (c)(1),
(2) Date: Jun. 8, 2017

(87) PCT Pub. No.: WO2016/091791
PCT Pub. Date: Jun. 16, 2016

(65) Prior Publication Data
US 2017/0349602 A1    Dec. 7, 2017

(30) Foreign Application Priority Data

Dec. 8, 2014    (EP) .................... 14196789

(51) Int. Cl.
| C07D 487/04 | (2006.01) |
| C07D 487/14 | (2006.01) |
| C07D 491/147 | (2006.01) |
| C07D 471/14 | (2006.01) |
| C07D 401/04 | (2006.01) |
| C07D 401/14 | (2006.01) |
| A61K 31/519 | (2006.01) |
| A61P 31/14 | (2006.01) |
| A61K 31/5377 | (2006.01) |

(52) U.S. Cl.
CPC ........ *C07D 491/147* (2013.01); *A61K 31/519* (2013.01); *A61K 31/5377* (2013.01); *A61P 31/14* (2018.01); *C07D 401/04* (2013.01); *C07D 401/14* (2013.01); *C07D 471/14* (2013.01); *C07D 487/04* (2013.01); *C07D 487/14* (2013.01)

(58) Field of Classification Search
CPC .. C07D 487/04; C07D 487/14; C07D 401/04; C07D 401/14; C07D 471/14; C07D 49/147; A61K 31/519; A61P 31/14

USPC ............... 544/281, 117; 514/231.5, 259.1
See application file for complete search history.

(56) References Cited

U.S. PATENT DOCUMENTS

| 8,486,938 B2 * | 7/2013 | Babaoglu | C07D 487/04 514/233.2 |
| 8,946,238 B2 * | 2/2015 | Boojamra | A61K 45/06 514/259.3 |
| 8,980,878 B2 * | 3/2015 | Siegel | C07D 487/04 514/210.2 |
| 2017/0349591 A1 | 12/2017 | Tahari et al. | |

FOREIGN PATENT DOCUMENTS

| WO | 2011163518 A1 | 12/2011 |
| WO | 2013096681 A1 | 6/2013 |
| WO | 2013158776 A1 | 10/2013 |

OTHER PUBLICATIONS

Greene, et al., "Protective Groups in Organic Synthesis", Protective Groups in Organic Synthesis, 1981, i-xiii, 1.

(Continued)

*Primary Examiner* — Venkataraman Balasubramanian

(57) ABSTRACT

The invention concerns novel substituted tricyclic pyrazolo pyrimidine compounds of formula (I-a) or (I-b) having antiviral activity, in particular, having an inhibitory activity on the replication of the respiratory syncytial virus (RSV). The invention further concerns the preparation of such novel compounds, compositions comprising these compounds, and the compounds for use in the treatment of respiratory syncytial virus infection.

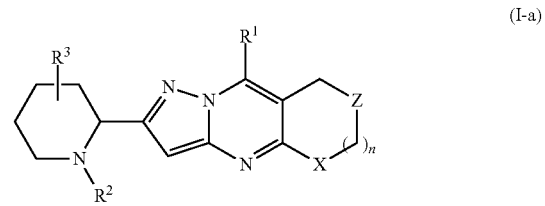

(I-a)

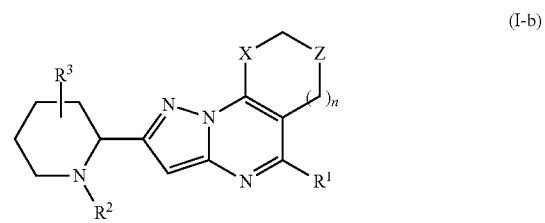

(I-b)

17 Claims, No Drawings

(56) References Cited

OTHER PUBLICATIONS

Figure 1:
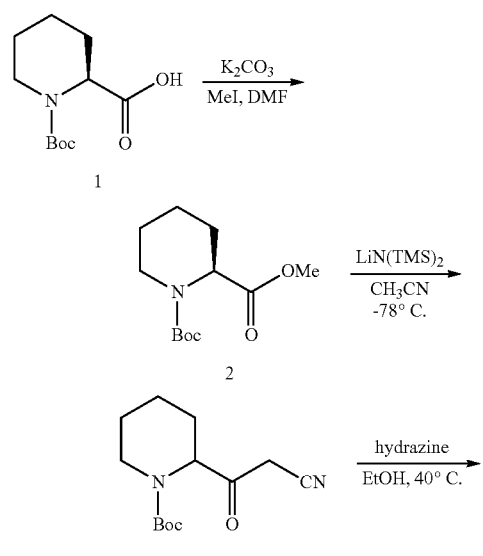
Figure 1:
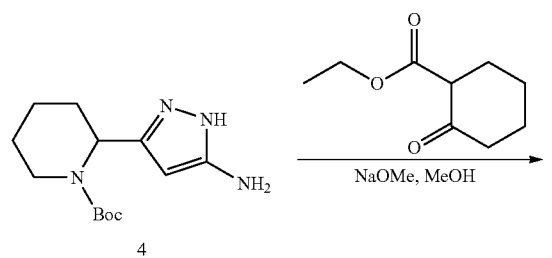
Figure 1:
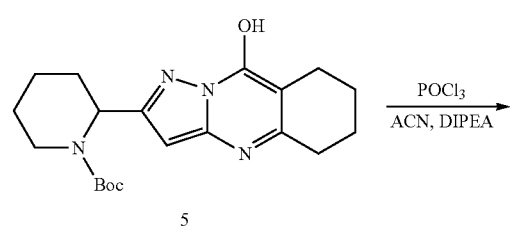
Figure 1:
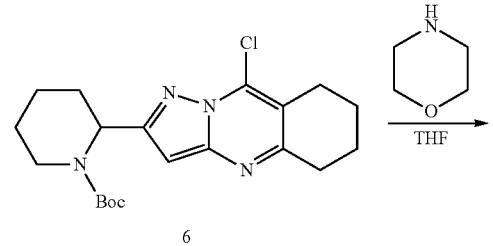
Figure 1:
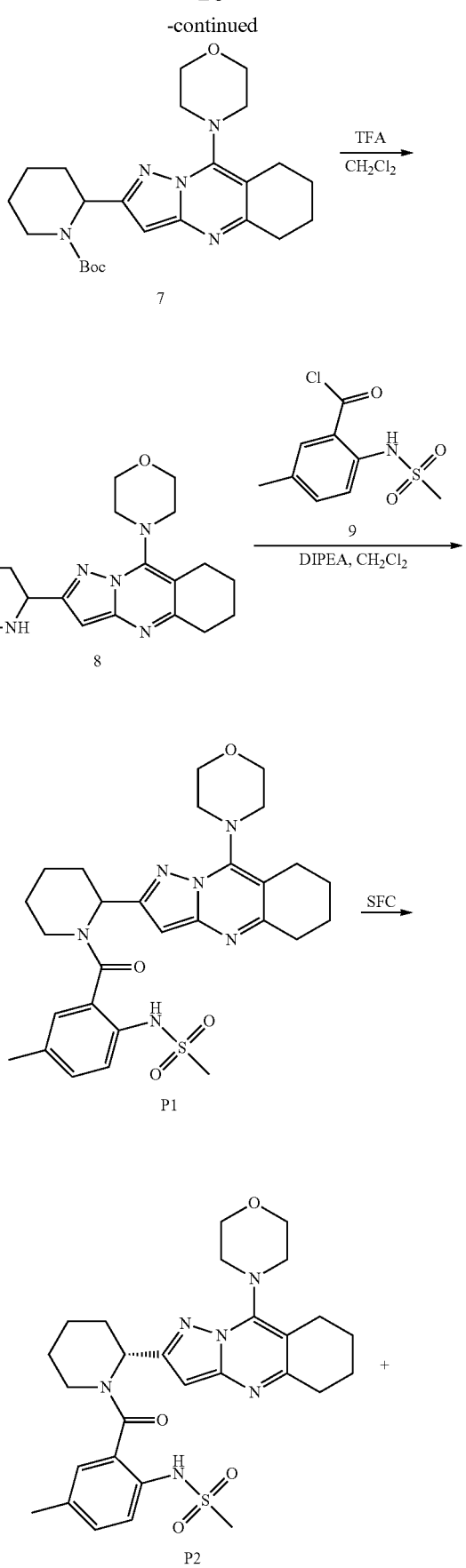

Hallack, et al., "Glycosaminoglycan Sulfation Requirements for Respiratory Syncytial Virus Infection", Journal of Virology, vol. 74(22):pp. 10508-10513 (Nov. 2000).
Hyde, et al., "CL387626 exhibits marked and unusual antiviral activity against respiratory syncytial virus in tissue culture and in cotton rats", Antiviral Research, vol. 38: pp. 31-42 (1998).
International Search Report and Written Opinion Corresponding to PCT/EP2015/078796 dated Jan. 28, 2016.

* cited by examiner

PIPERIDINE SUBSTITUTED TRICYCLIC PYRAZOLO[1,5-A]PYRIMIDINE DERIVATIVES WITH INHIBITORY ACTIVITY ON THE REPLICATION OF THE RESPIRATORY SYNCYTIAL VIRUS (RSV)

CROSS-REFERENCE TO RELATED APPLICATIONS

This application is a national phase entry of International Application No. PCT/EP2015/078796, filed on Dec. 7, 2015, which claims priority to EP Patent Application No. 14196789.3, filed on Dec. 8, 2014, each of which is incorporated herein in its entirety.

FIELD OF THE INVENTION

The invention concerns novel substituted tricyclic pyrazolo pyrimidine compounds having antiviral activity, in particular, having an inhibitory activity on the replication of the respiratory syncytial virus (RSV). The invention further concerns the preparation of such novel compounds, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

Compounds that exhibit anti-RSV activity are disclosed in WO-2011/163518, WO-2013/096681 and WO-2013/158776.

SUMMARY OF THE INVENTION

The present invention relates to compounds of formula (I-a) and formula (I-b), including any stereochemically isomeric form thereof, wherein

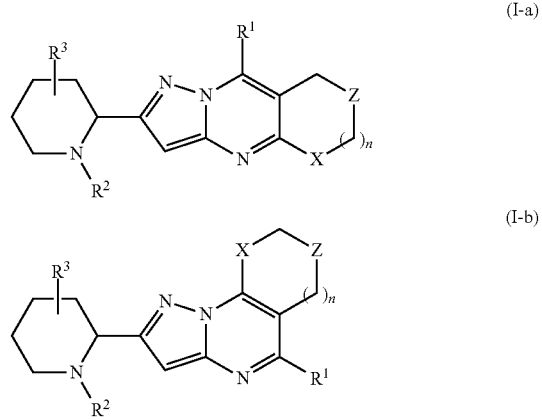

n is an integer 0, 1 or 2;
X is $CH_2$, O, $CH_2O$ or $NR^4$, wherein $R^4$ is hydrogen, $C_{1-4}$alkyl or benzyl;
Z is $CH_2$, O or $NR^4$, wherein $R^4$ is hydrogen, $C_{1-4}$alkyl or benzyl;
and at least one of X or Z is $CH_2$;
$R^1$ is hydrogen, hydroxy, $C_{1-4}$alkyl, amino, mono- or di($C_{1-4}$alkyl)amino, or Heterocyclyl$^1$;
Heterocyclyl$^1$ is azetidinyl, pyrrolidinyl, piperidinyl, piperazinyl, or morpholinyl; wherein each Heterocyclyl$^1$ is optionally substituted with one or two substituents selected from $C_{1-4}$alkyl, hydroxy, halo, trifluoromethyl, $C_{1-4}$alkyloxycarbonyl, amino, $C_{1-4}$alkylaminocarbonyl, or $C_{1-4}$alkylsulfonyl;
$R^2$ is phenyl-(CO)— wherein the phenyl is substituted with one or two substituents each independently selected from hydrogen, halo, trifluoromethyl, $C_{1-4}$alkyl, $C_{1-4}$alkyloxy, or $C_{1-4}$alkylsulfonylamino;
or $R^2$ is a bicyclic heterocycle selected from cinnolinyl, quinazolinyl, or quinoxalinyl, wherein said bicyclic heterocycle is substituted with one or two substituents each independently selected from hydrogen, halo, trifluoromethyl, $C_{1-4}$alkyl, $C_{1-4}$alkyloxy, and $C_{1-4}$alkylsulfonylamino; and
$R^3$ is hydrogen, $C_{1-6}$alkyl, hydroxy, or halo;
or a pharmaceutically acceptable acid addition salt thereof.
As used in the foregoing definitions:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like; and
(CO) or (C=O) stands for carbonyl.
The term "compounds of the invention" as used herein, is meant to include the compounds of formula (I-a) and formula (I-b), which are both referred to as compounds of formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "compound of formula (I)" and "intermediates of synthesis of formula (I)" are meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms in so far as they may exist, although not explicitly indicated in the above formula (I) are intended to be included within the scope of the present invention.

It follows that a single compound may exist in both stereoisomeric and tautomeric form.

For the avoidance of doubt, compounds of formula (I) may contain the stated atoms in any of their natural or non-natural isotopic forms. In this respect, embodiments of the invention that may be mentioned include those in which (a) the compound of formula (I) is not isotopically enriched or labelled with respect to any atoms of the compound; and (b) the compound of formula (I) is isotopically enriched or labelled with respect to one or more atoms of the compound. Compounds of formula (I) that are isotopically enriched or labelled (with respect to one or more atoms of the compound) with one or more stable isotopes include, for example, compounds of formula (I) that are isotopically enriched or labelled with one or more atoms such as deuterium, $^{13}C$, $^{14}C$, $^{14}N$, $^{15}O$ or the like.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

Interesting compounds of formula (I) are those compounds of formula (I) wherein one or more of the following restrictions apply:
a) n is 0; or
b) n is 1; or
c) n is 2; or
d) $R^1$ is hydrogen; or
e) $R^1$ is hydroxy, $C_{1-4}$alkyl, amino, mono- or di($C_{1-4}$alkyl)amino, or Heterocyclyl$^1$; or
f) $R^1$ is or di($C_{1-4}$alkyl)amino; or
g) $R^1$ is Heterocyclyl$^1$; or
h) $R^2$ is phenyl-(CO)— wherein the phenyl is substituted with one or two substituents each independently selected from hydrogen, $C_{1-4}$alkyl, or $C_{1-4}$alkylsulfonylamino; or
i) $R^2$ is the bicyclic heterocycle quinazolinyl, wherein said bicyclic heterocycle is substituted with one or two substituents each independently selected from hydrogen, halo, trifluoromethyl, $C_{1-4}$alkyl, $C_{1-4}$alkyloxy, and $C_{1-4}$alkylsulfonyl-amino; or
j) $R^3$ is hydrogen; or
k) X is $CH_2$ and Z is $CH_2$; or
l) X is $CH_2$ and Z is O; or
m) X is $CH_2O$ and Z is $CH_2$; or
n) X is $NR^4$ wherein $R^4$ is $C_{1-4}$alkyl and Z is $CH_2$; or
o) Heterocyclyl$^1$ is pyrrolidinyl; or
p) Heterocyclyl$^1$ is morpholinyl.

In a first embodiment the present invention concerns compounds of formula (I-a) or formula (I-b), including any stereochemically isomeric form thereof, wherein n is an integer 0, 1 or 2;
X is $CH_2$, O, $CH_2O$ or $NR^4$, wherein $R^4$ is $C_{1-4}$alkyl;
Z is $CH_2$, O or $NR^4$, wherein $R^4$ is $C_{1-4}$alkyl;
and at least one of X or Z is $CH_2$;

$R^1$ is hydrogen, hydroxy, $C_{1-4}$alkyl, amino, mono- or di($C_{1-4}$alkyl)amino, or Heterocyclyl$^1$; Heterocyclyl$^1$ is pyrrolidinyl, or morpholinyl;

$R^2$ is phenyl-(CO)— wherein the phenyl is substituted with one or two substituents each independently selected from hydrogen, $C_{1-4}$alkyl, or $C_{1-4}$alkylsulfonylamino;

or $R^2$ is a bicyclic heterocycle selected from cinnolinyl, quinazolinyl, or quinoxalinyl, wherein said bicyclic heterocycle is substituted with one or two substituents each independently selected from hydrogen, halo, trifluoromethyl, $C_{1-4}$alkyl, $C_{1-4}$alkyloxy, and $C_{1-4}$alkylsulfonylamino; and $R^3$ is hydrogen;

or a pharmaceutically acceptable acid addition salt thereof.

A first group of compounds are those compounds of formula (I-a) wherein $R^1$ is hydrogen.

A second group of compounds are those compounds of formula (I-a) wherein $R^1$ is hydroxy, $C_{1-4}$alkyl, amino, mono- or di($C_{1-4}$alkyl)amino, or Heterocyclyl$^1$.

A third group of compounds are those compounds of formula (I-b) wherein $R^1$ is hydrogen.

A 4$^{th}$ group of compounds are those compounds of formula (I-b) wherein $R^1$ is hydroxy, $C_{1-4}$alkyl, amino, mono- or di($C_{1-4}$alkyl)amino, or Heterocyclyl$^1$.

A 5$^{th}$ group of compounds are those compounds of formula (I-a) wherein $R^1$ is Heterocyclyl$^1$; n is 0; and X is $CH_2$ and Z is $CH_2$.

A 6$^{th}$ group of compounds are those compounds of formula (I-a) wherein $R^1$ is Heterocyclyl$^1$; n is 1; and X is $CH_2$ and Z is $CH_2$.

A 7$^{th}$ group of compounds are those compounds of formula (I-a) wherein $R^1$ is Heterocyclyl$^1$; n is 2; and X is $CH_2$ and Z is $CH_2$.

A 8$^{th}$ group of compounds are those compounds of formula (I-b) wherein $R^1$ is Heterocyclyl$^1$; n is 0; and X is $CH_2$ and Z is $CH_2$.

A 9$^{th}$ group of compounds are those compounds of formula (I-b) wherein $R^1$ is Heterocyclyl$^1$; n is 1; and X is $CH_2$ and Z is $CH_2$.

A 10$^{th}$ group of compounds are those compounds of formula (I-b) wherein $R^1$ is Heterocyclyl$^1$; n is 2; and X is $CH_2$ and Z is $CH_2$.

A 11$^{th}$ group of compounds are those compounds of formula (I-a) wherein $R^1$ is Heterocyclyl$^1$; n is 0; and X is $CH_2$ and Z is O.

A 12$^{th}$ group of compounds are those compounds of formula (I-a) wherein $R^1$ is Heterocyclyl$^1$; n is 1; and X is $CH_2$ and Z is O.

A 13$^{th}$ group of compounds are those compounds of formula (I-a) wherein $R^1$ is Heterocyclyl$^1$; n is 0; and X is $CH_2O$ and Z is $CH_2$.

A 14$^{th}$ group of compounds are those compounds of formula (I-a) wherein $R^1$ is di($C_{1-4}$alkyl)amino; n is 1; and X is $NR^4$ wherein $R^4$ is $C_{1-4}$alkyl and Z is $CH_2$.

A 15$^{th}$ group of compounds are those compounds of formula (I-a) wherein $R^1$ is $C_{1-4}$alkyl; n is 1; and X is $CH_2$ and Z is $CH_2$.

A 16$^{th}$ group of compounds are those compounds of formula (I-b) wherein $R^1$ is $C_{1-4}$alkyl; n is 1; and X is $CH_2$ and Z is $CH_2$.

Compounds of formula (I-a) and (I-b), or their pharmaceutically acceptable salts, can be prepared according to the reaction schemes discussed herein below using synthetic methods known in the art of organic chemistry, or modifications and derivatisations that are familiar to those skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups well known the skilled person.

Unless otherwise indicated, the substituents in the schemes are defined as above. Isolation and purification of the products is accomplished by standard procedures, which are known to a chemist of ordinary skill.

General schemes 1-4 describe methods that were used to prepare compounds of the invention. The general methods described in these schemes can also be used to prepare additional compounds of the invention.

The starting material I is a protected (PG) piperidine bearing a carboxyl group on the carbon atom adjacent to the ring nitrogen that preferably has the (S) stereochemistry. This piperidine can also be substituted with different groups. Protecting groups on the piperidine ring nitrogen are preferably BOC or CBZ and can be introduced or removed during the synthesis using methods described in; Green and Wutts, protecting groups in Organic Synthesis 3$^{rd}$ Edition. In scheme 1 the carboxylic acid group on the N-protected cyclic aminoheterocycle I is first activated with a leaving group. Typical leaving groups are alkyl ester (e.g. methyl or ethyl ester) and these are generated by treatment of the carboxylic acid with the appropriate alcohol under non- or low-aqueous acidic conditions or by treatment with methyl iodide in the presence of a base like cesium carbonate or a like. Alternatively the acid can be activated as the Weinreb amide using standard peptide coupling procedures e.g. EDCI/HOBT, HATU, DCC, etc. Once the acid is activated as the ester or Weinreb amide II, the addition of an acetonitrile anion is performed. The anion generated from acetonitrile and a strong base e.g. lithium or sodium haxamethyldisilazide (LiHMDS) or alkyl lithium bases e.g. nBuLi, and when reacted with the ester or Weinreb amide generates the cyano ketone III. Reaction of the cyano ketone with hydrazine acetate salt then generates the aminopyrrazole intermediate IV. This is a key intermediate in the formation of the tricyclic heterocycles VI with different side chains through different condensation reactions. Condensation of amino pyrrazole IV with a cyclic keto-ester V generates the tricyclic analog VI. Treatment of VI with neat POCl$_3$ under elevated temperature (in some cases organic bases like diisopropylethyl amine or triethylamine can improve the reaction) then affords the chloride VII. Under the POCl$_3$ conditions acidic labile protecting groups e.g. BOC are typically removed but if this is partial further treatment with acid e.g. 4N HCl in dioxane can be used to remove the remaining BOC protected material. If other protecting groups are utilized then procedures described in Green and Wutts, Protecting groups in Organic Synthesis 3$^{rd}$ Edition can be used to remove the protecting group. Displacement of the chloride adjacent to the bridgehead nitrogen on VII can be effected with nucleophiles VIII, typically at room temperature to provide IX. A typical nucleophile VIII would be an amine that can be reacted in the absence or presence of a base such as triethylamine (scheme 1).

Scheme 1

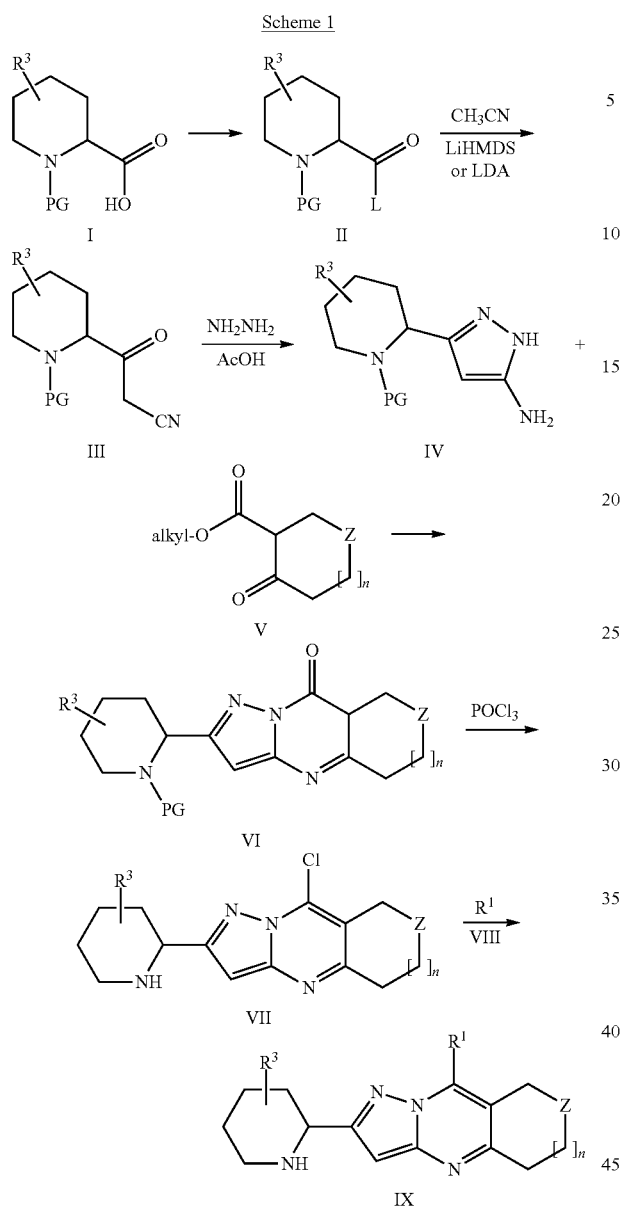

PG = protecting group BOC, CBZ
L = leaving group e.g. OMe, OEt

Compounds XI may be synthesized according to embodiments disclosed herein from a compound having an amino group IX, and a heterocyclic halide compound X. The reaction may be performed in the presence of a base and a Group 8-10 transition metal catalyst. One example of a reaction between a heterocyclic halide compound and an amine to produce an N-heterocyclic amine compound may be represented in scheme 2. Briefly, an heterocyclic halide X compound is reacted with an amine compound IX in the presence of a base and a Group 8-10 transition metal (M) complex including a chelating ligand (LL) to form an N-aryl amine compound. In certain embodiments, the Group 8-10 transition metal comprises at least one of palladium, platinum, and nickel. In some embodiments, the Group 8-10 transition metal is palladium. Alternatively this condensation maybe performed in a protic solvent such as alcohols or like preferably methoxy ethanol in the presence of an organic base such as di-isopropyl ethyl amine.

The heterocyclic compound used in the process of the present invention may be any heterocyclic compound of formula X:

Het-Y     formula X

Preferred heterocyclic groups, optionally substituted, as defined for the compounds of formula (I), in compound of formula X are the following:

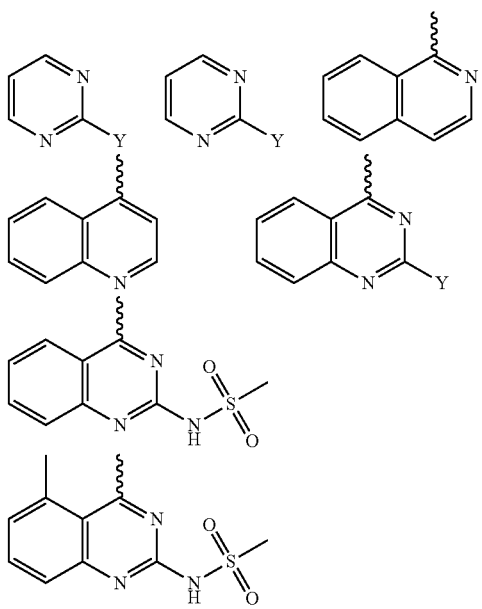

In formula X, Y may be any halide atom (F, Cl, Br, I), or any sulfur-containing leaving group (e.g., triflate, sulfonate, tosylate, and the like) known in the art. Chlorides are especially preferred in the process of the present invention (scheme 2).

Scheme 2

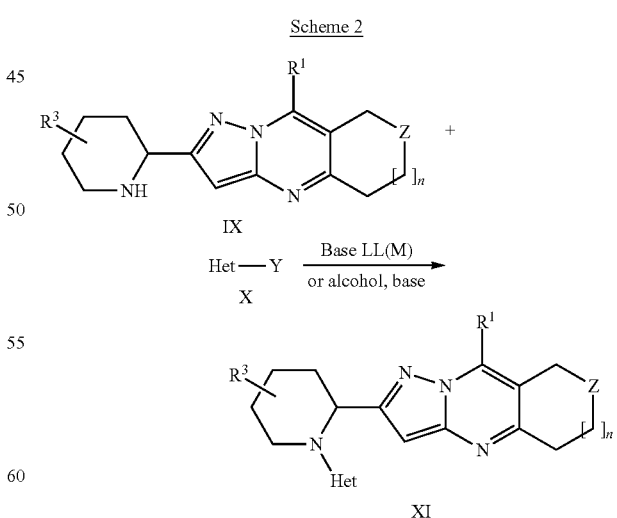

The unprotected NH in the cyloaminoalkyl ring on IX is acylated to provide XIV using standard procedures of either peptide coupling of acids XII using HATU/di-isopropyl-ethyl amine or generation of the acid chloride XIII using thionyl or oxalyl chloride and then addition to the compound IX in the presence of a base such as di-isopropyl-ethyl amine (scheme 3).

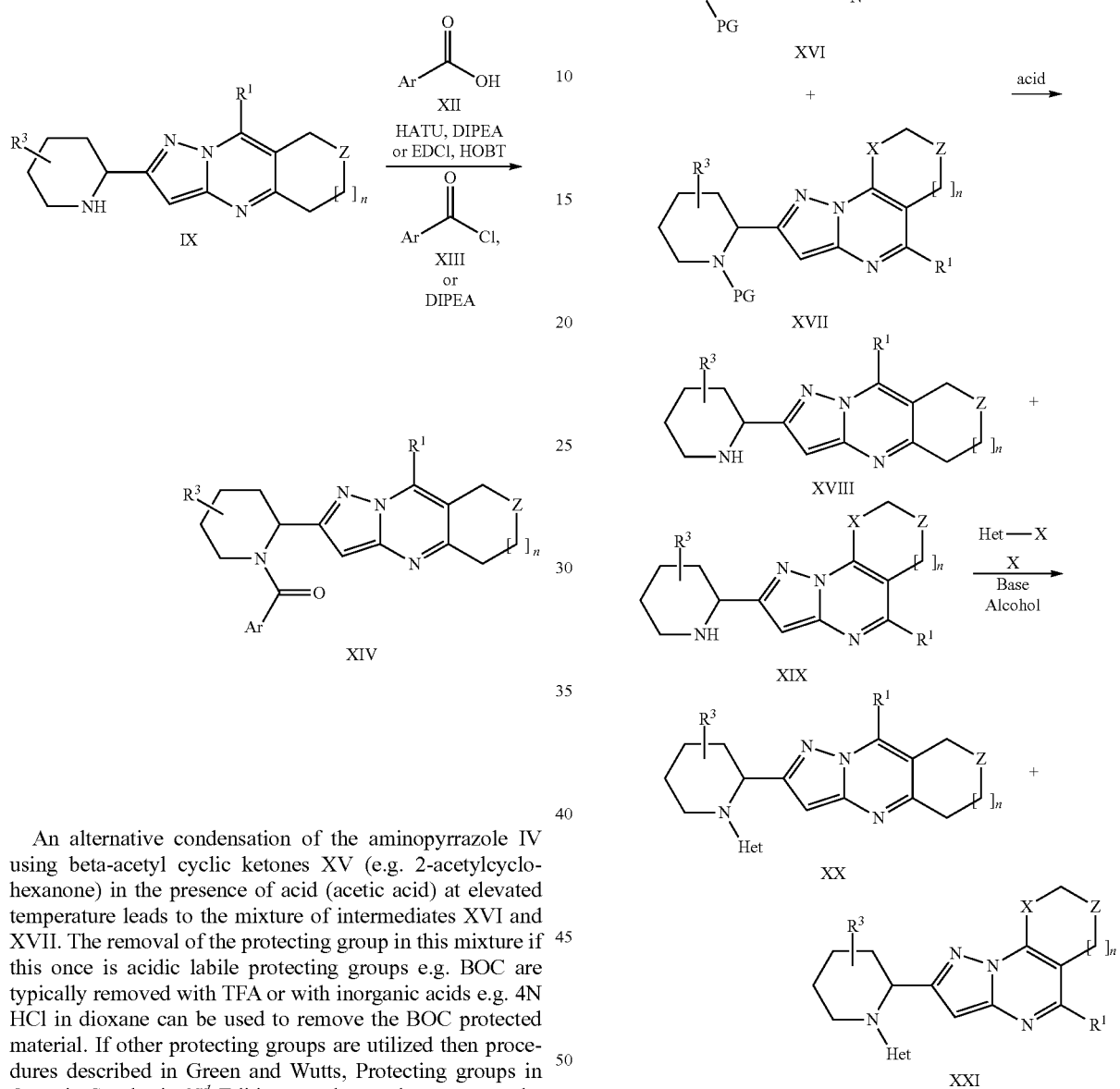

An alternative condensation of the aminopyrrazole IV using beta-acetyl cyclic ketones XV (e.g. 2-acetylcyclohexanone) in the presence of acid (acetic acid) at elevated temperature leads to the mixture of intermediates XVI and XVII. The removal of the protecting group in this mixture if this once is acidic labile protecting groups e.g. BOC are typically removed with TFA or with inorganic acids e.g. 4N HCl in dioxane can be used to remove the BOC protected material. If other protecting groups are utilized then procedures described in Green and Wutts, Protecting groups in Organic Synthesis 3$^{rd}$ Edition can be used to remove the protecting group. The free amine XVIII and XIX are alkylated by a variety of heterocycles as described in scheme 2 to produces the final compounds XX and XXI (scheme 4).

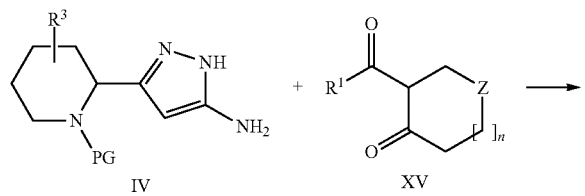

The compounds of formula (I-a) and (I-b) may further be prepared by converting compounds of formula (I-a) and (I-b) into each other according to art-known group transformation reactions.

The starting materials and some of the intermediates are known compounds and are commercially available or may be prepared according to conventional reaction procedures generally known in the art.

The compounds of formula (I-a) and (I-b) as prepared in the hereinabove described processes may be synthesized in the form of racemic mixtures of enantiomers which can be separated from one another following art-known resolution procedures. Those compounds of formula (I-a) and (I-b) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I-a) and (I-b) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I-a) and (I-b) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailability, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. in Antiviral Research, 38, p. 31-42 (1998).

Additionally the present invention provides pharmaceutical compositions comprising at least one pharmaceutically acceptable carrier and a therapeutically effective amount of a compound of formula (I-a) and (I-b).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I-a) and (I-b), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I-a) and (I-b) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I-a) and (I-b) may also be formulated in rectal compositions such as suppositories or retention enemas, e.g. containing conventional suppository bases such as cocoa butter and/or other glycerides.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I-a) and (I-b) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I-a) and (I-b) can be used as a medicine. Thus, the present invention also relates to a product containing (a) a compound of formula (I-a) and (I-b), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

EXPERIMENTAL PART

| Abbreviations | |
|---|---|
| $(M + H)^+$ | protonated molecular ion |
| aq. | aqueous |
| Boc | tert-butyloxycarbonyl |
| br | broad |
| $CH_3Cl$ | chloroform |
| $CH_3CN$ | acetonitrile |
| $CH_3OH$ | methanol |
| $CH_3ONa$ | sodium methanolate |
| d | doublet |
| DCM | dichloromethane |
| DIEA | N,N-diisopropylethylamine |
| DIPE | diisopropylether |
| DMF | dimethyl formamide |
| DMSO | dimethyl sulfoxide |
| Et | ethyl |
| eq. | equivalent |
| EtOAc | ethyl acetate |
| HOAc | acetic acid |
| LiHMDS | lithium bis(trimethylsilyl)amide |
| m/z: | mass-to-charge ratio |
| Me | methyl |
| MeCN | acetonitrile |
| MeOH | methanol |
| EtOH | ethanol |
| MHz | megahertz |
| min | minute(s) |
| $N_2$ | nitrogen |
| $Na_2SO_4$ | sodium sulfate |
| NMR | nuclear magnetic resonance (spectroscopy) |
| Pd(OAc)2 | palladium (II) acetate |
| Ph | phenyl |
| q | quartet |
| RT | room temperature |
| s | singlet |
| sat | saturated |
| t | triplet |
| TEA | triethyl amine |
| TFA | trifluoroacetic acid |
| THF | tetrahydrofuran |

NMR

For a number of compounds, $^1$H NMR spectra were recorded on a Bruker DPX-400 spectrometer operating at 400 MHz or on a Bruker DPX-360 operating at 360 MHz using chloroform-d (deuterated chloroform, $CDCl_3$) or DMSO-$d_6$ (deuterated DMSO, dimethyl-d6 sulfoxide) as solvent. Chemical shifts (δ) are reported in parts per million (ppm) relative to tetramethylsilane (TMS), which was used as internal standard.

A. Chemical Synthesis of Intermediates and Compounds of Formula (I-a) or (I-b)

N-(4-methyl-2-(2-(9-morpholino-5,6,7,8-tetrahydro-pyrazolo[5,1-b]quinazolin-2-yl)piperidine-1-carbonyl)phenyl)methanesulfonamide P1

-continued

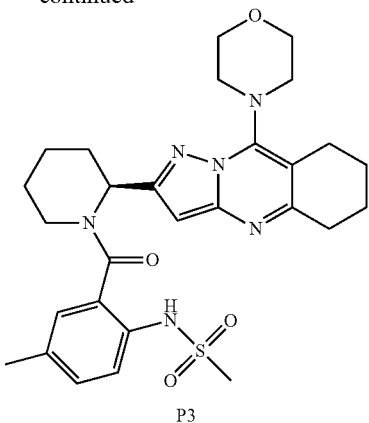

P3

Step 1: Synthesis of (S)-1-tert-butyl 2-methyl piperidine-1,2-dicarboxylate 2

Potassium carbonate (108.50 g, 785.09 mmol) was added to a solution of (S)-1-(tert-butoxycarbonyl)piperidine-2-carboxylic acid 1 (90 g, 392.55 mmol) in DMF (900 ml). Iodomethane (83.58 g, 588.82 mmol) was added to the mixture. The mixture was stirred at room temperature overnight. Ethyl acetate was added to the reaction mixture. The resulting mixture was washed with water and brine. The organic layer was dried over $Na_2SO_4$, filtered and concentrated under vacuum to give intermediate 2 (90 g, yield: 85%).
m/z=244 $(M+H)^+$.

Step 2: Synthesis of tert-butyl 2-(2-cyanoacetyl)piperidine-1-carboxylate 3

To a solution of $CH_3CN$ (1.30 ml, 24.66 mmol) in dry THF (40 ml), LiHMDS (22.61 ml, 22.61 mmol) was added dropwise at −78° C. The solution was stirred for 20 minutes at −78° C. A solution of 2 (5 g, 22.55 mmol) in dry THF (10 ml) was added dropwise to the mixture. The resulting mixture was stirred for 2 hours. Then the mixture was cooled to −78° C. and a solution of HOAc (5 ml, 76.67 mmol) in THF (50 ml) was added dropwise to the mixture. The solution was warmed to room temperature. The solvent was removed under vacuum. The residue was dissolved in ethyl acetate and washed with brine, dried $Na_2SO_4$, filtered and concentrated under vacuum to give the crude intermediate 3 (4 g, yield: 69%).
m/z=253 $(M+H)^+$.

Step 3: tert-butyl 2-(5-amino-1H-pyrazol-3-yl)piperidine-1-carboxylate 4

Hydrazine hydrate (100 ml) and ethanol (500 ml) were added to intermediate 3 (80 g, 317.70 mmol). The mixture was stirred at room temperature overnight. The solvent was removed under vacuum. The residue was dissolved in ethyl acetate, washed with brine. The organic layer was dried over $Na_2SO_4$, filtered and concentrated under vacuum to give intermediate 4 (80 g, yield: 76%).
m/z=267 $(M+H)^+$.
1H NMR (400 MHz, DMSO-$d_6$) δ ppm 1.41 (s, 14H) 1.99-2.16 (m, 1H) 2.67-2.85 (m, 1H) 3.76-3.91 (m, 1H) 4.30-4.93 (m, 2H) 4.95-5.22 (m, 2H) 10.86-11.42 (m, 1H).

Step 4: tert-butyl 2-(9-oxo-4,5,6,7,8,9-hexahydropyrazolo[5,1-b]quinazolin-2-yl)piperidine-1-carboxylate 5

Amino-pyrazolo-pyrimidine-boc-piperidine 4 (3 g, 11.26 mmol) was dissolved in EtOH (225 mL). Then methyl 2-oxocyclohexanecarboxylate (3.2 mL, 22.56 mmol) and AcOH (6.45 mL, 112.6 mmol) were added. The resulting mixture was stirred at reflux for 3 hours. The reaction mixture was cooled in an ice bath and stirred for 3 hours. The resulting white precipitate was filtered. The filtrate was evaporated and triturated in DIPE (60 mL) to give a white powder which is gathered with the white precipitate to give pure 5 (3.82 g, 100% pure, 91% yield).
LCMS (M+1)=373.
$^1$H NMR (400 MHz, DMSO-$d_6$) δ ppm 1.32-1.48 (m, 11H) 1.55 (br. s, 2H) 1.64-1.80 (m, 5H) 2.31 (d, J=13.64 Hz, 1H) 2.40 (t, J=6.16 Hz, 2H) 2.60 (t, J=5.28 Hz, 2H) 2.77 (br. s, 1H) 3.91 (d, J=13.20 Hz, 1H) 5.31 (br. s, 1H) 5.69 (s, 1H).

Step 5: tert-butyl 2-(9-chloro-5,6,7,8-tetrahydropyrazolo[5,1-b]quinazolin-2-yl)piperidine-1-carboxylate 6

Oxo-pyrazolo-pyrimidine-boc-piperidine 5 (800 mg, 2.15 mmol) was dissolved in dry ACN (15 mL) under inert atmosphere. Then DIPEA (1.85 mL, 10.74 mmol) and $POCl_3$ (0.6 mL, 6.4 mmol) were added. The mixture was stirred at 70° C. After 6 hours, the volatiles were co-evaporated with toluene. The crude was dissolved in a minimum amount of ACN and poured carefully in ice water (approximately 250 mL). The resulting precipitate was filtered.
The solid was dissolved in DCM, evaporated in vacuo and triturated with $Et_2O$ to give a sticky brown solid 6 (3.1 g, 90% pure, 80% yield).
LCMS: (M+1)=391.

Step 6: tert-butyl 2-[9-(morpholin-4-yl)-5,6,7,8-tetrahydropyrazolo[5,1-b]quinazolin-2-yl]piperidine-1-carboxylate 7

Chloro-pyrazolo-pyrimidine-boc-piperidine 6 (6.5 g, 16.62 mmol) was dissolved in dry THF (90 mL). Morpholine (7.32 mL, 83.14 mmol) was added under inert atmosphere. The mixture was stirred at 50° C. for 3 days. The volatiles were removed under reduce pressure. The crude was dissolved in water, extracted with EtOAc and washed with brine. The organic layer was dried over magnesium sulfate and evaporated to give a brown pale powder 7 (5.5 g, 93% pure, 80% yield).
LCMS: (M+1)=442.
$^1$H NMR (400 MHz, DMSO-$d_6$) δ ppm 1.35 (br. s., 2H) 1.40 (br. s., 9H) 1.51-1.59 (m, 2H) 1.69-1.82 (m, 5H) 2.29 (d, J=12.98 Hz, 1H) 2.71 (t, J=6.16 Hz, 2H) 2.80 (t, J=6.60 Hz, 2H) 2.86-2.96 (m, 1H) 3.43-3.51 (m, 4H) 3.72-3.79 (m, 4H) 3.90 (d, J=12.54 Hz, 1H) 5.40 (br. s., 1H) 6.11 (s, 1H).

Step 7: 9-(morpholin-4-yl)-2-(piperidin-2-yl)-5,6,7,8-tetrahydropyrazolo[5,1-b]quinazoline 8

Morpholino-pyrazolo-pyrimidine-boc-piperidine 7 (4 g, 9.06 mmol) was dissolved in DCM (100 mL). TFA (3.9 mL, 50.95 mmol, 5.6 eq.) was added under inert atmosphere. The mixture was stirred at room temperature during 3 days. The volatiles were removed under reduce pressure at 40° C. Then the crude was dissolved in water and successively basified with a saturated aqueous solution of Na₂CO₃ extracted with DCM and washed with water.

The organic layer was dried over magnesium sulfate and evaporated. The crude was triturated in Et₂O to yield intermediate 8 as a pale yellow solid (2.6 g, 100% pure, 84% yield).

LCMS: (M+1)=342.

¹H NMR (400 MHz, DMSO-d₆) δ ppm 1.46-1.54 (m, 2H) 1.60 (dd, J=12.87, 9.79 Hz, 2H) 1.70-1.77 (m, 2H) 1.78-1.85 (m, 3H) 1.95-2.01 (m, 1H) 2.73 (t, J=6.16 Hz, 2H) 2.75-2.79 (m, 1H) 2.81 (t, J=6.38 Hz, 2H) 3.10 (d, J=11.66 Hz, 1H) 3.47 (t, J=4.40 Hz, 4H) 3.77 (t, J=4.40 Hz, 4H) 3.88-3.94 (m, 1H) 6.31 (s, 1H).

Step 8: N-(4-methyl-2-(2-(9-morpholino-5,6,7,8-tetrahydropyrazolo[5,1-b]quinazolin-2-yl)-piperidine-1-carbonyl)phenyl)methanesulfonamide P1 a) Synthesis of 5-methyl-2-[(methylsulfonyl)amino]benzoyl Chloride 9

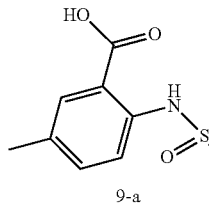 

9-a

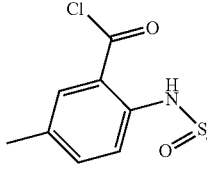

9

To a solution of methyl-sulfone methyl amide benzoic acid 9-a (500 mg, 2.2 mmol) in DCM (5 mL) under inert atmosphere thionyl chloride (0.8 mL, 11 mmol, 5 eq.) was added. The reaction mixture was stirred at room temperature for 2 hours and at 50° C. for 1 hour. After cooling down to room temperature the reaction mixture was co-evaporated in the vacuo with toluene twice. The crude intermediate 9 (500 mg, 92% yield) was used as such for the next step.

b) Morpholino-pyrazolo-pyrimidine-piperidine 8 (345 mg, 1 mmol) was dissolved in DCM (4 mL). Then triethylamine (0.280 mL, 2 mmol) and a solution of 5-methyl-2-[(methyl-sulfonyl)amino]benzoyl chloride 9 (500 mg, 2 mmol, 2 eq.) in DCM (2 mL) were added. The resulting mixture was stirred at room temperature overnight.

Then the reaction mixture was evaporated under reduce pressure and purified by reverse phase HPLC to give compound P1 as a white powder (35 mg, 97% pure, 6% yield).

LCMS (M+1)=553.

¹H NMR (380 K, 400 MHz, DMSO-d₆) δ ppm 1.53-1.71 (m, 4H) 1.78 (s, 4H) 1.94-2.06 (m, 1H) 2.27 (s, 3H) 2.30-2.38 (m, 1H) 2.77 (t, J=6.40 Hz, 2H) 2.84 (t, J=6.60 Hz, 3H) 3.01 (s, 3H) 3.13-3.24 (m, 1H) 3.51 (t, J=4.40 Hz, 4H) 3.80 (t, J=4.20 Hz, 4H) 3.92 (br. s, 1H) 5.63 (br. s, 1H) 6.31 (s, 1H) 7.18-7.25 (m, 2H) 7.34 (d, J=8.14 Hz, 1H).

Another batch of this compound (333 mg) was purified by SFC to give the two enantiomers (R)—N-(4-methyl-2-(2-(9-morpholino-5,6,7,8-tetrahydropyrazolo[5,1-b]quinazolin-2-yl)-piperidine-1-carbonyl)phenyl)methanesulfonamide P2, and (S)—N-(4-methyl-2-(2-(9-morpholino-5,6,7,8-tetrahydropyrazolo[5,1-b]quinazolin-2-yl)piperidine-1-carbonyl)-phenyl)methanesulfonamide P3

Synthesis of 4-(2-(1-(6-methylquinazolin-4-yl)piperidin-2-yl)-5,6,7,8-tetrahydropyrazolo[5,1-b]quinazolin-9-yl)morpholine P4

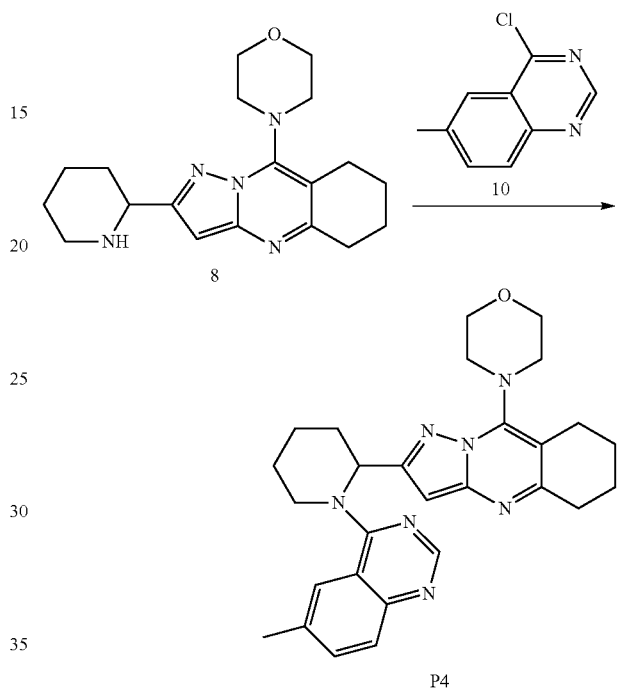

Synthesis of 6-methylquinazolin-4-ol 10-b

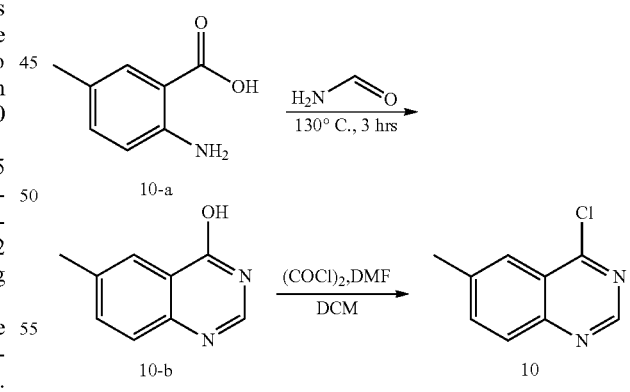

Step 1

2-Amino-5-methylbenzoic acid 10-a (5 g, 33.08 mmol) was added to formamide (30 ml). The reaction mixture was heated to 100° C. for 6 hours. The solid was collected by filtration and washed several times with ethanol to give intermediate 10-b (4.5 g, 76%).

m/z=161 (M+H)⁺.

Step 2: Synthesis of 4-chloro-6-methylquinazoline 10

Intermediate 10-b (2.1 g, 13.11 mmol) was dissolved in CHCl$_3$ (30 ml). Oxalyl chloride (1.97 g, 23.26 mmol) and DMF (0.1 ml) were added. The mixture was heated to 100° C. for 3 hours. The solvent was evaporated to get intermediate 10 (1.5 g, 58%).

m/z=179 (M+H)$^+$.

Step 3: Synthesis of 4-(2-(1-(6-methylquinazolin-4-yl)piperidin-2-yl)-5,6,7,8-tetrahydropyrazolo[5,1-b]quinazolin-9-yl)morpholine P4

Intermediate 8 (100 mg, 0.30 mmol) was dissolved in 2-methoxyethanol (3 mL). Then 4-chloro-6-methylquinazoline 10 (78.47 mg, 0.44 mmol, 1.5 eq.) and DIPEA (0.150 mL, 0.88 mmol, 3 eq.) were added. The reaction mixture was stirred at 80° C. during 1 night. The reaction mixture was cooled to room temperature and evaporated under reduce pressure. The crude was purified by reverse phase HPLC to give compound P4 (21 mg, 100% pure, 15% yield).

LCMS (M+1)=484.

$^1$H NMR (400 MHz, DMSO-d$_6$) δ ppm 1.60-1.85 (m, 8H) 2.00-2.14 (m, 1H) 2.43 (s, 3H) 2.46 (br. s., 1H) 2.71 (t, J=6.16 Hz, 2H) 2.80 (t, J=6.60 Hz, 2H) 3.39-3.46 (m, 5H) 3.66 (t, J=4.18 Hz, 4H) 4.20 (d, J=12.76 Hz, 1H) 5.92 (d, J=2.64 Hz, 1H) 6.31 (s, 1H) 7.63 (dd, J=8.58, 1.54 Hz, 1H) 7.71 (d, J=8.58 Hz, 1H) 7.87 (s, 1H) 8.55 (s, 1H).

Synthesis of 4-(2-(1-(5-methylquinazolin-4-yl)piperidin-2-yl)-5,6,7,8-tetrahydropyrazolo[5,1-b]quinazolin-9-yl)morpholine P5

Intermediate 8 (200 mg, 0.59 mmol) was dissolved in 2-methoxyethanol (6 mL). Then 4-chloro-5-methylquinazoline 11 (165 mg, 0.88 mmol, 1.5 eq.) and DIPEA (0.30 mL, 1.75 mmol, 3 eq.) were added. The reaction mixture was stirred at 80° C. during 1 day, cooled to room temperature and evaporated under reduce pressure. The crude was dissolved in DCM and washed with a saturated solution of sodium carbonate. The organic layer was dried over magnesium sulfate and evaporated. The residue was purified by reverse phase HPLC to give compound P5 (101 mg, 100% pure, 36% yield) as a white powder.

LCMS (M+1)=484.

$^1$H NMR (420 K, 400 MHz, DMSO-d$_6$) δ ppm 1.67-1.96 (m, 8H) 2.23-2.36 (m, 2H) 2.74-2.76 (m, 2H) 2.80 (t, J=6.60 Hz, 2H) 2.89 (s, 3H) 3.34-3.40 (m, 4H) 3.56 (d, J=12.32 Hz, 2H) 3.73 (t, J=4.62 Hz, 4H) 5.63 (br. s., 1H) 6.05 (br. s., 1H) 7.31-7.37 (m, 1H) 7.60-7.65 (m, 2H) 8.50 (s, 1H).

Synthesis of N-(5-methyl-4-(2-(9-morpholino-5,6,7,8-tetrahydropyrazolo[5,1-b]-quinazolin-2-yl)piperidin-1-yl)quinazolin-2-yl)methanesulfonamide P7

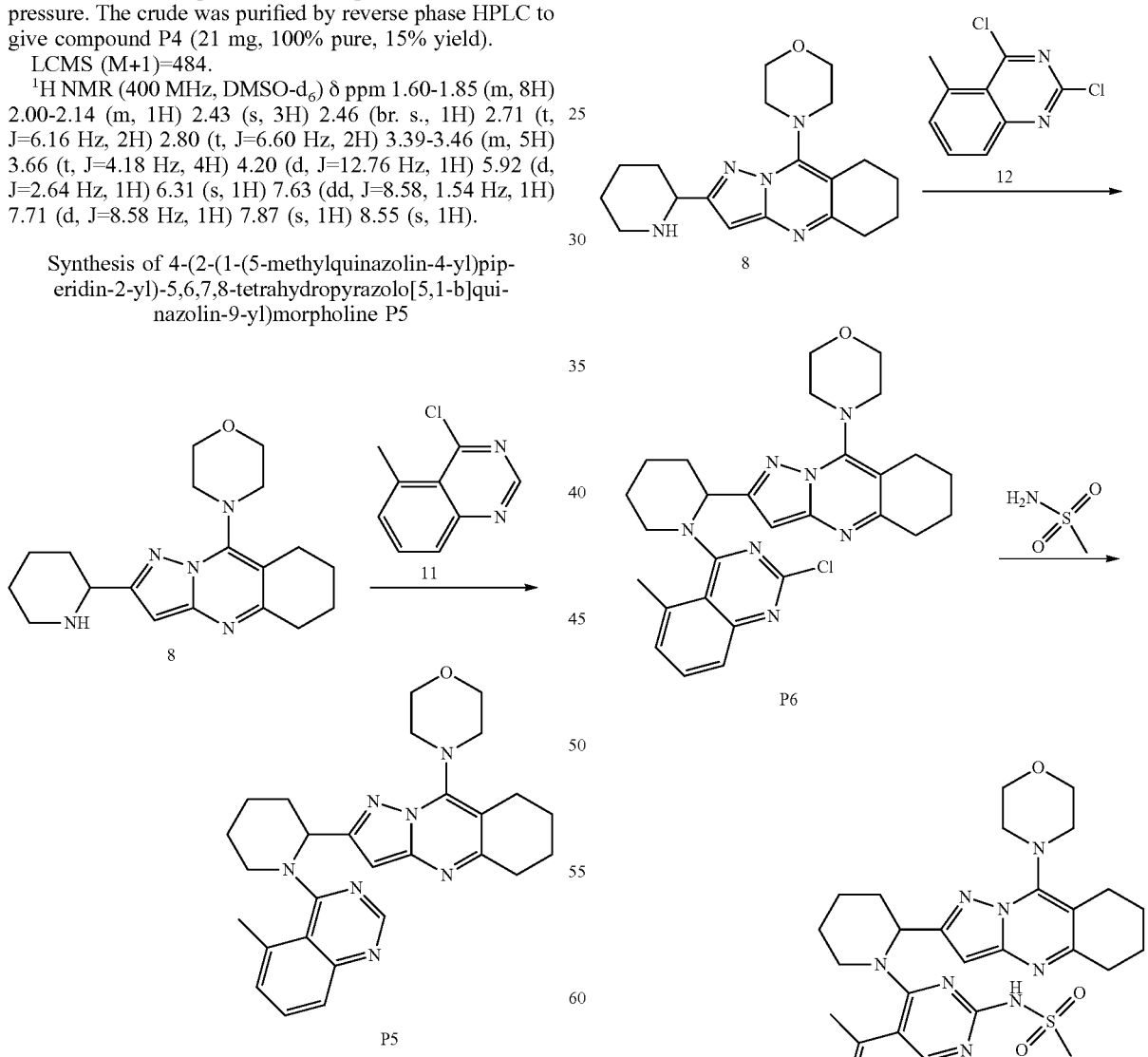

Step 1: Synthesis of 4-(2-(1-(2-chloro-5-methylqui-nazolin-4-yl)piperidin-2-yl)-5,6,7,8-tetrahydropyra-zolo[5,1-b]quinazolin-9-yl)morpholine P6

Synthesis of intermediate 2,4-dichloro-5-methylquinazoline 12

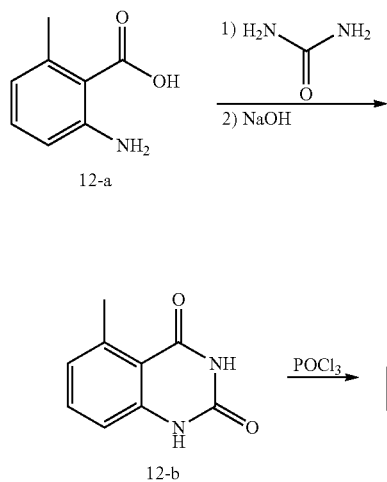

Synthesis of 5-methylquinazoline-2,4(1H,3H)-dione 12-b

2-Amino-6-methylbenzoic acid 12-a (10 g, 66.15 mmol) and urea (39.73 g, 661.54 mmol) were heated to 160° C. and stirred for 6 hours, the reaction mixture was cooled to 100° C. and 40 ml of $H_2O$ was added. The obtained suspension was left to stir for 10 min and cooled to room temperature. The precipitate was filtered off and was dissolved in an aqueous 0.2 M sodium hydroxide solution (100 ml). The solution was heated to 100° C. for 5 min, causing a white precipitate to form. The reaction mixture was stirred at room temperature overnight, the solution was neutralized to pH=7 with concentrated HCl and the white solid was filtered off. The obtained solid was washed with water, triturated with hot ethyl acetate (100 ml), and cooled to room temperature. The filtrate was collected and dried under vacuum to yield intermediate 12-b (6.4 g, yield: 49%).

m/z=177 $(M+H)^+$.

Synthesis of 2,4-dichloro-5-methylquinazoline 12

A mixture of intermediate 12-b (1 g, 5.68 mmol), diethylaniline (2.267 ml, 14.19 mmol) in $POCl_3$ (5 ml) was refluxed for 2 hours. The mixture was cautiously poured over crushed ice. The mixture was neutralized to pH=7 with saturated $NaHCO_3$. The resulting mixture was extracted with $CH_2Cl_2$ (2×15 ml). The combined organic layers were washed with brine, dried over $Na_2SO_4$ and filtered. The filtrate was concentrated under vacuum to yield intermediate 12 (950 mg, yield: 68%).

m/z=214 $(M+H)^+$.

Step 1: Synthesis of 4-(2-(1-(2-chloro-5-methylqui-nazolin-4-yl)piperidin-2-yl)-5,6,7,8-tetrahydropyra-zolo[5,1-b]quinazolin-9-yl)morpholine P6

Intermediate 8 (300 mg, 0.88 mmol) was dissolved in 2-methoxyethanol (6 mL). Then 2,4-dichloro-5-methylquinazoline (281 mg, 1.32 mmol, 1.5 eq.) and DIPEA (0.45 mL, 2.63 mmol, 3 eq.) were added. The reaction mixture was stirred at 50° C. during 16 hours then evaporated under reduce pressure. The crude was dissolved in DCM, washed two times with a saturated solution of sodium carbonate. The combined organic layers were dried over magnesium sulfate, filtered and concentrated in vacuo. The residue was purified by reverse phase HPLC to give compound P6 (110 mg, 100% pure, 24% yield).

LCMS (M+1)=518.

$^1H$ NMR (420 K, 400 MHz, DMSO-$d_6$) δ ppm 1.62 (br. s., 1H) 1.67-1.95 (m, 7H) 2.19-2.31 (m, 1H) 2.33-2.42 (m, 1H) 2.74 (br. s., 4H) 2.80-2.84 (m, 4H) 3.38 (br. s., 4H) 3.60 (t, J=11.40 Hz, 1H) 3.70-3.78 (m, 4H) 5.69 (br. s., 1H) 6.14 (br. s., 1H) 7.35 (d, J=7.26 Hz, 1H) 7.52 (d, J=8.36 Hz, 1H) 7.61-7.70 (m, 1H).

Step 2: Synthesis of N-(5-methyl-4-(2-(9-mor-pholino-5,6,7,8-tetrahydropyrazolo[5,1-b]-quinazo-lin-2-yl)piperidin-1-yl)quinazolin-2-yl)methanesul-fonamide P7

Compound P6 (150 mg, 0.18 mmol) was dissolved in 1,4-dioxane (5 mL) in a sealed tube. Methane sulfonamide (34.7 mg, 0.37 mmol, 2 eq.), $Cs_2CO_3$ (149 mg, 0.47 mmol, 2.5 eq.), 4,5-bis(diphenylphosphino)-9,9-dimethylxanthene (32 mg, 0.057 mmol, 0.3 eq.) and palladium acetate (12.3 mg, 0.057 mmol, 0.3 eq.) were then added. The reaction mixture was heated to 120° C. in the microwave during 10 minutes. Then filtered over decalite, rinsed with DCM. The solution was evaporated under reduce pressure. The crude was purified by reverse phase HPLC giving compound P7 (30 mg, 100% pure, 29% yield).

LCMS (M+1)=577.

$^1H$ NMR (400 MHz, DMSO-$d_6$) δ ppm 1.44-1.92 (m, 8H) 2.14-2.27 (m, 1H) 2.35-2.42 (m, 1H) 2.66 (s, 3H) 2.74 (t, J=6.60 Hz, 2H) 2.80 (t, J=6.65 Hz, 2H) 2.92 (s, 3H) 3.32-3.46 (m, 4H) 3.56 (m, J=12.40, 12.40 Hz, 1H) 3.73 (t, J=4.67 Hz, 4H) 3.82 (d, J=14.72 Hz, 1H) 5.97 (s, 1H) 6.18 (s, 1H) 7.07 (d, J=7.32 Hz, 1H) 7.23 (d, J=8.21 Hz, 1H) 7.48 (t, J=7.79 Hz, 1H) 10.55 (s, 1H).

Synthesis of N-(6-methyl-4-(2-(9-morpholino-5,6,7,8-tetrahydropyrazolo[5,1-b]-quinazolin-2-yl)piperi-din-1-yl)quinazolin-2-yl)methanesulfonamide P9

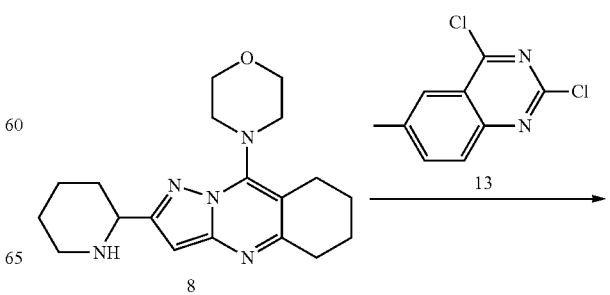

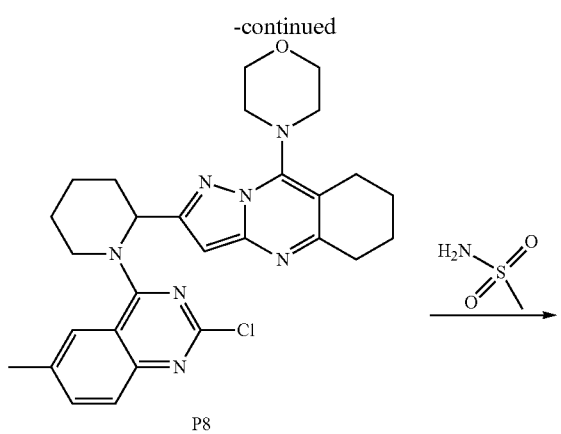

Step 1: Synthesis of 4-(2-(1-(2-chloro-6-methylquinazolin-4-yl)piperidin-2-yl)-5,6,7,8-tetrahydropyrazolo[5,1-b]quinazolin-9-yl)morpholine P8

Intermediate 8 (100 mg, 0.29 mmol) was dissolved in 2-methoxyethanol (3 mL). Then 2,4-dichloro-6-methylquinazoline 13 (93.6 mg, 0.44 mmol, 1.56 eq.) and DIPEA (0.150 mL, 0.88 mmol, 3.1 eq.) were added. The reaction mixture was stirred at 40° C. during 1 night, cooled to room temperature and evaporated under reduce pressure.

The crude was dissolved in DCM and washed with water. The organic layer was dried over magnesium sulfate and evaporated. The crude was recrystallized in a mixture of DIPE and ACN to give a white precipitate which was filtered to give compound P8 (60 mg, 100% pure, 41% yield).

LCMS (M+1): 518.

$^1$H NMR (400 MHz, DMSO-$d_6$) δ ppm 1.66-1.77 (m, 6H) 1.77-1.85 (m, 2H) 2.02-2.11 (m, 1H) 2.41 (s, 3H) 2.43-2.47 (m, 1H) 2.71 (s, 2H) 2.79-2.85 (m, 2H) 3.37-3.48 (m, 5H) 3.61-3.67 (m, 4H) 4.23-4.32 (m, 1H) 5.99-6.03 (m, 1H) 6.38 (s, 1H) 7.64 (s, 1H) 7.66 (d, J=1.32 Hz, 1H) 7.89 (s, 1H).

Step 2: Synthesis of P9

Compound P8 (110 mg, 0.21 mmol) was dissolved in 1,4-dioxane (5 mL) in a sealed tube. Methane sulfonamide (40.4 mg, 0.43 mmol, 2 eq.), Cs$_2$CO$_3$ (173 mg, 0.53 mmol, 2.5 eq.), 4,5-bis(diphenylphosphino)-9,9-dimethylxanthene (37 mg, 0.064 mmol, 0.3 eq.) and palladium acetate (14.3 mg, 0.064 mmol, 0.3 eq.) were added. The reaction mixture was heated to 100° C. in the microwave during 20 minutes then filtered over dicalite, rinsed with DCM. The solution was evaporated under reduce pressure and purified by reverse phase HPLC.

The product fraction was evaporated and triturated in Et$_2$O giving compound P9 (20 mg, 100% pure, 16% yield) as a white powder.

LCMS (M+1)=577.

$^1$H NMR (360 K, 400 MHz, DMSO-$d_6$) δ ppm 1.72-1.82 (m, 6H) 1.82-1.89 (m, 2H) 2.12 (dd, J=13.53, 5.17 Hz, 1H) 2.35 (s, 3H) 2.46-2.50 (m, 1H) 2.76 (t, J=6.27 Hz, 2H) 2.85 (t, J=6.60 Hz, 2H) 2.96 (s, 3H) 3.43-3.50 (m, 5H) 3.71 (t, J=4.18 Hz, 4H) 4.48 (d, J=12.76 Hz, 1H) 6.20 (d, J=3.52 Hz, 1H) 6.42 (s, 1H) 7.37 (d, J=8.58 Hz, 1H) 7.53 (dd, J=8.47, 1.43 Hz, 1H) 7.78 (s, 1H).

Synthesis of 4-(2-(1-(5-fluoroquinazolin-4-yl)piperidin-2-yl)-5,6,7,8-tetrahydropyrazolo-[5,1-b]quinazolin-9-yl)morpholine P10

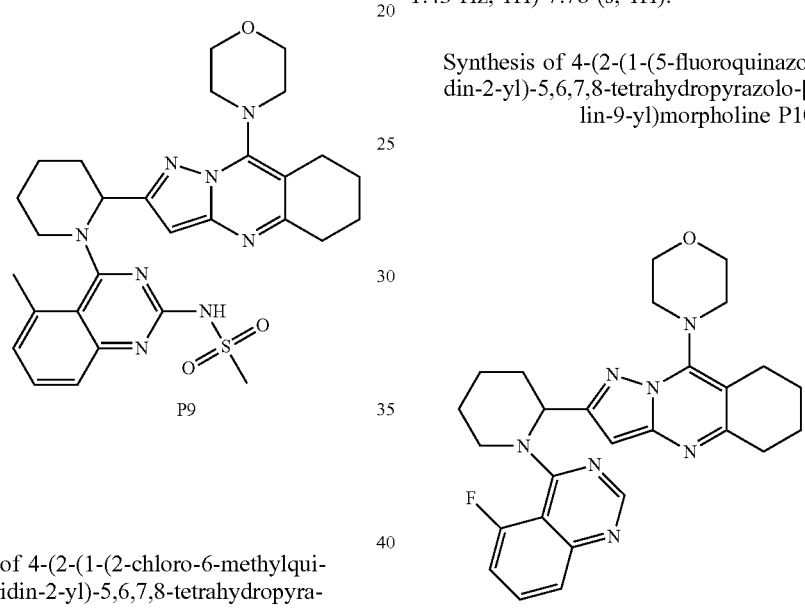

Intermediate 8 (200 mg, 0.59 mmol) was dissolved in 2-methoxyethanol (6 mL). 4-chloro-5-fluoroquinazoline (160 mg, 0.88 mmol, 1.5 eq.) and DIPEA (0.30 mL, 1.76 mmol, 3 eq.) were added. The reaction mixture was stirred at 50° C. during 1 hour then cooled to room temperature and poured into ice/water. The water layer was extracted with DCM (2×50 mL). The combined organics were washed with water, dried over magnesium sulfate and concentrated in vacuo. The residue was purified on silica column with a gradient from pure DCM to DCM/MeOH (9/1). The product fractions were evaporated under reduce pressure and the residue was triturated in Et$_2$O to give compound 18 (230 mg, 100% pure, 81% yield).

LCMS (M+1)=488.

$^1$H NMR (400 MHz, DMSO-$d_6$) δ ppm 1.56-1.86 (m, 8H) 2.01-2.17 (m, 1H) 2.48 (br. s., 1H) 2.68 (t, J=6.16 Hz, 2H) 2.79 (t, J=6.60 Hz, 2H) 3.34-3.44 (m, 5H) 3.60-3.68 (m, 4H) 3.83-3.97 (m, 1H) 5.81-5.93 (m, 1H) 6.17 (s, 1H) 7.28-7.38 (m, 1H) 7.63 (dd, J=8.36, 0.88 Hz, 1H) 7.75-7.84 (m, 1H) 8.53 (s, 1H).

Synthesis of 4-(2-(1-(5-(trifluoromethyl)quinazolin-4-yl)piperidin-2-yl)-5,6,7,8-tetrahydropyrazolo[5,1-b]quinazolin-9-yl)morpholine P11

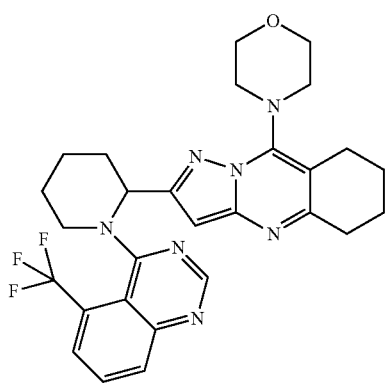

P11

Synthesis of 4-chloro-5-(trifluoromethyl)quinazoline 14

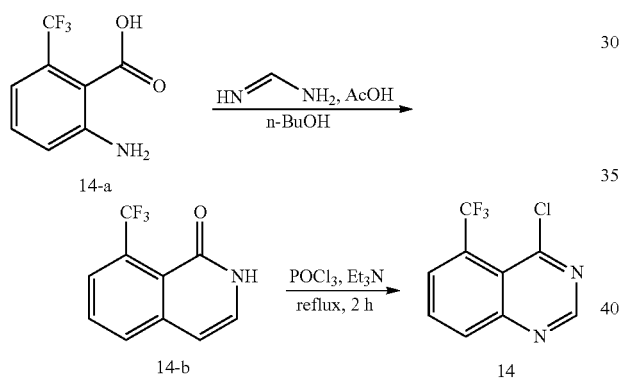

Step 1: Synthesis of 5-(trifluoromethyl)quinazolin-4(3H)-one 14-b

A mixture of 2-amino-6-(trifluoromethyl)benzoic acid 14-a (9.00 g, 43.9 mmol) and formamidine acetate (22.84 g, 219.4 mmol) in n-butanol (180 ml) was stirred at 100° C. for 5 hours. The solvent was evaporated under vacuum. The residue was washed with ethanol (2×50 ml) and then dried in vacuum at 45° C. for 1 hour to give intermediate 14-b (9 g, yield: 91%).

Step 2: Synthesis of 4-chloro-5-(trifluoromethyl)quinazoline 14

Triethyl amine (29.3 ml, 210 mmol) was added to a mixture of intermediate 14-b (8.00 g, 37.4 mmol) in phosphorus oxychloride (331 g, 2.16 mol) at 0° C. The mixture was refluxed for 2 hours. The solvent was evaporated under vacuum. The residue was dissolved in ethyl acetate (200 ml) and the mixture was added to ice (200 g). The separated organic layer was washed successively with water (1×100 ml), 10% sodium bicarbonate aqueous solution (2×100 ml), water (1×100 ml) and brine (1×100 ml). The separated organic layer was dried over sodium sulfate, filtered and concentrated under vacuum. The residue was purified by column chromatography over silica gel (eluent: petroleum ether/ethyl acetate 1/0 to 1/1) to give intermediate 14 (7.97 g, 91.38%).

$^1$H NMR (400 MHz, CDCl$_3$) δ ppm 7.89-8.06 (m, 1H) 8.22 (d, J=7.50 Hz, 1H) 8.31 (d, J=8.38 Hz, 1H) 9.11 (s, 1H)

Synthesis of 4-(2-(1-(5-(trifluoromethyl)quinazolin-4-yl)piperidin-2-yl)-5,6,7,8-tetrahydropyrazolo[5,1-b]quinazolin-9-yl)morpholine P11

To a solution of Intermediate 8 (150 mg, 0.44 mmol) in 2-methoxyethanol (5 mL), 4-chloro-5-(trifluoromethyl)quinazoline 14 (123 mg, 0.53 mmol, 1.2 eq.) and DIPEA (0.30 mL, 1.8 mmol, 4 eq.) were added. The resulting mixture was stirred at 50° C. for 17 hours. The reaction mixture was then cooled to room temperature and poured into iced water solution. The resulting mixture was stirred until the ice melted, then extracted once with DCM and once with EtOAc. The combined organics were dried over magnesium sulfate and evaporated in the vacuo. The crude was directly purified on silica gel with a gradient from pure DCM to DCM/MeOH (95/5). The product fraction was evaporated to give compound P11 as a pale yellow powder (122 mg, 100% pure, 51% yield).

LCMS (M+1)=538.

$^1$H NMR (420 K, 400 MHz, DMSO-d$_6$) δ ppm 1.61-1.95 (m, 8H) 2.13-2.25 (m, 1H) 2.28-2.38 (m, 1H) 2.66-2.73 (m, 2H) 2.77-2.84 (m, 2H) 3.29-3.40 (m, 4H) 3.40-3.57 (m, 2H) 3.69-3.78 (m, 4H) 5.74 (br. s., 1H) 5.95 (br. s., 1H) 7.79-7.92 (m, 2H) 7.99 (d, J=7.70 Hz, 1H) 8.51 (br. s., 1H).

Synthesis of 4-(2-(1-(5-methoxyquinazolin-4-yl)piperidin-2-yl)-5,6,7,8-tetrahydropyrazolo[5,1-b]quinazolin-9-yl)morpholine P12

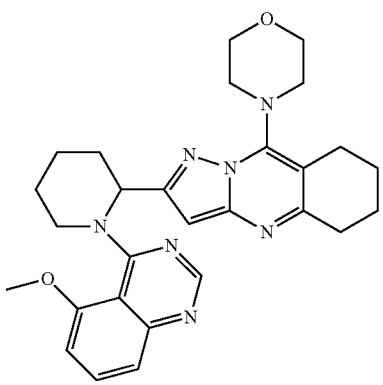

P12

To a solution of intermediate 8 (150 mg, 0.44 mmol) in 2-methoxyethanol (5 mL), 4-chloro-5-methoxyquinazoline (123 mg, 0.53 mmol, 1.2 eq.) and DIPEA (0.23 mL, 1.31 mmol, 3 eq.) were added. The mixture was stirred at 50° C. for 17 hours. The reaction mixture was cooled to room temperature and poured into water cooled by ice. The resulting milky solution was extracted with EtOAc. The combined organics were dried over magnesium sulfate and evaporated in vacuo. The crude was purified on silica gel with a gradient from pure DCM to DCM/MeOH (95/5). The product fraction was evaporated to give compound P12 powder (110 mg, 100% pure, 50% yield) as a pale yellow solid.

LCMS (M+1)=500.

$^1$H NMR (420 K, 400 MHz, DMSO-d$_6$) δ ppm 1.65-1.86 (m, 8H) 2.05-2.23 (m, 1H) 2.46 (br. s., 1H) 2.72-2.76 (m, 2H) 2.81 (t, J=6.16 Hz, 2H) 3.41 (d, J=3.74 Hz, 4H) 3.44 (br. s., 1H) 3.74 (br. s., 4H) 3.92-3.95 (m, 1H) 3.96 (s, 3H) 5.90 (br. s., 1H) 6.09 (s, 1H) 7.00 (d, J=7.92 Hz, 1H) 7.33 (d, J=8.14 Hz, 1H) 7.64 (t, J=8.03 Hz, 1H) 8.39 (s, 1H).

Synthesis of 4-(2-(1-(6-ethyl-5-methylquinazolin-4-yl)piperidin-2-yl)-5,6,7,8-tetrahydropyrazolo[5,1-b]quinazolin-9-yl)morpholine P13

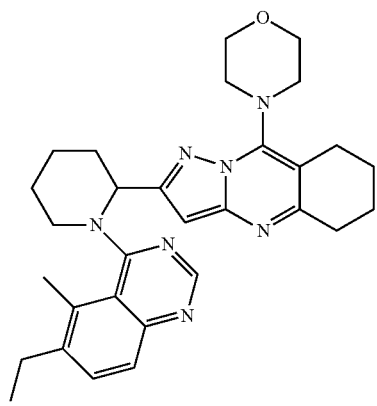

P13

Synthesis of 4-chloro-6-ethyl-5-methylquinazoline 15

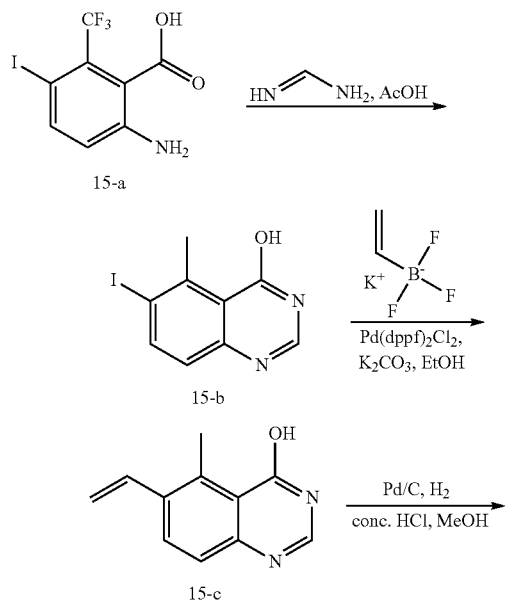

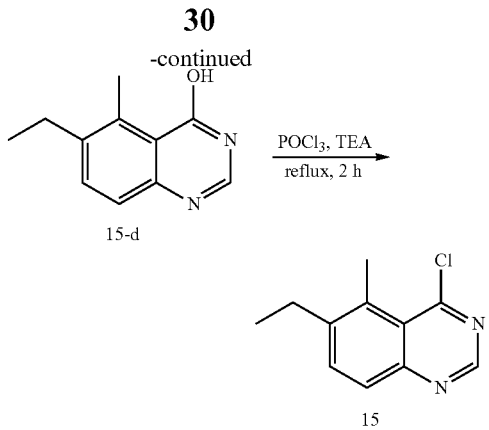

15

Step 1: Synthesis of 6-iodo-5-methylquinazolin-4-ol 15-b

A solution of 6-amino-3-iodo-2-methylbenzoic acid 15-a (35.0 g, 126 mmol) and formamidine acetate (59.0 g, 567 mmol) in EtOH (500 ml) was refluxed overnight. The precipitate was filtered off and washed with ethanol to afford intermediate 79-b (21 g, yield 52%).

Step 2: Synthesis of 5-methyl-6-vinylquinazolin-4-ol 15-c

A solution of intermediate 15-b (15.0 g, 52.4 mmol), potassium trifluoro(vinyl)borate (10.6 g, 79.0 mmol), Pd(dppf)$_2$Cl$_2$ (1.7 g, 2.6 mmol) and K$_2$CO$_3$ (21.74 g, 157.3 mmol) in EtOH (150 ml) was refluxed overnight. The solvent was evaporated under vacuum. The residue was treated with H$_2$O and CH$_2$Cl$_2$. The separated organic layer was dried over MgSO4, filtrated and evaporated under vacuum. The residue was purified by high-performance liquid chromatography over SYNERGI (eluent: TFA water/acetonitrile 30/70 v/v). The product fractions were collected and the organic solvent was evaporated. The pH was adjusted to 7 with saturated NaHCO$_3$. The aqueous concentrate was extracted with CH$_2$Cl$_2$. The separated organic layer was concentrated under vacuum to afford intermediate 15-c (3 g, yield 29%).

Step 3: Synthesis of 6-ethyl-5-methylquinazolin-4-ol 15-d

A solution of intermediate 15-c (3.0 g, 16 mmol) and HCl (11.5 ml) in MeOH (30 ml) was hydrogenated at room temperature (50 psi) with Pd/C (0.6 g) as a catalyst for 15 hours. After uptake of H$_2$ (32.50 mg, 16.11 mmol), the catalyst was filtered off and washed with methanol. The solvent was evaporated under vacuum to afford intermediate 15-d (2.1 g, yield 66%).

Step 4: Synthesis of 4-chloro-6-ethyl-5-methylquinazoline 15

A mixture of intermediate 15-d (1.80 g, 9.56 mmol), triethylamine (2.220 ml, 15.95 mmol) and phosphorus oxychloride (60 ml) was refluxed for 2 hours. The solvent was evaporated under vacuum. The residue was dissolved in ethyl acetate (200 ml) and the mixture was added drop wise into ice (200 g). The separated organic layer was washed successively with water (1×100 ml), 10% sodium bicarbonate aqueous solution (2×100 ml), water (1×100 ml) and brine (1×100 ml). The organic layer was dried (MgSO₄), filtered and the filtrate was concentrated under vacuum. The residue was purified by column chromatography over silica gel (eluent: petroleum ether/ethyl acetate 1/0 to 5/1) to give intermediate 15 (1.434 g, 68.94%).

¹H NMR (400 MHz, CDCl₃) δ ppm 1.27 (t, J=7.65 Hz, 3H) 2.88 (q, J=7.53 Hz, 2H) 2.94 (s, 3H) 7.75 (d, J=8.53 Hz, 1H) 7.87 (d, J=8.53 Hz, 1H) 8.89 (s, 1H)

Step 5: Synthesis of 4-(2-(1-(6-ethyl-5-methylquinazolin-4-yl)piperidin-2-yl)-5,6,7,8-tetrahydropyrazolo[5,1-b]quinazolin-9-yl)morpholine P13

To a solution of intermediate 8 (150 mg, 0.44 mmol) in 2-methoxyethanol (5 mL) 4-chloro-6-ethyl-5-methylquinazoline 15 (131 mg, 0.53 mmol, 1.2 eq.) and DIPEA (0.23 mL, 1.31 mmol, 3 eq.) were added. The mixture was stirred at 50° C. for 6 days. The reaction mixture was cooled to room temperature and poured into ice/water. The resulting milky solution was extracted with EtOAc two times. The combined organic layers were successively washed with water, brine, dried over magnesium sulfate and evaporated. The crude was purified on column with a gradient from pure DCM to DCM/MeOH (95/5). The product fraction was evaporated to give compound P13 as a white powder (70 mg, 100% pure, 31% yield).

LCMS (M+1)=512.

¹H NMR (420 K, 400 MHz, DMSO-d₆) δ ppm 1.19-1.33 (m, 3H) 1.63-1.94 (m, 8H) 2.16-2.41 (m, 2H) 2.80 (br. s., 9H) 3.37 (br. s., 4H) 3.50 (br. s., 1H) 3.73 (d, J=3.52 Hz, 5H) 5.32-6.47 (m, 2H) 7.54-7.60 (m, 2H) 8.41 (br. s., 1H).

Synthesis of N-(2-(2-(9-hydroxy-5,6,7,8-tetrahydropyrazolo[5,1-b]quinazolin-2-yl)-piperidine-1-carbonyl)-4-methylphenyl)methanesulfonamide P14

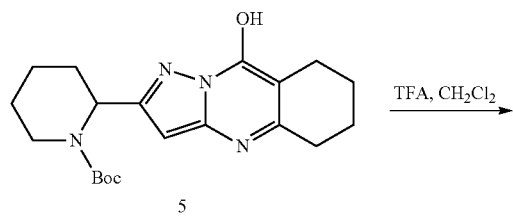

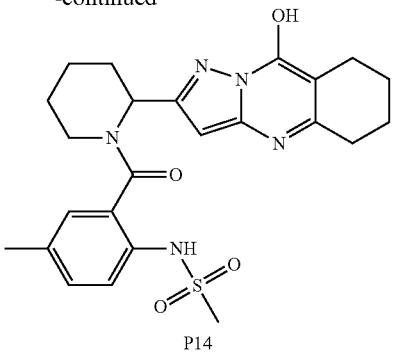

P14

Step 1: Synthesis of 2-(piperidin-2-yl)-5,6,7,8-tetrahydropyrazolo[5,1-b]quinazolin-9-ol 16

To a solution of intermediate 5 (500 mg, 1.34 mmol) in DCM (15 mL) was added TFA (0.51 mL, 6.7 mmol, 5 eq.) and the reaction stirred for 5 days. The reaction mixture was then evaporated in the vacuo and triturated in DIPE. The resulting precipitate was filtered to give pure targeted intermediate 16 (300 mg, 100% pure, 82% yield).

LCMS (M+1)=273.

Step 2: Synthesis of N-(2-(2-(9-hydroxy-5,6,7,8-tetrahydropyrazolo[5,1-b]quinazolin-2-yl)-piperidine-1-carbonyl)-4-methylphenyl)methanesulfonamide P14

To a solution of intermediate 16 (300 mg, 1.1 mmol) in DMF (8 mL), 2-(methanesulfonamido)-5-methyl-benzoic acid 9-a (303 mg, 1.32 mmol, 1.2 eq.), DIPEA (0.38 mL, 2.2 mmol, 2 eq.) and HATU (628 mg, 1.65 mmol, 1.5 eq.) were added. The mixture was stirred at room temperature for 2 hours then quenched with water. The resulting mixture was extracted with EtOAc twice. The combined organic layers were dried over magnesium sulfate and evaporated. The crude was purified by prep HPLC to give pure targeted compound P14 (70 mg, 100% pure, 13% yield).

LCMS (M+1)=484.

¹H NMR (420 K, 400 MHz, DMSO-d₆) δ ppm 1.54-1.80 (m, 8H) 1.88-2.00 (m, 1H) 2.21-2.31 (m, 4H) 2.45 (t, J=6.80 Hz, 2H) 2.60 (t, J=6.23 Hz, 2H) 3.04 (s, 3H) 3.11-3.23 (m, 1H) 3.84 (d, J=13.35 Hz, 1H) 5.54 (d, J=5.21 Hz, 1H) 5.86 (s, 1H) 7.14-7.23 (m, 2H) 7.33 (d, J=8.07 Hz, 1H) 8.22 (s, 1H) 11.23 (s, 1H).

Synthesis of N-(2-(2-(9-(dimethylamino)-5,6,7,8-tetrahydropyrazolo[5,1-b]quinazolin-2-yl)piperidine-1-carbonyl)-4-methylphenyl)methanesulfonamide P15

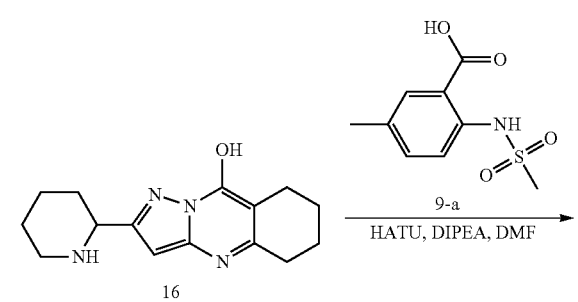

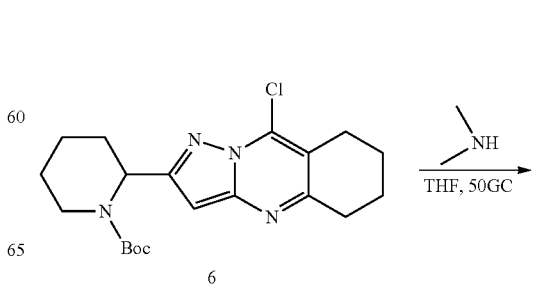

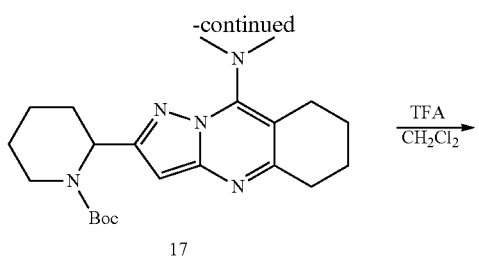

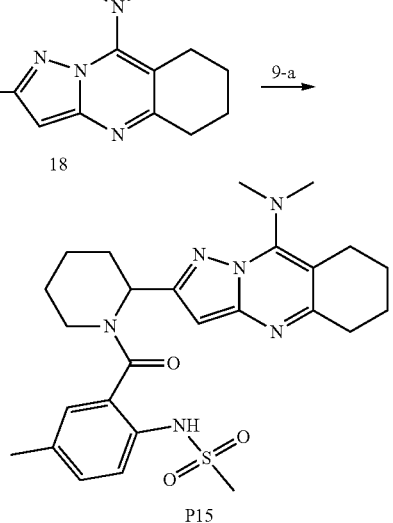

Step 1: Synthesis of tert-butyl 2-(9-(dimethyl-amino)-5,6,7,8-tetrahydropyrazolo[5,1-b]-quinazo-lin-2-yl)piperidine-1-carboxylate 17

To a solution of intermediate 6 (800 mg, 2.05 mmol) in THF (20 mL) dimethylamine (5.1 mL, 10.23 mmol, 5 eq.) was added. The reaction mixture was stirred at 50° C. during 1 week, then cooled to room temperature and evaporated in vacuo. The residue was dissolved in EtOAc and washed with water. The organic layer was dried over magnesium sulfate and evaporated. The crude was triturated in $Et_2O$ and evaporated in vacuo to give intermediate 17 (700 mg, 100% pure, 85% yield) as brown pale powder.

LCMS (M+1)=400.

$^1$H NMR (400 MHz, DMSO-$d_6$) δ ppm 1.34-1.44 (m, 11H) 1.55 (br. s., 2H) 1.69-1.84 (m, 5H) 2.27-2.35 (m, 1H) 2.69 (t, J=6.16 Hz, 2H) 2.80 (t, J=6.60 Hz, 2H) 2.84-2.93 (m, 1H) 3.08 (s, 6H) 3.83-3.93 (m, 1H) 5.34-5.43 (m, 1H) 6.06 (s, 1H).

Step 2: Synthesis of N,N-dimethyl-2-(piperidin-2-yl)-5,6,7,8-tetrahydropyrazolo[5,1-b]-quinazolin-9-amine 18

To a solution of intermediate 17 (100 mg, 0.25 mmol) in DCM (5 mL) TFA (0.115 mL, 1.5 mmol, 6 eq.) under inert atmosphere was added. The reaction mixture was stirred at room temperature during 2 days, then evaporated in vacuo. The residue was dissolved in water, basified with sodium carbonate and extracted 3 times with DCM.

The combined organic layers were dried over magnesium sulfate and evaporated in vacuo to give intermediate 18 (55 mg, 91% pure, 75% yield).

LCMS (M+1)=300.

$^1$H NMR (400 MHz, DMSO-$d_6$) δ ppm 1.44-1.62 (m, 4H) 1.67-1.75 (m, 2H) 1.76-1.84 (m, 3H) 1.88-1.99 (m, 1H) 2.69 (t, J=6.27 Hz, 2H) 2.73-2.77 (m, 1H) 2.80 (t, J=6.60 Hz, 2H) 3.03-3.07 (m, 1H) 3.09 (s, 6H) 3.79-3.91 (m, 1H) 6.26 (s, 1H).

Step 3: Synthesis of N-(2-(2-(9-(dimethylamino)-5,6,7,8-tetrahydropyrazolo[5,1-b]quinazolin-2-yl)piperidine-1-carbonyl)-4-methylphenyl)methanesulfonamide P15

To a solution of intermediate 18 (180 mg, 0.60 mmol) in dry DMF (4 mL) 2-(methanesulfonamido)-5-methyl-benzoic acid 9-a (165.4 mg, 0.721 mmol, 1.2 eq.), DIPEA (0.210 mL, 1.2 mmol, 2 eq.) and HATU (343 mg, 0.90 mmol, 1.5 eq.) were added. The reaction mixture was stirred at room temperature for overnight then quenched with water. The resulting mixture was further extracted with EtOAc and washed with brine (3×20 mL). The combined organics were dried over magnesium sulfate and concentrated in vacuo. The crude was purified on silica column with a gradient from pure DCM to DCM/MeOH (9/1) giving compound P15 (260 mg, 100% pure, 84% yield).

LCMS (M+1)=511.

$^1$H NMR (420 K, 400 MHz, DMSO-$d_6$) δ ppm 1.50-1.71 (m, 4H) 1.71-1.89 (m, 4H) 1.91-2.06 (m, 1H) 2.26 (s, 3H) 2.27-2.36 (m, 1H) 2.74 (t, J=6.34 Hz, 2H) 2.82 (t, J=6.63 Hz, 2H) 2.98 (s, 3H) 3.11 (s, 6H) 3.23 (m, J=13.30, 7.80, 7.80 Hz, 1H) 3.92 (d, J=13.39 Hz, 1H) 5.62 (d, J=5.59 Hz, 1H) 6.25 (s, 1H) 7.10-7.25 (m, 2H) 7.28-7.47 (m, 1H) 8.07 (br. s, 1H).

Synthesis of N,N-dimethyl-2-(1-(5-methylquinazo-lin-4-yl)piperidin-2-yl)-5,6,7,8-tetrahydropyrazolo[5,1-b]quinazolin-9-amine P16

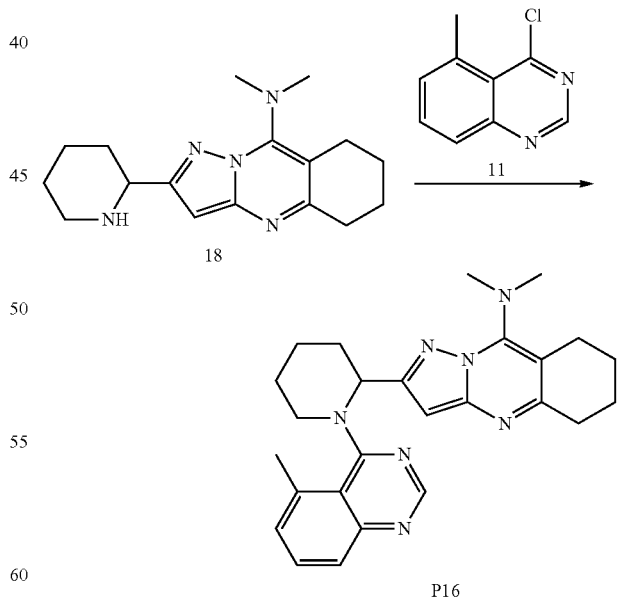

To a solution of intermediate 18 (369 mg, 1.23 mmol) in 2-methoxyethanol (10 mL), 4-chloro-5-methylquinazoline 11 (264 mg, 1.48 mmol, 1.2 eq.) and DIPEA (3 eq., 0.637 mL, 3.7 mmol) were added. The reaction mixture was stirred at 50° C. during 3 days, cooled to room temperature and poured into ice water. The resulting precipitate was filtered and the solid was purified on silica gel with a gradient from pure DCM to DCM/MeOH (9/1). The fraction was evaporated in vacuo, triturated in Et$_2$O and evaporated to dryness to give compound P16 (230 mg, 100% pure, 42% yield).

LCMS (M+1)=442.

$^1$H NMR (420 K, 400 MHz, DMSO-d$_6$) δ ppm 1.54-1.94 (m, 8H) 2.27 (br. s., 2H) 2.68 (br. s., 4H) 2.85 (br. s., 3H) 2.96 (br. s., 6H) 3.50 (br. s., 2H) 5.60-5.68 (m, 1H) 6.01 (br. s., 1H) 7.30 (d, J=6.16 Hz, 1H) 7.52-7.65 (m, 2H) 8.46 (br. s., 1H).

Synthesis of N-(4-methyl-2-(2-(5,6,7,8-tetrahydropyrazolo[5,1-b]quinazolin-2-yl)-piperidine-1-carbonyl)phenyl)methanesulfonamide P17

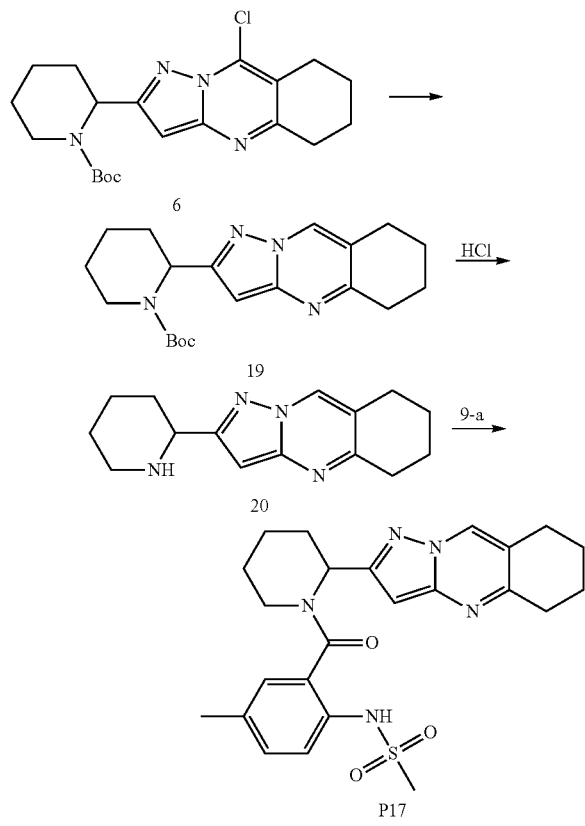

Step 1: Synthesis of tert-butyl 2-(5,6,7,8-tetrahydropyrazolo[5,1-b]quinazolin-2-yl)piperidine-1-carboxylate 19

To a solution of intermediate 6 (1 g, 1.54 mmol) in DMF (10 mL) in a sealed tube were added sodium formate (208 mg, 3 mmol, 12 eq.) and palladium tetrakis (117 mg, 0.15 mmol, 0.1 eq.). The mixture was heated to 140° C. during 50 minutes under microwave then filtrated over dicalite rinsed with EtOAc. The organic layer was washed with a saturated solution of NaHCO$_3$ followed by brine, then dried over magnesium sulfate and evaporated in the vacuo. The crude was purified on silica column with a gradient from pure DCM to DCM/MeOH (95/5), the product fraction was collected and evaporated to dryness giving a white powder as desired intermediate 19 (438 mg, 100% pure, 80% yield).

LCMS (M+1)=357

$^1$H NMR (400 MHz, DMSO-d$_6$) δ ppm 1.32-1.45 (m, 11H) 1.51-1.60 (m, 2H) 1.71-1.89 (m, 5H) 2.31 (d, J=13.20 Hz, 1H) 2.76 (t, J=6.16 Hz, 2H) 2.84 (t, J=6.49 Hz, 3H) 3.91 (d, J=12.76 Hz, 1H) 5.43 (br. s., 1H) 6.18 (s, 1H) 8.77 (s, 1H).

Step 2: Synthesis of 2-(piperidin-2-yl)-5,6,7,8-tetrahydropyrazolo[5,1-b]quinazoline 20

Intermediate 19 (438 mg, 1.23 mmol) was dissolved in HCl (4 M) solution in 1,4-dioxane (10 mL) and the mixture stirred at room temperature for 1 hour. The reaction mixture was then poured into an iced saturated solution of Na$_2$CO$_3$ and extracted DCM (3×50 mL). The combined organics were dried over magnesium sulfate and evaporated in vacuo giving intermediate 20 (300 mg, 100% pure, 95% yield). The crude was used as such for the next step.

LCMS (M+1)=257.

Step 3: Synthesis of N-(4-methyl-2-(2-(5,6,7,8-tetrahydropyrazolo[5,1-b]quinazolin-2-yl)-piperidine-1-carbonyl)phenyl)methanesulfonamide P17

To a solution of intermediate 20 (150 mg, 0.59 mmol) in DMF (5 mL), 2-(methanesulfonamido)-5-methyl-benzoic acid 9-a (161 mg, 0.7 mmol, 1.2 eq.), DIPEA (0.20 mL, 1.17 mmol, 2 eq.) and HATU (334 mg, 0.89 mmol 1.5 eq.) were added. The reaction mixture was stirred at room temperature for 1 hour then quenched with water and extracted with EtOAc (2×50 mL). The combined organics were washed with brine (3×50 mL), dried over magnesium sulfate and evaporated in vacuo. The crude was purified on column with a gradient from pure DCM to DCM/MeOH (95/5). The fraction was evaporated in vacuo to yield compound P17 (194 mg, 100% pure, 70% yield) as a pale yellow powder.

LCMS (M+1)=468.

$^1$H NMR (420K, 400 MHz, DMSO-d$_6$) δ ppm 1.51-2.06 (m, 9H) 2.33 (s, 4H) 2.81 (d, J=5.94 Hz, 2H) 2.86-2.93 (m, 2H) 3.01 (s, 3H) 3.09 (br. s., 1H) 3.76 (br. s., 1H) 5.75 (br. s., 1H) 6.43 (s, 1H) 7.08-7.27 (m, 2H) 7.31-7.46 (m, 1H) 8.54 (br. s., 1H) 8.68 (s, 1H).

Synthesis of 2-(1-(5-methylquinazolin-4-yl)piperidin-2-yl)-5,6,7,8-tetrahydropyrazolo-[5,1-b]quinazoline P18

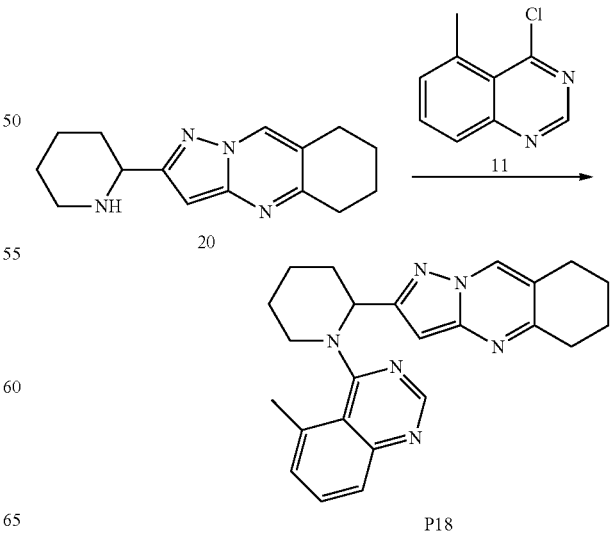

To a solution of intermediate 20 (150 mg, 0.59 mmol) in 2-methoxyethanol (5 mL), 4-chloro-5-methylquinazoline 11 (170 mg, 0.89 mmol, 1.5 eq.) and DIPEA (0.300 mL, 1.76 mmol, 3 eq.) were added. The mixture was stirred at 50° C. for 1 day then cooled to room temperature and poured into an iced saturated solution of NaHCO₃. The resulting mixture was further extracted with DCM (2×50 mL). The combined organics were dried over magnesium sulfate and evaporated in vacuo. The crude was purified on column with a gradient from pure DCM to DCM/MeOH (95/5). The product fraction was evaporated in vacuo giving the targeted compound P18 as a slightly yellow powder (194 mg, 100% pure, 84% yield).

LCMS (M+1)=399.

$^1$H NMR (420 K, 400 MHz, DMSO-$d_6$) δ ppm 1.49-1.89 (m, 8H) 2.15-2.32 (m, 2H) 2.71-2.76 (m, 2H) 2.80 (t, J=6.60 Hz, 2H) 2.84 (s, 3H) 3.45-3.55 (m, 2H) 5.56-5.70 (m, 1H) 6.08 (br. s., 1H) 7.23-7.36 (m, 1H) 7.55-7.64 (m, 2H) 8.40-8.52 (m, 2H).

Synthesis of N-(2-(2-(9-amino-5,6,7,8-tetrahydropyrazolo[5,1-b]quinazolin-2-yl)-piperidine-1-carbonyl)-4-methylphenyl)methanesulfonamide P19

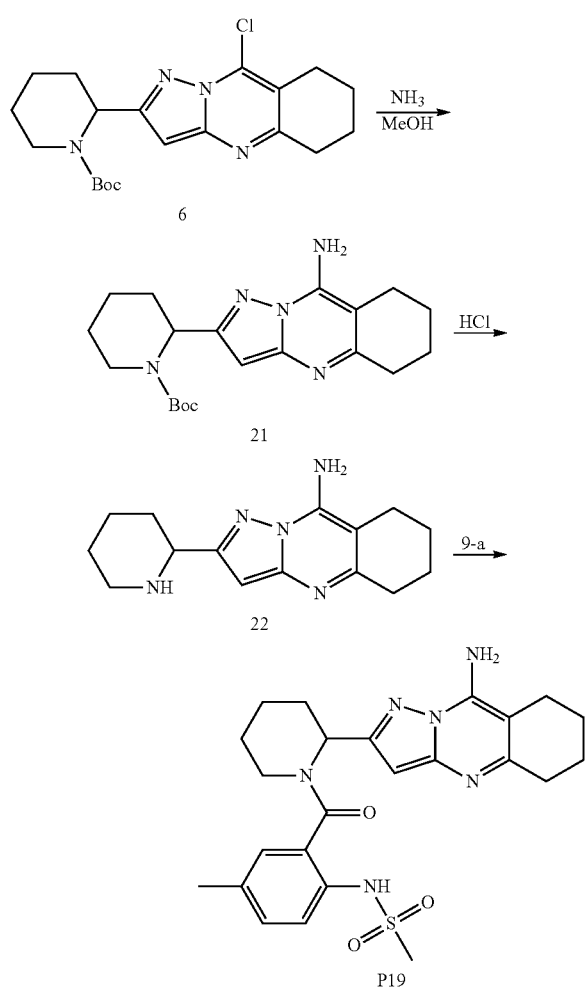

Step 1: tert-butyl 2-(9-amino-5,6,7,8-tetrahydropyrazolo[5,1-b]quinazolin-2-yl)piperidine-1-carboxylate 21

Intermediate 6 (500 mg, 1.13 mmol) was dissolved in ammonia (7M) in MeOH (10 mL) in a sealed tube. The resulting mixture was heated at 100° C. for 18 hours. The reaction mixture was then cooled to room temperature and evaporated in vacuo. The crude was directly purified on column with a gradient from pure DCM to DCM/MeOH (95/5). The product fraction was evaporated to give pure intermediate 21 as a white powder (120 mg, 100% pure, 28% yield).

LCMS (M+1)=372.

$^1$H NMR (400 MHz, DMSO-$d_6$) δ ppm 1.35-1.44 (m, 11H) 1.56 (d, J=8.80 Hz, 2H) 1.77 (d, J=2.86 Hz, 5H) 2.31-2.44 (m, 1H) 2.51-2.53 (m, 2H) 2.62-2.74 (m, 2H) 2.77-3.00 (m, 1H) 3.85-3.96 (m, 1H) 5.38 (br. s., 1H) 5.85 (s, 1H) 7.26 (br. s., 2H)

Step 2: Synthesis of 2-(piperidin-2-yl)-5,6,7,8-tetrahydropyrazolo[5,1-b]quinazolin-9-amine 22

Intermediate 21 (120 mg, 0.32 mmol) was dissolved in HCl (4M) solution in 1,4-dioxane (5 mL) and stirred at room temperature for 30 minutes. The reaction mixture was then poured into an iced saturated solution of Na₂CO₃ and extracted with DCM (3×15 mL). The combined organics were dried over magnesium sulfate and evaporated in vacuo to give the desired intermediate 22 as a sticky solid (80 mg, 100% pure, 91% yield).

LCMS (M+1)=272.

Step 3: Synthesis of N-(2-(2-(9-amino-5,6,7,8-tetrahydropyrazolo[5,1-b]quinazolin-2-yl)-piperidine-1-carbonyl)-4-methylphenyl)methanesulfonamide P19

To a solution of intermediate 22 (80 mg, 0.3 mmol) in DMF (3 mL), 2-(methanesulfonamido)-5-methyl-benzoic acid 9-a (81 mg, 0.35 mmol, 1.2 eq.), DIPEA (0.102 mL, 0.59 mmol, 2 eq.) and HATU (168 mg, 0.44 mmol, 1.5 eq.) were added. The mixture was stirred at room temperature for 1 hour and quenched with water. The resulting mixture was extracted with EtOAc and the combined organics were washed with brine (3×15 mL), dried over magnesium sulfate and evaporated in vacuo. The crude was purified on column with a gradient from pure DCM to DCM/MeOH (95/5). The product fraction was evaporated to give targeted compound P19 as a white powder (62 mg, 100% pure, 43% yield).

LCMS (M+1)=483.

$^1$H NMR (405 K, 400 MHz, DMSO-$d_6$) δ ppm 1.58-1.72 (m, 4H) 1.82-1.86 (m, 4H) 1.93-2.02 (m, 1H) 2.31 (s, 3H) 2.37 (br. s., 1H) 2.58-2.64 (m, 2H) 2.74-2.77 (m, 2H) 3.02 (s, 3H) 3.12-3.21 (m, 1H) 3.93 (br. s., 1H) 5.59 (br. s., 1H) 6.10-6.17 (m, 1H) 6.81 (br. s., 2H) 7.21-7.26 (m, 2H) 7.36 (d, J=8.14 Hz, 1H) 7.87-8.97 (m, 1H).

39

Synthesis of N-(4-methyl-2-(2-(8-morpholino-6,7-dihydro-5H-cyclopenta[d]pyrazolo-[1,5-a]pyrimidin-2-yl)piperidine-1-carbonyl)phenyl)methanesulfonamide P20

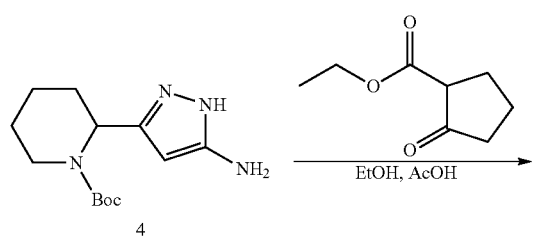

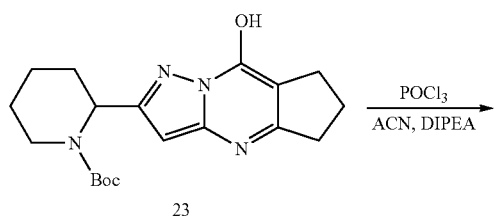

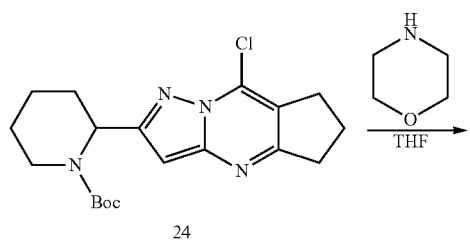

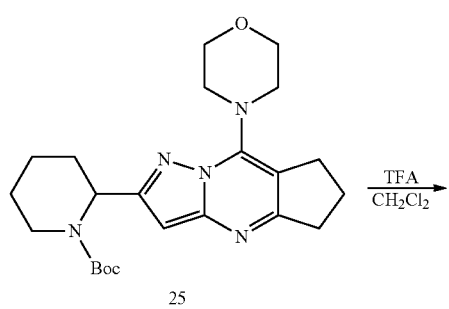

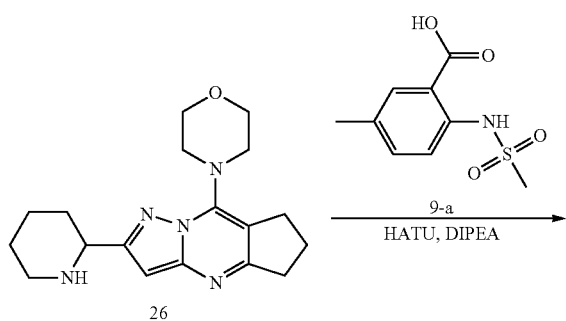

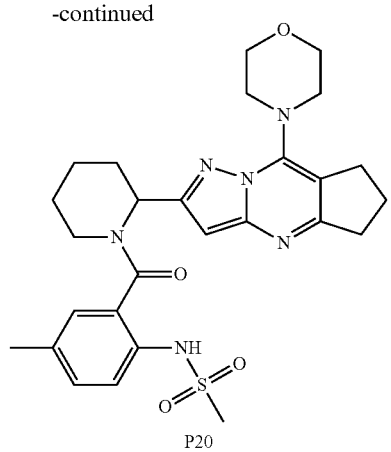

P20

Step 1: Synthesis of tert-butyl 2-(8-hydroxy-6,7-dihydro-5H-cyclopenta[d]-pyrazolo[1,5-a]-pyrimidin-2-yl)piperidine-1-carboxylate 23

To a solution of intermediate 4 (2 g, 7.2 mmol) in ethanol (100 mL) was added ethyl-2-oxo-cyclopentanecarboxylate (2 eq., 2.14 mL, 14.5 mmol) and acetic acid (10 eq., 4.2 mL, 72 mmol) at room temperature. The solution was heated at reflux during 16 hours. The solution was then cooled to ambient temperature and concentrated in vacuo. The crude was taken up in diisopropylether (50 mL) and stirred for 1 hour at room temperature. The solid was filtered off and dried into the oven to give intermediate 23 (2.45 g, 94%) as a white solid.

LCMS m/z=359 (M+H)$^+$ $^1$H NMR (400 MHz, DMSO-d$_6$) δ ppm 1.31-1.48 (m, 11H) 1.49-1.63 (m, 2H) 1.63-1.77 (m, 1H) 2.00-2.13 (m, 2H) 2.31 (d, J=13.42 Hz, 1H) 2.67 (t, J=7.26 Hz, 2H) 2.73-2.84 (m, 1H) 2.90 (t, J=7.70 Hz, 2H) 3.89 (d, J=13.42 Hz, 1H) 5.18-5.39 (m, 1H) 5.77 (s, 1H)

Step 2: Synthesis of tert-butyl 2-(8-chloro-6,7-dihydro-5H-cyclopenta[d]pyrazolo[1,5-a]-pyrimidin-2-yl)piperidine-1-carboxylate 24

To a solution of intermediate 23 (2.03 g, 5.6 mmol) in acetonitrile (50 mL) was added DIPEA (5 eq., 4.8 mL, 28.3 mmol) and the solution was stirred for 10 minutes at 70° C. under inert atmosphere. Then POCl$_3$ (3 eq., 1.6 mL, 17 mmol) was added dropwise to the solution and the reaction mixture was stirred for 16 hours at 70° C. After cooling to room temperature, the crude was co-evaporated twice with toluene. The crude was then taken up with a cooled saturated aqueous solution of NaHCO$_3$. The resulting mixture was stirred for 10 minutes. The solution was further extracted with dichloromethane and the combined organics were dried over MgSO$_4$ and concentrated to yield intermediate 24 (2.1 g, 98% yield).

LCMS m/z=377 (M+H)$^+$

Step 3: Synthesis of tert-butyl 2-(8-morpholino-6,7-dihydro-5H-cyclopenta[d]-pyrazolo-[1,5-a]pyrimidin-2-yl)piperidine-1-carboxylate 25

To a solution of intermediate 24 (1.3 g, 3.45 mmol) in THF (60 mL) was added morpholine (5 eq., 1.5 mL, 17.24 mmol) and the solution was heated at 50° C. After 3 hours the solution was concentrated in vacuo and diluted with ethylacetate and washed with a NaHCO$_3$ (aq.) solution. The combined organics were dried over MgSO$_4$, filtered off and concentrated in vacuo. The crude was purified by column chromatography eluting with a gradient starting from 0% to 10% MeOH and DCM giving intermediate 25 (1.06 g, 70%) as a dark oil which was used as such into the next step.

LCMS m/z=428 (M+H)$^+$

Step 4: Synthesis of 4-(2-(piperidin-2-yl)-6,7-dihydro-5H-cyclopenta[d]pyrazolo[1,5-a]-pyrimidin-8-yl)morpholine 26

To a solution of intermediate 25 (1.06 g, 2.47 mmol) in DCM (25 mL) was added TFA (3 eq., 0.57 mL, 7.4 mmol) at room temperature. The solution was stirred for 16 hours at room temperature. After concentration in vacuo the crude was diluted with a cooled saturated aqueous solution of Na$_2$CO$_3$ and extracted three times with DCM. The combined organics were dried with MgSO$_4$ and concentrated in vacuo to give intermediate 26 (740 mg, 82%, 90% pure) which was used as such into the next step.

LCMS m/z=328 (M+H)$^+$

Step 5: Synthesis of N-(4-methyl-2-(2-(8-morpholino-6,7-dihydro-5H-cyclopenta[d]-pyrazolo[1,5-a]pyrimidin-2-yl)piperidine-1-carbonyl)phenyl)methanesulfonamide P20

To a solution of intermediate 26 (124 mg, 0.37 mmol) in DMF (4 mL) was added DIPEA (1.5 eq., 0.1 mL, 0.57 mmol), 5-methyl-2-[(methylsulfonyl)amino]benzoic acid 9-a (1.2 eq., 104 mg, 0.45 mmol) and HATU (2 eq., 288 mg, 0.76 mmol) at room temperature. The solution was stirred for overnight at room temperature. The water was added and the solid was filtered off and washed with water. The solid was dissolved in MeOH and further purified on HPLC to give compound P20 (53 mg, 26%).

LCMS m/z=539 (M+H)$^+$ $^1$H NMR (400 MHz, DMSO-d$_6$) δ ppm 1.54-1.70 (m, 4H) 1.98 (td, J=14.43, 6.83 Hz, 1H) 2.09 (quin, J=7.47 Hz, 2H) 2.23-2.32 (m, 4H) 2.83 (t, J=7.73 Hz, 2H) 2.96 (s, 3H) 3.06 (t, J=7.24 Hz, 2H) 3.17-3.31 (m, 1H) 3.61-3.71 (m, 4H) 3.77-3.82 (m, 4H) 3.91 (d, J=14.13 Hz, 1H) 5.61 (m, J=4.04 Hz, 1H) 6.23 (s, 1H) 7.14 (d, J=2.13 Hz, 1H) 7.19 (dd, J=7.94, 1.55 Hz, 1H) 7.34 (d, J=8.07 Hz, 1H) 8.07 (br. s., 1H)

Synthesis of 4-(2-(1-(5-methylquinazolin-4-yl)piperidin-2-yl)-6,7-dihydro-5H-cyclopenta[d]pyrazolo[1,5-a]pyrimidin-8-yl)morpholine P21

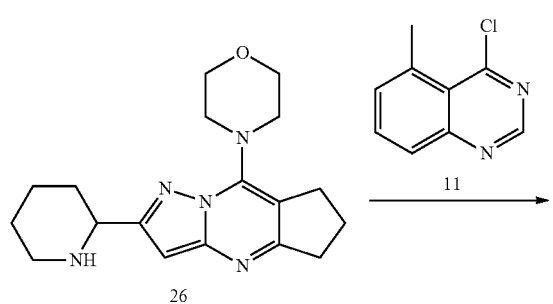

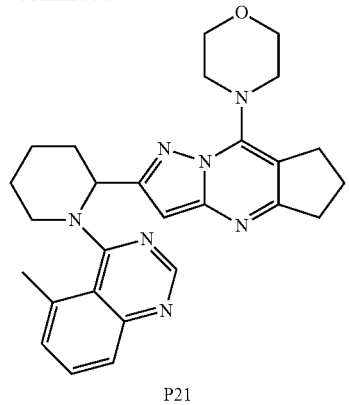

P21

To a solution of intermediate 26 (190 mg, 0.52 mmol) in 2-methoxyethanol (10 mL) was added 4-chloro-5-methylquinazoline 11 (1.31 eq. 128.5 mg, 0.68 mmol) and DIPEA (3 eq., 0.27 mL, 1.56 mmol). The solution was heated at 80° C. during 48 hours. After concentration in vacuo, the crude was purified on HPLC to give compound P21 (56 mg, 23%) as a white solid.

LCMS m/z=470 (M+H)$^+$ $^1$H NMR (400 MHz, DMSO-d$_6$) δ ppm 1.52-1.65 (m, 1H) 1.66-1.76 (m, 2H) 1.83-1.96 (m, 1H) 2.01-2.13 (m, 2H) 2.20-2.33 (m, 2H) 2.80 (t, J=7.70 Hz, 2H) 2.87 (s, 3H) 3.04 (t, J=7.15 Hz, 2H) 3.48-3.62 (m, 6H) 3.67-3.75 (m, 4H) 5.46-5.64 (m, 1H) 6.00 (br. s, 1H) 7.28-7.38 (m, 1H) 7.56-7.67 (m, 2H) 8.48 (s, 1H)

Synthesis of 2-(1-(5-methylquinazolin-4-yl)piperidin-2-yl)-8-(pyrrolidin-1-yl)-6,7-dihydro-5H-cyclopenta[d]pyrazolo[1,5-a]pyrimidine P22

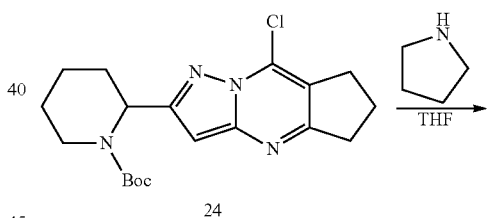

24

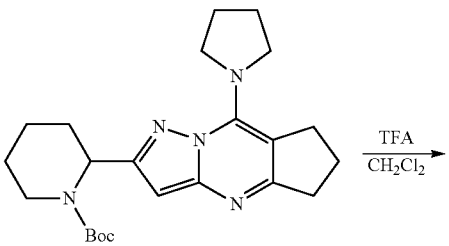

27

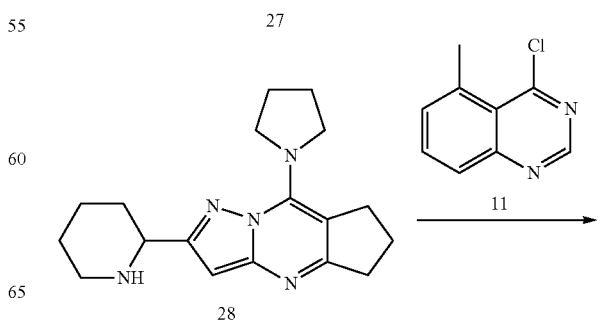

28

8H) 3.53-4.23 (m, 5H) 5.22-6.39 (m, 2H) 7.21-7.26 (m, 1H) 7.52-7.73 (m, 2H) 8.51-8.64 (m, 1H)

Synthesis of N-(4-methyl-2-(2-(10-morpholino-6,7,8,9-tetrahydro-5H-cyclohepta[d]-pyrazolo[1,5-a]pyrimidin-2-yl)piperidine-1-carbonyl)phenyl)-methanesulfonamide P23

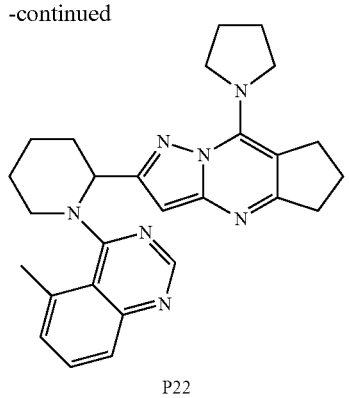

P22

Step 1: Synthesis of tert-butyl 2-(8-(pyrrolidin-1-yl)-6,7-dihydro-5H-cyclopenta[d]-pyrazolo[1,5-a]pyrimidin-2-yl)piperidine-1-carboxylate 27

To a solution of intermediate 24 (800 mg, 2.1 mmol) in THF (60 mL) was added pyrrolidine (5 eq., 0.87 mL, 10.6 mmol). The solution was stirred for 3 hours at room temperature. After evaporation the crude was extracted with EtOAc and washed with saturated NaHCO₃ solution. The combined organics were dried with MgSO₄, filtered off and concentrated in vacuo. The crude was purified by column chromatography eluting with a gradient starting from 0% to 10% MeOH and DCM to give intermediate 27 (550 mg, 61%) as a dark oil which was used as such into the next step.
LCMS m/z=412 (M+H)⁺

Step 2: Synthesis of 2-(piperidin-2-yl)-8-(pyrrolidin-1-yl)-6,7-dihydro-5H-cyclopenta[d]-pyrazolo[1,5-a]pyrimidine 28

To a solution of intermediate 27 (520 mg, 1.22 mmol) in DCM (20 mL) TFA (6 eq., 0.56 mL, 7.35 mmol) was added. The solution was stirred at room temperature for 16 hours. The reaction mixture was concentrated in vacuo. To the resulting residue a saturated aqueous solution of NaHCO₃ was added. The resulting mixture was extracted with DCM. The combined organics were collected, dried with MgSO₄ and evaporated to give intermediate 28 (260 mg, 68%, 86% pure) which was used as such into the next step.
LCMS m/z=312 (M+H)⁺

Step 3: Synthesis of 2-(1-(5-methylquinazolin-4-yl)piperidin-2-yl)-8-(pyrrolidin-1-yl)-6,7-dihydro-5H-cyclopenta[d]pyrazolo[1,5-a]pyrimidine P22

To a solution of intermediate 28 (250 mg, 0.80 mmol) in 2-methoxyethanol (40 mL) was added intermediate 11 (1.5 eq., 226 mg, 1.20 mmol) and DIPEA (3 eq., 0.415 mL, 2.4 mmol). The solution was stirred at 50° C. for 48 hours. The mixture was then concentrated in vacuo, extracted with DCM and washed with a saturated aqueous solution of NaHCO₃. The combined organics were dried over MgSO₄, filtered off and concentrated in vacuo. The crude was purified by HPLC to yield compound P22 (170 mg, 45%).
LCMS m/z=454 (M+H)⁺
¹H NMR (400 MHz, CHLOROFORM-d) δ ppm 1.24-1.37 (m, 1H) 1.41-1.55 (m, 1H) 1.60-1.67 (m, 1H) 1.85-1.97 (m, 5H) 1.97-2.15 (m, 2H) 2.15-2.48 (m, 2H) 2.70-3.44 (m,

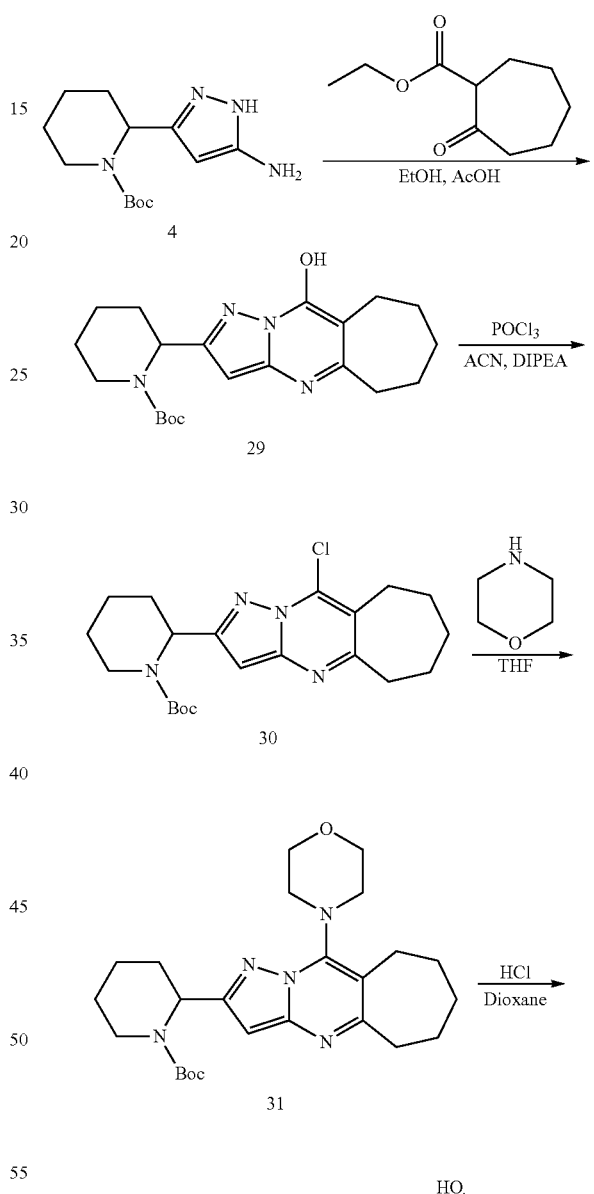

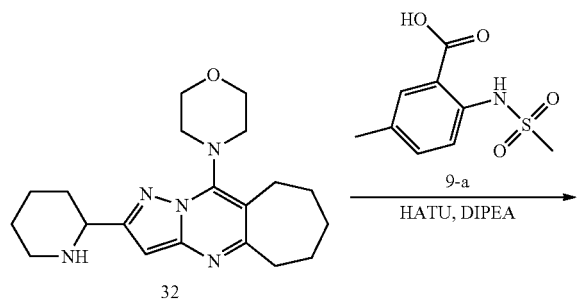

-continued

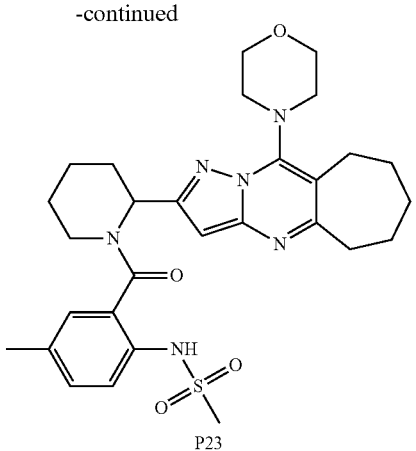

P23

Step 1: Synthesis of tert-butyl 2-(10-hydroxy-6,7,8,9-tetrahydro-5H-cyclohepta[d]-pyrazolo[1,5-a]pyrimidin-2-yl)piperidine-1-carboxylate 29

To a solution of intermediate 4 (500 mg, 1.87 mmol) in EtOH (25 mL) ethyl 2-oxocyclo-heptanecarboxylate (0.66 mL, 3.74 mmol, 2 eq.) and AcOH (1 mL, 18.70 mmol, 10 eq.) were added. The resulting mixture was stirred at reflux for 3 hours. The reaction mixture was then evaporated in vacuo and triturated in DIPE. The resulting precipitate was filtered to give intermediate 29 (650 mg, 100% pure, 90% yield) as a white powder.

LCMS (M+1)=387.

$^1$H NMR (400 MHz, DMSO-d$_6$) δ ppm 1.35-1.45 (m, 11H) 1.46-1.52 (m, 2H) 1.52-1.60 (m, 2H) 1.61-1.83 (m, 5H) 2.32 (d, J=12.32 Hz, 1H) 2.62-2.86 (m, 5H) 3.90 (d, J=12.76 Hz, 1H) 5.31 (br. s., 1H) 5.74 (s, 1H) 11.80-12.12 (m, 1H).

Step 2: Synthesis of tert-butyl 2-(10-chloro-6,7,8,9-tetrahydro-5H-cyclohepta[d]pyrazolo-[1,5-a]pyrimidin-2-yl)piperidine-1-carboxylate 30

To a solution of intermediate 29 (550 mg, 1.42 mmol) in ACN (15 mL), DIPEA (1.23 mL, 7.12 mmol, 5 eq.) and POCl$_3$ (0.4 mL, 4.27 mmol, 3 eq.) were added. The reaction mixture was stirred at 70° C. during 1 day then cooled to room temperature and co-evaporated with toluene two times. The residue was dissolved in a minimum amount of ACN and poured in an ice saturated solution of NaHCO$_3$. The product was extracted with DCM (2×20 mL). The combined organic layers were dried over magnesium sulfate and evaporated in vacuo to give intermediate 30 (570 mg, 100% pure, 98% yield).

LCMS (M+1)=405.

Step 3: Synthesis of tert-butyl 2-(10-morpholino-6,7,8,9-tetrahydro-5H-cyclohepta[d]-pyrazolo[1,5-a]pyrimidin-2-yl)piperidine-1-carboxylate 31

To a solution of intermediate 30 (570 mg, 1.41 mmol) in THF (15 mL) was added morpholine (5 eq., 0.62 mL, 7.04 mmol). The reaction mixture was stirred at 50° C. for 5 days then cooled to room temperature. The residue was triturated in water and stirred for 2 hours. The precipitate was filtered to give intermediate 31 (600 mg, 91% pure, 94% yield) as a pale brown powder.

LCMS (M+1)=456.

$^1$H NMR (400 MHz, DMSO-d$_6$) δ ppm 1.34-1.46 (m, 11H) 1.56 (d, J=7.92 Hz, 2H) 1.66 (br. s., 4H) 1.78 (d, J=5.06 Hz, 3H) 2.25-2.35 (m, 1H) 2.79-2.88 (m, 3H) 2.90-2.97 (m, 2H) 3.42 (br. s., 4H) 3.70-3.80 (m, 4H) 3.87-3.95 (m, 1H) 5.42 (br. s, 1H) 6.19 (s, 1H).

Step 4: Synthesis of 4-(2-(piperidin-2-yl)-6,7,8,9-tetrahydro-5H-cyclohepta[d]-pyrazolo-[1,5-a]pyrimidin-10-yl)morpholine 32

Intermediate 31 (500 mg, 1.1 mmol) was dissolved in solution of HCl (4 M) in 1,4 dioxane (25 mL) and the mixture was stirred for 1 hour at room temperature. The reaction mixture was then poured into a saturated solution of Na$_2$CO$_3$ and extracted with DCM (3×20 mL). The combined organic layers were dried over magnesium sulfate and evaporated in vacuo giving intermediate 32 (290 mg, 84% pure, 62% yield). The crude was used as such for the next step.

LCMS (M=1) 356.

Step 5: Synthesis of N-(4-methyl-2-(2-(10-morpholino-6,7,8,9-tetrahydro-5H-cyclohepta[d]-pyrazolo[1,5-a]pyrimidin-2-yl)piperidine-1-carbonyl)phenyl)-methanesulfonamide P23

To a solution of intermediate 32 (120 mg, 0.34 mmol) in DMF (3 mL), 2-(methanesulfonamido)-5-methyl-benzoic acid 9-a (93 mg, 0.41 mmol, 1.2 eq.), DIPEA (0.12 mL, 0.68 mmol, 2 eq.) and HATU (193 mg, 0.51 mmol, 1.5 eq.) were added. The reaction mixture was stirred at room temperature for 1 hour, and then quenched with water. The resulting precipitate was stirred for 1 night then filtered. The filtrate was extracted with EtOAc and the organic layer was dried over magnesium sulfate and evaporated. The solids were gathered and purified on column with a gradient from, pure DCM to DCM/MeOH (9/1) to give the desired compound P23 (88 mg, 100% pure, 46% yield).

LCMS (M+1)=567.

$^1$H NMR (420 K, 400 MHz, DMSO-d$_6$) δ ppm 1.52-1.90 (m, 10H) 1.93-2.12 (m, 1H) 2.21-2.41 (m, 4H) 2.86-3.09 (m, 7H) 3.15-3.37 (m, 1H) 3.38-3.55 (m, 4H) 3.77-3.87 (m, 4H) 3.93 (d, J=13.71 Hz, 1H) 5.69 (s, 1H) 6.36 (s, 1H) 7.14-7.28 (m, 2H) 7.30-7.48 (m, 1H) 8.17 (br. s, 1H).

Synthesis of 4-(2-(1-(5-methylquinazolin-4-yl)piperidin-2-yl)-6,7,8,9-tetrahydro-5H-cyclohepta[d]pyrazolo[1,5-a]pyrimidin-10-yl)morpholine P24

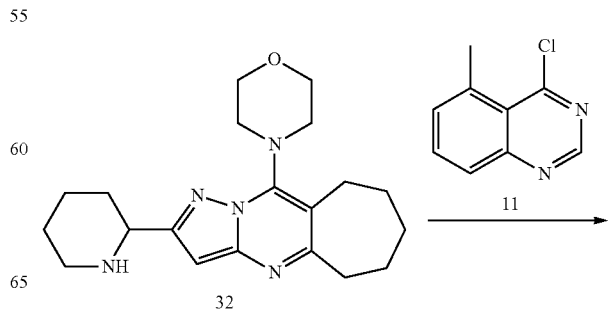

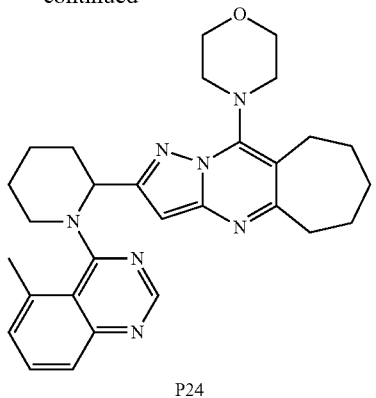

P24

To a solution of intermediate 32 (290 mg, 0.65 mmol) in 2-methoxyethanol (15 mL) 4-chloro-5-methylquinazoline 11 (153 mg, 0.78 mmol, 1.2 eq.) and DIPEA (0.34 mL, 1.96 mmol, 3 eq.) were added. The reaction mixture was stirred at 50° C. for 5 days then cooled to room temperature and poured into ice/water. The mixture was extracted with DCM and EtOAc. The combined organic layers were dried over magnesium sulfate and evaporated. The residue was then recrystallized in ACN to give compound P24 (80 mg, 100% pure, 24% yield).

LCMS (M+1)=498.

$^1$H NMR (420 K, 400 MHz, DMSO-d$_6$) δ ppm 1.65-1.93 (m, 10H) 2.24-2.37 (m, 2H) 2.88-2.90 (m, 4H) 2.93-2.97 (m, 2H) 3.26-3.36 (m, 4H) 3.48-3.63 (m, 2H) 3.68-3.77 (m, 5H) 5.55-5.70 (m, 1H) 6.11 (br. s, 1H) 7.27-7.39 (m, 1H) 7.56-7.70 (m, 2H) 8.50 (s, 1H).

Synthesis of N-(4-methyl-2-(2-(8-morpholino-5,7-dihydrofuro[3,4-d]pyrazolo[1,5-a]-pyrimidin-2-yl) piperidine-1-carbonyl)phenyl)methanesulfonamide P25

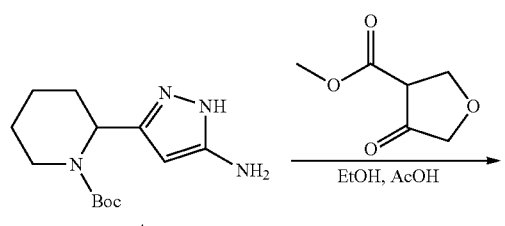

4

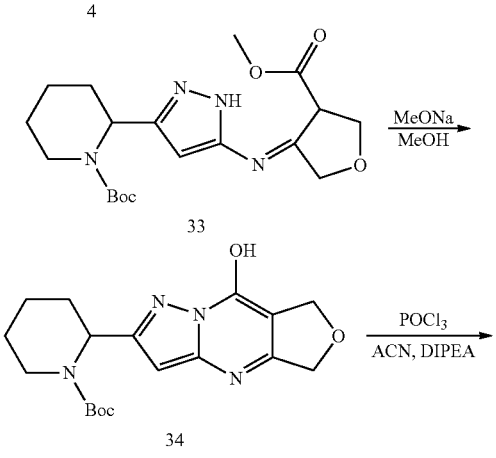

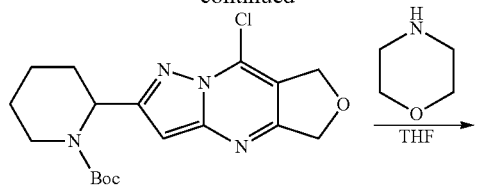

35

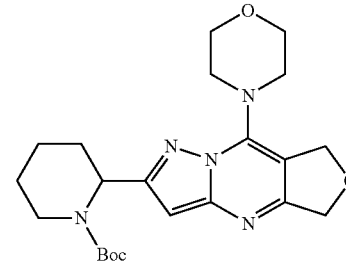

36

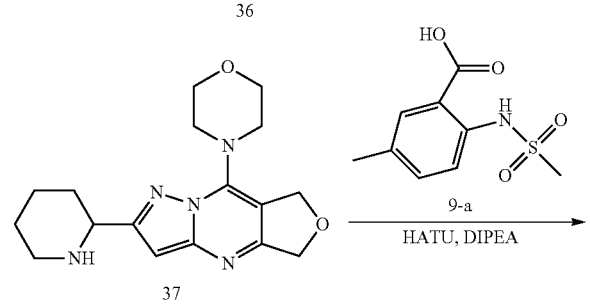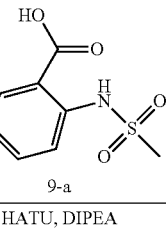

37

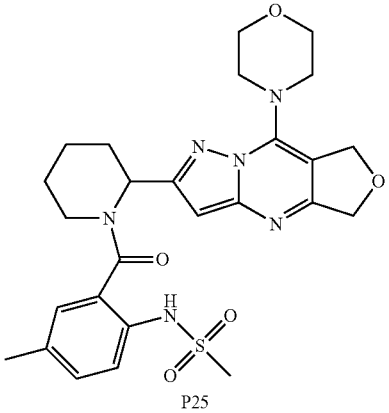

P25

Step 1: Synthesis of (E)-tert-butyl 2-(5-((4-(methoxycarbonyl)dihydrofuran-3(2H)-ylidene) amino)-1H-pyrazol-3-yl)piperidine-1-carboxylate 33

To a solution of intermediate 4 (500 mg, 1.87 mmol) in EtOH (25 mL), methyl 4-oxotetrahydrofuran-3-carboxylate (0.54 mg, 3.74 mmol, 2 eq.) and AcOH (1.07 mL, 18.7 mmol, 10 eq.) were added. The mixture was stirred at reflux during two hours then cooled to room temperature. The reaction mixture was evaporated in vacuo and the residue was poured into a saturated solution of NaHCO$_3$. The resulting mixture was extracted with EtOAc (3×50 mL). The combined organics were dried over magnesium sulfate and evaporated in the vacuo giving targeted intermediate 33 (700 mg, 100% pure, 95% yield).

LCMS (M+1)=393.

Step 2: Synthesis of tert-butyl 2-(8-hydroxy-5,7-dihydrofuro[3,4-d]pyrazolo[1,5-a]pyrimidin-2-yl)piperidine-1-carboxylate 34

To a solution of intermediate 33 (700 mg, 1.78 mmol) in EtOH (15 mL) NaOMe (30%) solution in MeOH (1 mL) was added. The mixture was stirred at room temperature for 1 hour. The reaction mixture was then evaporated in vacuo and triturated in DIPE. The resulting precipitate was filtered to give pure targeted intermediate 34 (640 mg, 100% pure, 99% yield) as a white powder.

LCMS (M+1)=361.

$^1$H NMR (400 MHz, DMSO-$d_6$) δ ppm 1.33-1.39 (m, 2H) 1.41 (s, 9H) 1.55 (br. s., 2H) 1.71 (d, J=5.28 Hz, 1H) 2.31 (d, J=12.98 Hz, 1H) 2.72-2.87 (m, 1H) 3.90 (d, J=13.20 Hz, 1H) 4.88-4.93 (m, 2H) 4.95-5.00 (m, 2H) 5.33 (d, J=2.86 Hz, 1H) 5.90 (s, 1H) 12.40-12.99 (m, 1H)

Step 3: Synthesis of tert-butyl 2-(8-chloro-5,7-dihydrofuro[3,4-d]pyrazolo[1,5-a]pyrimidin-2-yl)piperidine-1-carboxylate 35

To a solution of intermediate 34 (700 mg, 1.9 mmol) in dry ACN (15 mL), DIPEA (1.7 mL, 9.7 mmol, 5 eq.) and POCl$_3$ (0.54 mL, 5.8 mmol, 3 eq.) were added. The reaction mixture was stirred at 70° C. during 2 days then cooled to room temperature and co-evaporated under reduce pressure with toluene (3 times). The residue was poured into a saturated solution of Na$_2$CO$_3$ cooled with ice and extracted twice with DCM (2×30 mL). The combined organics were dried over magnesium sulfate and evaporated in vacuo giving targeted intermediate 35 (700 mg, 85% pure, 95% yield). The crude was used as such for the next step.

LCMS (M+1)=379.

Step 4: Synthesis of tert-butyl 2-(8-morpholino-5,7-dihydrofuro[3,4-d]pyrazolo[1,5-a]-pyrimidin-2-yl)piperidine-1-carboxylate 36

To a solution of intermediate 35 (700 mg, 1.84 mmol) in THF (20 mL) was added morpholine (0.5 mL, 5.5 mmol, 3 eq.). The resulting mixture was stirred at 50° C. for 65 hours. The reaction mixture was then cooled to room temperature and evaporated in vacuo. The residue was dissolved in EtOAc and washed with water then brine. The organic layer was dried over magnesium sulfate and evaporated in vacuo to give intermediate 36 (250 mg, 83% pure, 31% yield) as a sticky solid.

LCMS (M+1)=430.

Step 5: Synthesis of 8-morpholino-2-(piperidin-2-yl)-5,7-dihydrofuro[3,4-d]pyrazolo[1,5-a]-pyrimidine 37

Intermediate 36 (250 mg, 0.58 mmol) was dissolved in HCl (4M) solution in dioxane (5 mL). The resulting mixture was stirred at room temperature for 1 hour. The reaction mixture was then poured into an aqueous saturated solution of Na$_2$CO$_3$ cooled by ice. The resulting mixture was extracted with DCM (3×15 mL). The combined organics were dried over magnesium sulfate and evaporated in vacuo to give intermediate 37 (130 mg, 67% yield) as a sticky solid.

The crude was used as such for the next step.

LCMS (M+1)=330.

Step 6: Synthesis of N-(4-methyl-2-(2-(8-morpholino-5,7-dihydrofuro[3,4-d]pyrazolo-[1,5-a]-pyrimidin-2-yl)piperidine-1-carbonyl)phenyl)methanesulfonamide P25

To a solution of intermediate 37 (130 mg, 0.4 mmol) in DMF (3 mL), 2-(methanesulfonamido)-5-methyl-benzoic acid 9-a (109 mg, 0.47 mmol, 1.2 eq.), DIPEA (0.204 mL, 1.18 mmol, 3 eq.) and HATU (225 mg, 0.59 mmol, 1.5 eq.) were added. The resulting mixture was stirred at room temperature for overnight. The reaction mixture was then quenched with water and extracted with EtOAc (2×20 mL). The combined organics were washed with brine (3×15 mL), dried over magnesium sulfate and evaporated in vacuo. The crude was purified by column chromatography using a gradient from pure DCM to DCM/MeOH (95/5). The fraction was evaporated and purified by prep HPLC to give compound P25 (40 mg, 100% pure, 18% yield) as a white solid.

LCMS (M+1)=541.

$^1$H NMR (370 K, 400 MHz, DMSO-$d_6$) δ ppm 1.51-1.72 (m, 4H) 1.99 (br. s., 1H) 2.27 (s, 3H) 2.31 (br. s., 1H) 2.98 (s, 3H) 3.10-3.21 (m, 1H) 3.67-3.72 (m, 4H) 3.76-3.81 (m, 4H) 3.83-3.95 (m, 1H) 4.79 (s, 2H) 5.27 (s, 2H) 5.51-5.77 (m, 1H) 6.36 (s, 1H) 7.15 (d, J=1.98 Hz, 1H) 7.22 (dd, J=8.25, 1.43 Hz, 1H) 7.33 (d, J=8.36 Hz, 1H) 8.05-8.46 (m, 1H).

Synthesis of N-(2-(2-(9-(dimethylamino)-5-methyl-5,6,7,8-tetrahydropyrazolo-[1,5-a]pyrido[2,3-d]pyrimidin-2-yl)piperidine-1-carbonyl)-4-methylphenyl)-methane-sulfonamide P26 and N-(2-(2-(5-(dimethylamino)-9-methyl-6,7,8,9-tetrahydropyrazolo-[1,5-a]pyrido[3,2-e]pyrimidin-2-yl)piperidine-1-carbonyl)-4-methylphenyl)methane-sulfonamide P27

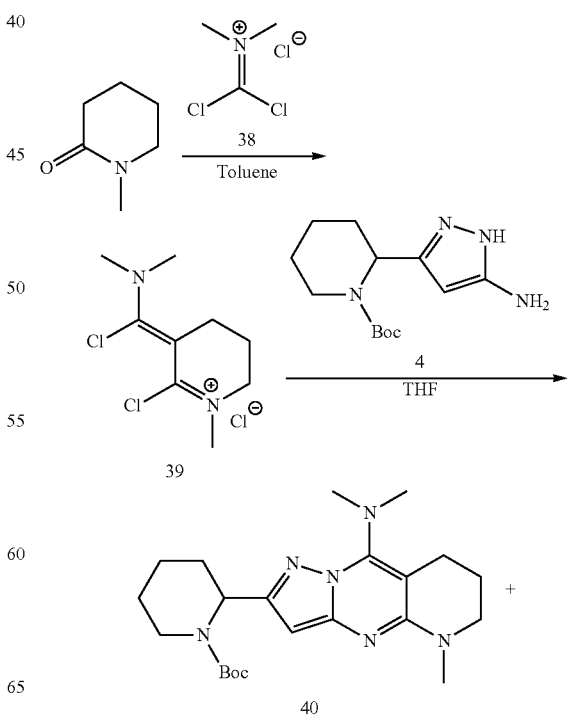

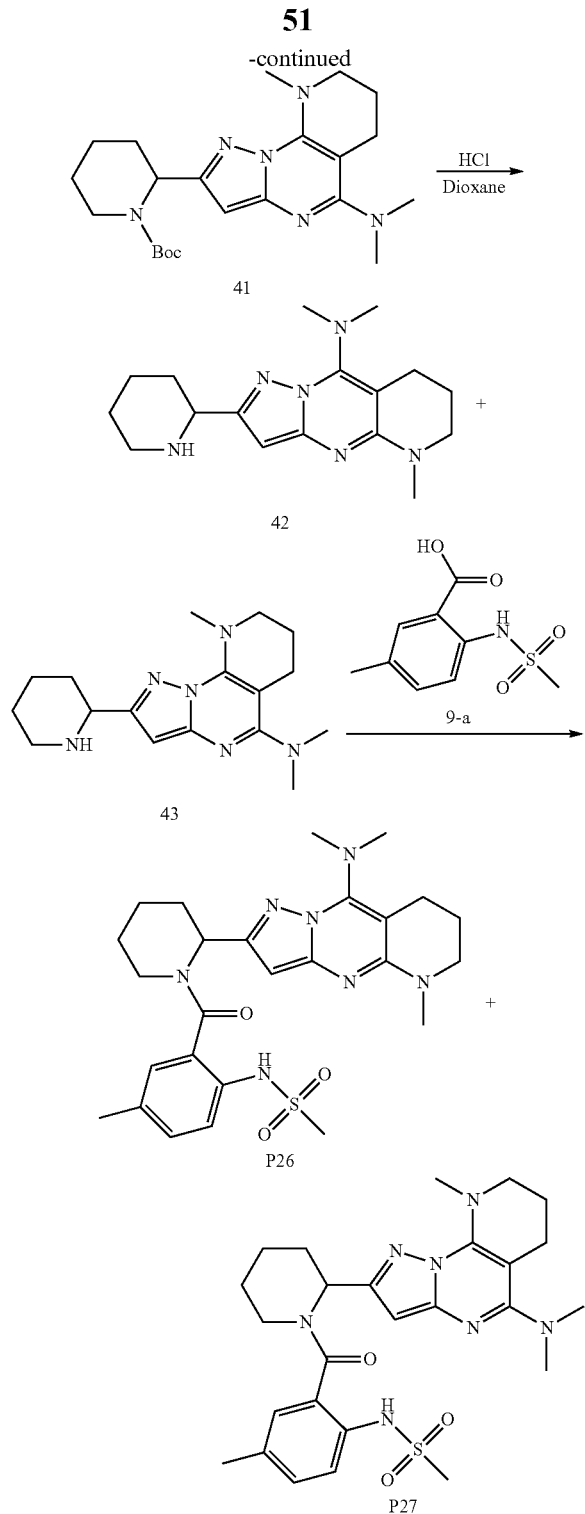

1-methyl-2-piperidone (0.17 mL, 1.5 mmol, 2 eq.). The resulting mixture was heated to reflux for 30 minutes. Then pyrazolo-pyrimidine-boc-piperidine 4 (200 mg, 0.75 mmol) dissolved in THF (4 mL) and DIPEA (0.39 mL, 2.25 mmol, 3 eq.) were added. The resulting mixture was heated to 80° C. for 30 minutes. The reaction mixture was allowed to cool to room temperature and extracted with EtOAc. The organic layer was then dried over magnesium sulfate, evaporated in vacuo. The crude was purified by column chromatography using a gradient from DCM to DCM/MeOH (9/1) giving a mixture of two isomers. This mixture was separated by SFC yielding intermediate 40 (45 mg, 100% pure, 15% yield) and intermediate 41 (40 mg, 100% pure, 12% yield).

LCMS (M+1)=415.

40: $^1$H NMR (600 MHz, DMSO-$d_6$) δ ppm 1.33-1.46 (m, 11H) 1.55 (br. s., 2H) 1.70-1.77 (m, 1H) 1.77-1.84 (m, 2H) 2.26 (d, J=12.76 Hz, 1H) 2.61 (t, J=6.02 Hz, 2H) 2.80 (s, 6H) 3.30-3.34 (m, 2H) 3.47 (s, 3H) 3.83-3.94 (m, 1H) 5.34 (br. s., 1H) 5.81 (s, 1H).

41: $^1$H NMR (600 MHz, DMSO-$d_6$) δ ppm 1.33-1.46 (m, 11H) 1.54 (d, J=9.10 Hz, 2H) 1.66-1.74 (m, 1H) 1.78-1.85 (m, 2H) 2.25 (d, J=13.06 Hz, 1H) 2.66-2.72 (m, 2H) 2.97 (s, 6H) 3.06 (s, 3H) 3.36-3.39 (m, 2H) 3.86 (d, J=12.91 Hz, 1H) 5.29 (br. s., 1H) 5.65 (s, 1H).

This reaction was done in a bigger scale (1 g of intermediate 4) and the mixture was used as such for the next step.

Step 2: Synthesis of N,N,5-trimethyl-2-(piperidin-2-yl)-5,6,7,8-tetrahydropyrazolo[1,5-a]-pyrido[2,3-d]pyrimidin-9-amine 42 and N,N,9-trimethyl-2-(piperidin-2-yl)-6,7,8,9-tetrahydropyrazolo[1,5-a]pyrido[3,2-e]pyrimidin-5-amine 43

A mixture of intermediate 40 and intermediate 41 (730 mg, 1.76 mmol) were dissolved in HCl (4M) solution in 1,4-dioxane (15 ml) and the resulting mixture was stirred at room temperature for 1 hour. The reaction mixture was then poured into an iced saturated solution of Na$_2$CO$_3$ and extracted with DCM three times. The combined organic layers were dried over magnesium sulfate and evaporated in vacuo to give a mixture of intermediate 42 and intermediate 43 (423 mg, 76% yield).

The crude was used as such for the next step.
LCMS (M+1)=315.

Step 3: Synthesis of N-(2-(2-(9-(dimethylamino)-5-methyl-5,6,7,8-tetrahydropyrazolo[1,5-a]-pyrido[2,3-d]pyrimidin-2-yl)piperidine-1-carbonyl)-4-methyl-phenyl)methanesulfonamide P26 and N-(2-(2-(5-(dimethylamino)-9-methyl-6,7,8,9-tetrahydropyrazolo[1,5-a]pyrido-[3,2-e]pyrimidin-2-yl)piperidine-1-carbonyl)-4-methylphenyl)methanesulfonamide P27

To a solution of intermediate 42 and intermediate 43 (423 mg, 1.345 mmol) in DMF (12 mL) 2-(methanesulfonamido)-5-methyl-benzoic acid 9-a (370 mg, 1.61 mmol, 1.2 eq.), DIPEA (0.46 mL, 2.7 mmol, 2 eq.) and HATU (767 mg, 2 mmol, 1.5 eq.) were added. The reaction mixture was stirred at room temperature for overnight. The reaction mixture was then quenched with water and extracted with EtOAc (2×20 mL). The combined organics were washed with brine (3×50 mL) then dried over magnesium sulfate and evaporated in the vacuo. The crude was purified by column chromatography using a gradient from pure DCM to DCM/MeOH (95/5) to give a mixture of the two products. This mixture was separated by SFC to give compound P26

Step 1: Synthesis of tert-butyl 2-(9-(dimethylamino)-5-methyl-5,6,7,8-tetrahydropyrazolo-[1,5-a]pyrido[2,3-d]pyrimidin-2-yl)piperidine-1-carboxylate 40 and tert-butyl 2-(5-(dimethylamino)-9-methyl-6,7,8,9-tetrahydropyrazolo[1,5-a]pyrido[3,2-e]pyrimidin-2-yl)piperidine-1-carboxylate 41

To a solution of Viehe's salt 38 (364 mg, 2.24 mmol 3 eq.) in degassed toluene under inert atmosphere was added (110 mg, 100% pure, 15% yield) and compound P27 (250 mg, 100% pure, 35% yield) as white powders.

LCMS (M+1)=526.

P26: $^1$H NMR (600 MHz, DMSO-$d_6$) δ ppm 1.52-1.64 (m, 4H) 1.80-1.88 (m, 2H) 1.88-1.95 (m, 1H) 2.21-2.28 (m, 4H) 2.72 (t, J=6.46 Hz, 2H) 2.99 (s, 3H) 3.01 (s, 6H) 3.08 (s, 3H) 3.10-3.24 (m, 1H) 3.38 (t, J=5.65 Hz, 2H) 3.66-4.14 (m, 1H) 5.17-5.66 (m, 1H) 5.83 (s, 1H) 7.19-7.23 (m, 2H) 7.33 (d, J=8.51 Hz, 1H) 8.37 (br. s., 1H).

P27: $^1$H NMR (400 MHz, DMSO-$d_6$) δ ppm 1.51-1.68 (m, 4H) 1.83 (quin, J=5.75 Hz, 2H) 1.88-1.99 (m, 1H) 2.21-2.31 (m, 1H) 2.27 (s, 2H) 2.64 (t, J=6.06 Hz, 2H) 2.84 (s, 6H) 2.99 (s, 3H) 3.09-3.20 (m, 1H) 3.34 (dd, J=9.28, 4.44 Hz, 2H) 3.49 (s, 3H) 3.89 (br. s., 1H) 5.51 (br. s., 1H) 5.97 (s, 1H) 7.17 (s, 1H) 7.20 (d, J=8.01 Hz, 1H) 7.33 (d, J=8.07 Hz, 1H) 8.34 (br. s., 1H).

Synthesis of N-(4-methyl-2-(2-(9-morpholino-7,8-dihydro-5H-pyrano[3,4-d]pyrazolo-[1,5-a]pyrimidin-2-yl)piperidine-1-carbonyl)phenyl)methane-sulfonamide P28

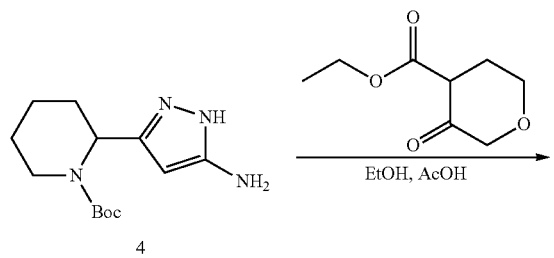

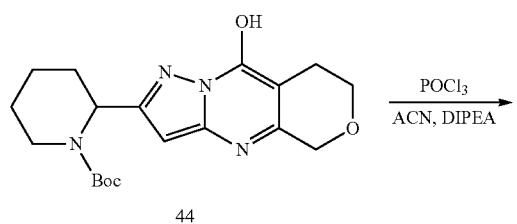

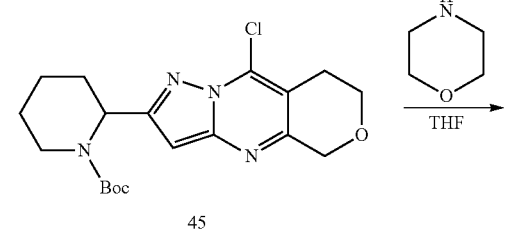

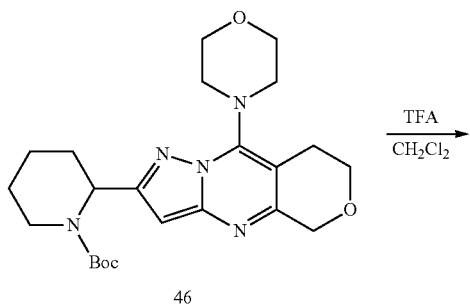

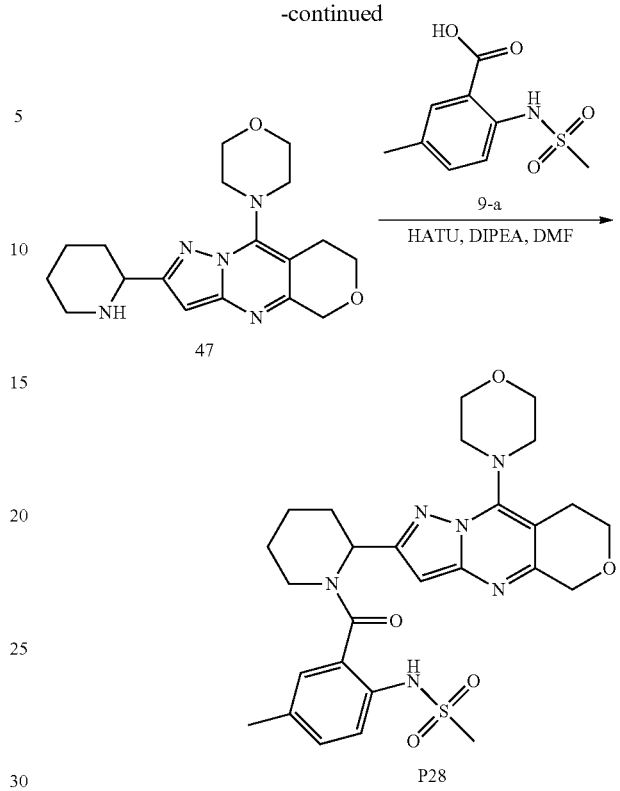

Step 1: Synthesis of tert-butyl 2-(9-hydroxy-7,8-dihydro-5H-pyrano[3,4-d]pyrazolo[1,5-a]-pyrimidin-2-yl)piperidine-1-carboxylate 44

To the intermediate 4 (500 mg, 1.87 mmol) in EtOH (50 mL), ethyl 3-oxotetrahydro-2H-pyran-4-carboxylate (0.55 mL, 3.74 mmol, 2 eq.) and AcOH (1.07 mL, 18.69 mmol, 10 eq.) were added. The reaction mixture was stirred at reflux for 2 hours then cooled to room temperature and evaporated under reduce pressure. The residue was triturated in DIPE. The precipitate was filtered to give intermediate 44 (675 mg, 100% pure, 96% yield).

LCMS (M+1)=375.

1H NMR (400 MHz, DMSO-$d_6$) δ ppm 1.31-1.47 (m, 11H) 1.56 (br. s., 2H) 1.70 (d, J=5.06 Hz, 1H) 2.32 (d, J=12.98 Hz, 1H) 2.44-2.48 (m, 2H) 2.70-2.88 (m, 1H) 3.81-3.96 (m, 3H) 4.51 (s, 2H) 5.32 (br. s., 1H) 5.77 (s, 1H) 12.08 (br. s., 1H).

Step 2: Synthesis of tert-butyl 2-(9-chloro-7,8-dihydro-5H-pyrano[3,4-d]pyrazolo[1,5-a]-pyrimidin-2-yl)piperidine-1-carboxylate 45

To the intermediate 44 (675 mg, 1.80 mmol) in ACN (50 mL) under inert atmosphere, DIPEA (1.55 mL, 9.03 mmol, 5 eq.) and POCl$_3$ (0.5 mL, 5.41 mmol, 3 eq.) were added. The reaction mixture was stirred at 70° C. for 8 hours and at room temperature for 2 days.

The reaction mixture was co-evaporated with toluene two times and dissolved in a minimum amount of ACN then poured into a saturated solution of NaHCO$_3$ cooled with ice. The resulting precipitate was stirred for 30 minutes and filtered.

The mixture was dissolved in dichloromethane and evaporated under reduce pressure to give a brown sticky crude as intermediate 45 (741 mg, 89% pure, 93% yield). The crude was used as such for the next step.

LCMS (M+1)=393.

Step 3: Synthesis of tert-butyl 2-(9-morpholino-7,8-dihydro-5H-pyrano[3,4-d]pyrazolo[1,5-a]-pyrimidin-2-yl)piperidine-1-carboxylate 46

Intermediate 45 (741 mg, 89% pure, 1.68 mmol) was dissolved in THF (15 mL). Morpholine (5 eq., 0.74 mL, 8.4 mmol) was added. The reaction mixture was stirred at 50° C. during 1 day then cooled to room temperature and evaporated under reduce pressure. The residue was dissolved in EtOAc and washed with water (3×50 mL) and once with brine. The organic layer was evaporated under reduce pressure. The crude was then triturated in water and filtered to give intermediate 46 (450 mg, 92% pure, 60% yield) as a green powder.

LCMS (M+1)=444.

1H NMR (400 MHz, DMSO-$d_6$) δ ppm 1.32-1.45 (m, 11H) 1.49-1.62 (m, 2H) 1.70-1.85 (m, 1H) 2.29 (d, J=11.22 Hz, 1H) 2.75-3.03 (m, 3H) 3.57 (br. s., 4H) 3.69-3.81 (m, 4H) 3.82-3.98 (m, 3H) 4.63 (s, 2H) 5.42 (br. s, 1H) 6.15 (s, 1H).

Step 4: Synthesis of 9-morpholino-2-(piperidin-2-yl)-7,8-dihydro-5H-pyrano[3,4-d]pyrazolo-[1,5-a]pyrimidine 47

To a solution of intermediate 46 (100 mg, 0.23 mmol) in DCM (2 mL), TFA (0.09 mL, 1.13 mmol 5 eq.) was added. The reaction mixture was stirred at room temperature for 1 day then evaporated under reduce pressure and dissolved in water. The water layer was basified with a saturated solution of $Na_2CO_3$ and extracted with DCM (2×50 mL). The combined organic layers were dried over magnesium sulfate and concentrated in vacuo giving intermediate 47 (60 mg, 85% pure, 77% yield) as a brown pale powder.

LCMS (M+1)=344.

$^1$H NMR (400 MHz, DMSO-$d_6$) δ ppm 1.62-1.75 (m, 2H) 1.75-1.89 (m, 3H) 2.18-2.26 (m, 1H) 2.85 (t, J=5.72 Hz, 2H) 3.04-3.10 (m, 1H) 3.35-3.39 (m, 1H) 3.56-3.62 (m, 4H) 3.80 (t, J=4.62 Hz, 4H) 3.84-3.91 (m, 2H) 4.44-4.51 (m, 1H) 4.65 (s, 2H) 6.51 (s, 1H).

Step 5: Synthesis of N-(4-methyl-2-(2-(9-morpholino-7,8-dihydro-5H-pyrano[3,4-d]-pyrazolo[1,5-a]pyrimidin-2-yl)piperidine-1-carbonyl)phenyl)methanesulfonamide P28

To a solution of intermediate 47 (150 mg, 0.437 mmol) in dry DMF (4 mL), 2-(methanesulfonamido)-5-methyl-benzoic acid (120.2 mg, 0.524 mmol, 1.2 eq.), DIPEA (0.151 mL, 0.874 mmol, 2 eq.) and HATU (249 mg, 0.66 mmol, 1.5 eq.) were added. The reaction mixture was stirred at room temperature for 1 hour then quenched with water, extracted with EtOAc, washed with brine (3×20 mL). The combined organics were dried over magnesium sulfate and concentrated in vacuo. The crude was purified on silica column with a gradient from pure DCM to DCM/MeOH (9/1).

The product fraction was concentrated and recrystallized in DIPE/ACN (3/1) giving compound P28 (35 mg, 100% pure, 14% yield) as white crystals.

LCMS (M+1)=555.

$^1$H NMR (320K, 400 MHz, DMSO-$d_6$) δ ppm 0.01 (s, 1H) 1.46-1.69 (m, 4H) 1.90-2.13 (m, 1H) 2.20-2.38 (m, 4H) 2.41 (s, 1H) 2.85 (t, J=5.57 Hz, 2H) 3.00 (s, 3H) 3.51-3.64 (m, 4H) 3.73-3.84 (m, 3H) 3.89 (t, J=5.45 Hz, 2H) 4.64 (s, 2H) 6.36 (s, 1H) 7.19 (s, 1H) 7.23 (d, J=8.48 Hz, 1H) 7.32 (d, J=8.07 Hz, 1H) 8.72 (br. s., 1H).

Synthesis of 2-(1-(5-methylquinazolin-4-yl)piperidin-2-yl)-9-morpholino-7,8-dihydro-5H-pyrano[3,4-d]pyrazolo[1,5-a]pyrimidine P29

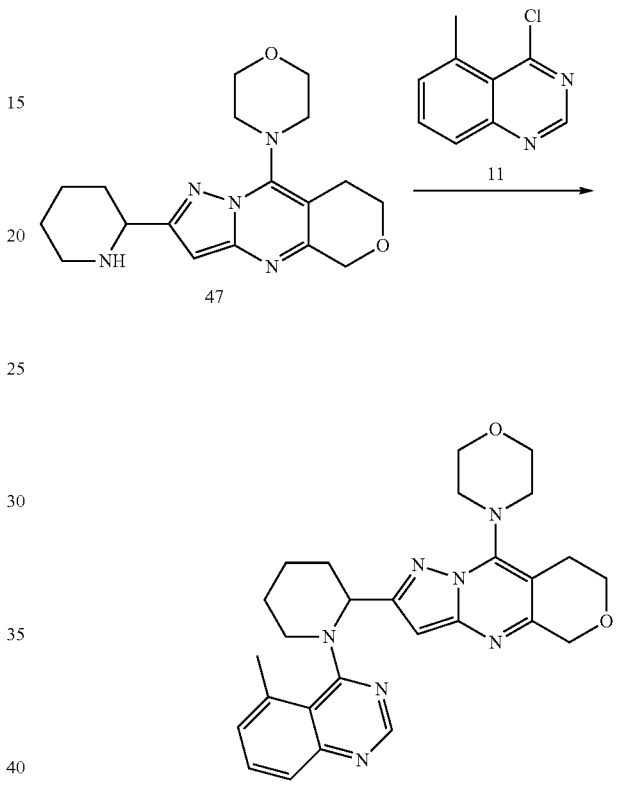

To a solution of intermediate 47 (300 mg, 0.87 mmol) in 2-methoxyethanol (10 mL), 4-chloro-5-methylquinazoline 11 (246 mg, 1.31 mmol, 1.5 eq.) and DIPEA (0.45 mL, 2.62 mmol, 3 eq.) were added. The reaction mixture was stirred at 50° C. during 5 days then cooled to room temperature and poured into ice water. The precipitate was filtered. The solid was dissolved in DCM and washed two times with a saturated solution of sodium bicarbonate. The organic layer was dried over magnesium sulfate and evaporated under reduce pressure. The residue was recrystallized in ACN to give compound P29 (136 mg, 100% pure, 32% yield) as white crystals.

LCMS (M+1)=486.

$^1$H NMR (420 K, 400 MHz, DMSO-$d_6$) δ ppm 1.59 (br. s., 1H) 1.71 (br. s., 2H) 1.88 (br. s., 1H) 2.30 (br. s., 2H) 2.80-2.85 (m, 2H) 2.88 (br. s., 3H) 3.37-3.49 (m, 4H) 3.55 (d, J=10.34 Hz, 2H) 3.73 (d, J=4.18 Hz, 4H) 3.81-3.94 (m, 2H) 4.60 (s, 2H) 5.62 (br. s., 1H) 6.09 (br. s., 1H) 7.34 (d, J=5.94 Hz, 1H) 7.53-7.71 (m, 2H) 8.49 (br. s., 1H).

Synthesis of 2-(1-(5-methylquinazolin-4-yl)piperidin-2-yl)-9-morpholino-6,8-dihydro-5H-pyrano[4,3-d]pyrazolo[1,5-a]pyrimidine P30

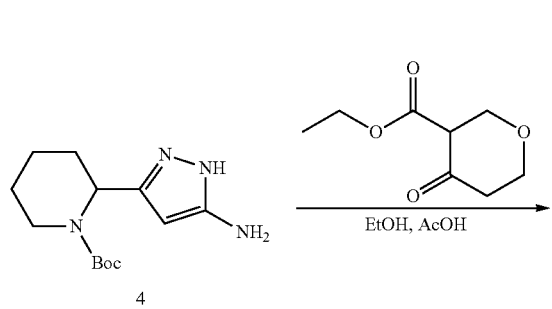

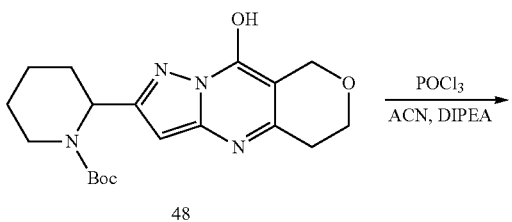

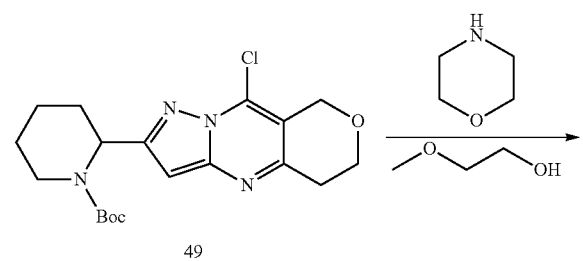

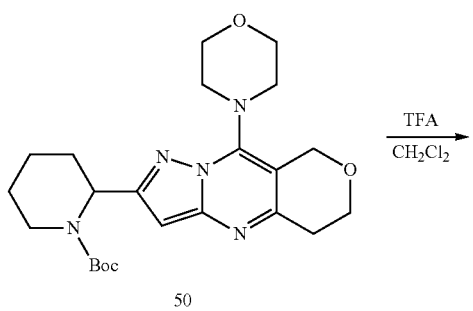

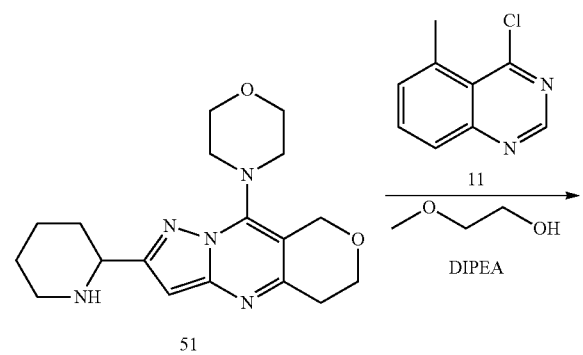

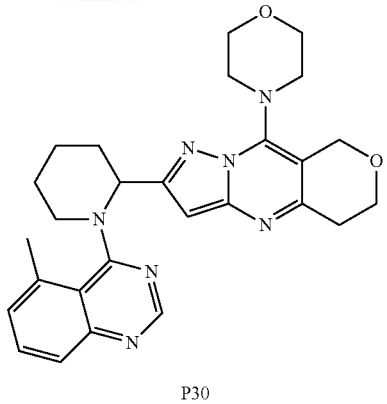

P30

Step 1: Synthesis of tert-butyl 2-(9-hydroxy-6,8-dihydro-5H-pyrano[4,3-d]-pyrazolo[1,5-a]-pyrimidin-2-yl)piperidine-1-carboxylate 48

To a solution of intermediate 4 (2 g, 7.2 mmol) in ethanol (100 mL) methyl 4-oxotetrahydro-2H-pyran-3-carboxylate (2.4 g, 15 mmol, 2.1 eq.) and acetic acid (4.1 mL, 10 eq.) were added. The solution was stirred for 4 hours at reflux. The solution was then concentrated in vacuo and triturated in diisopropyl ether. The solid was filtered off and dried into the oven to give intermediate 48 (1.95 g, 72%) as a white powder.

LCMS m/z=375 (M+H)$^+$ $^1$H NMR (400 MHz, DMSO-d$_6$) δ ppm 1.30-1.38 (m, 2H) 1.42 (s, 9H) 1.48-1.63 (m, 2H) 1.64-1.77 (m, 1H) 2.31 (d, J=13.64 Hz, 1H) 2.69 (s, 2H) 2.72-2.85 (m, 1H) 3.79-3.96 (m, 3H) 4.44 (s, 2H) 5.31 (br. s, 1H) 5.77 (s, 1H) 12.20 (s, 1H)

Step 2: Synthesis of tert-butyl 2-(9-chloro-6,8-dihydro-5H-pyrano[4,3-d]pyrazolo[1,5-a]-pyrimidin-2-yl)piperidine-1-carboxylate 49

To a solution of intermediate 48 (1.5 g, 4 mmol) and DIPEA (3.4 mL, 20 mmol, 5 eq.) in acetonitrile (50 mL), phosphorus oxychloride (3.7 mL, 40 mmol, 10 eq.) was added dropwise at room temperature. The resulting mixture was then heated to 70° C. and stirred for 16 hours. The solution was concentrated in vacuo and coevaporated with toluene twice. The crude was diluted with dichloromethane (100 mL) and washed with NaHCO$_3$ (sat.) solution. The combined organics were dried with anhydrous MgSO$_4$, filtered off and concentrated in vacuo to give intermediate 49 (2.1 g, 97%, 73% purity) which was used as such into the next step.

LCMS m/z=393 (M+H)$^+$

Step 3: Synthesis of tert-butyl 2-(9-morpholino-6,8-dihydro-5H-pyrano[4,3-d]pyrazolo[1,5-a]-pyrimidin-2-yl)piperidine-1-carboxylate 50

To a solution of intermediate 49 (2.1 g, 73% pure, 2.6 mmol) in 2-methoxy ethanol (80 mL) the morpholine (1.2 mL, 13 mmol, 5 eq.) was added dropwise at room temperature. The resulting mixture was heated to 50° C. After 16 hours the solution was concentrated in vacuo and diluted with EtOAc (100 mL). The solution was washed with sat. NaHCO$_3$ solution and the combined organics were dried with MgSO₄, filtered off, concentrated in vacuo and purified by column chromatography eluting with a gradient starting from 0% to 10% MeOH and DCM to give intermediate 50 as oil (1.7 g, 97%, 70% purity) which was used as such into the next step.

LCMS m/z=444 (M+H)⁺

Step 4: Synthesis of 9-morpholino-2-(piperidin-2-yl)-6,8-dihydro-5H-pyrano[4,3-d]pyrazolo-[1,5-a]pyrimidine 51

To a solution of intermediate 50 (1.7 g, 70% purity, 3.8 mmol) in dichloromethane (40 mL) was added TFA (0.88 mL, 11.5 mmol, 3 eq.) at room temperature under inert atmosphere. The solution was stirred for 16 hours at room temperature. The solution was then adjusted to pH=7 with saturated Na₂CO₃ solution. The combined organics were collected, dried with anhydrous MgSO4, filtered off and concentrated in vacuo to give intermediate 51 (800 mg, 60%) which was used as such into the next step.

LCMS m/z=344 (M+H)⁺

¹H NMR (400 MHz, DMSO-d₆) δ ppm 1.40-1.63 (m, 4H) 1.78-1.87 (m, 1H) 1.92-2.02 (m, 1H) 2.67-2.77 (m, 1H) 2.85-2.93 (m, 2H) 3.03-3.11 (m, 2H) 3.45-3.54 (m, 4H) 3.71-3.80 (m, 4H) 3.81-3.87 (m, 1H) 3.98 (s, 2H) 4.75 (s, 2H) 6.35 (s, 1H)

Step 5: Synthesis of 2-(1-(5-methylquinazolin-4-yl)piperidin-2-yl)-9-morpholino-6,8-dihydro-5H-pyrano[4,3-d]pyrazolo[1,5-a]pyrimidine P30

To a solution of intermediate 51 (130 mg, 0.37 mmol) in 2-methoxy ethanol (20 mL), DIPEA (0.2 mL, 1.13 mmol, 3 eq.) and 4-chloro-5-methylquinazoline 11 (100 mg, 0.5 mmol, 1.3 eq.) were added at room temperature. The resulting mixture was stirred at room temperature for 48 hours. After concentration in vacuo the crude was purified by HPLC to give compound P30 (80 mg, 43%) as white solid.

LCMS m/z=486 (M+H)⁺

¹H NMR (400 MHz, DMSO-d₆) δ ppm 1.48-1.65 (m, 1H) 1.66-1.77 (m, 2H) 1.81-1.94 (m, 1H) 2.21-2.38 (m, 2H) 2.75-2.89 (m, 5H) 3.33-3.39 (m, 4H) 3.40-3.46 (m, 1H) 3.49-3.58 (m, 1H) 3.68-3.74 (m, 4H) 3.93-4.00 (m, 2H) 4.72 (s, 2H) 5.62 (br. s, 1H) 6.12 (br. s, 1H) 7.35 (d, J=6.38 Hz, 1H) 7.54-7.68 (m, 2H) 8.49 (s, 1H)

Synthesis of 2-(1-(2-chloro-5-methylquinazolin-4-yl)piperidin-2-yl)-9-morpholino-6,8-dihydro-5H-pyrano[4,3-d]pyrazolo[1,5-a]pyrimidine P31

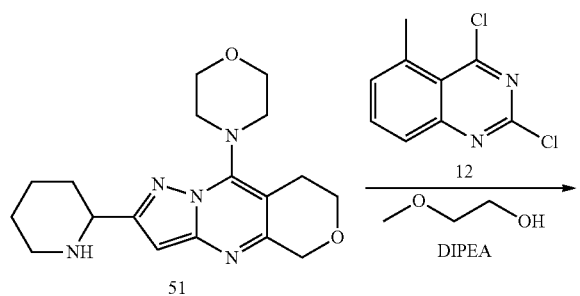

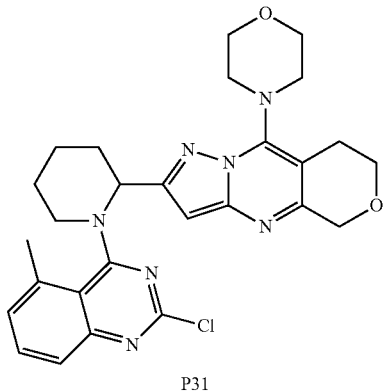

P31

To a solution of intermediate 51 (30 mL) in a sealed tube, DIPEA (0.8 mL, 4.8 mmol, 3 eq.) and 2,4-dichloro-5-methylquinazoline 12 (930 mg, 2.4 mmol, 1.5 eq.) were added at room temperature. The resulting mixture was heated to 50° C. and stirred for 2 hours. The solution was then concentrated in vacuo, diluted with dichloromethane (80 mL) and washed with NaHCO₃ solution. The combined organics were dried with MgSO₄, filtered off and concentrated in vacuo. The crude was then purified on HPLC to give compound P31 (250 mg, 30%) as white solid.

LCMS m/z=520 (M+H)⁺

¹H NMR (400 MHz, DMSO-d₆) δ ppm 1.53-1.67 (m, 1H) 1.72 (br. s., 2H) 1.82-1.94 (m, 1H) 2.19-2.40 (m, 2H) 2.83 (s, 3H) 2.91 (t, J=6.40 Hz, 2H) 3.35-3.43 (m, 4H) 3.52-3.76 (m, 6H) 3.99 (t, J=6.40 Hz, 2H) 4.75 (s, 2H) 5.68 (br. s, 1H) 6.20 (br. s., 1H) 7.36 (d, J=7.04 Hz, 1H) 7.52 (d, J=8.36 Hz, 1H) 7.66 (t, J=7.90 Hz, 1H)

Synthesis of N-(5-methyl-4-(2-(9-morpholino-6,8-dihydro-5H-pyrano[4,3-d]pyrazolo-[1,5-a]pyrimidin-2-yl)piperidin-1-yl)quinazolin-2-yl)methanesulfonamide P32

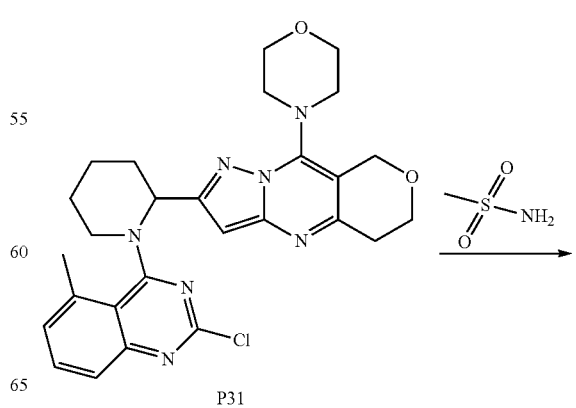

P31

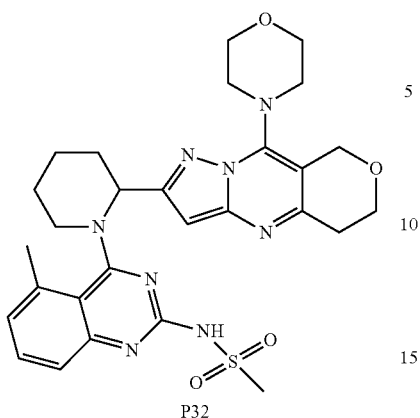

P32

To a solution of compound P31 (80 mg, 0.15 mmol) in 1,4-dioxane (5 mL) was added methane sulfonamide (30 mg, 0.3 mmol, 2 eq.), cesium carbonate (125 mg, 0.385 mmol, 2.5 eq.), 4,5-bis(diphenylphosphino)-9,9-dimethylxanthene (44 mg, 0.07 mmol, 0.5 eq.) and palladium acetate (17 mg, 0.07 mmol, 0.5 eq.) in a microwave vial. The solution was heated till 110° C. in a microwave reactor for 10 minutes. The solution was the filtered over dicalite, concentrated in vacuo and purified on HPLC to give compound P32 (25 mg, 28%) as white solid.

LCMS m/z=579 (M+H)+

$^1$H NMR (400 MHz, DMSO-d$_6$) δ ppm 1.53-1.66 (m, 1H) 1.66-1.78 (m, 2H) 1.79-1.90 (m, 1H) 2.17-2.34 (m, 1H) 2.39-2.46 (m, 1H) 2.70 (br. s., 3H) 2.95 (br. s., 5H) 3.40-3.49 (m, 4H) 3.53-3.63 (m, 1H) 3.72-3.77 (m, 4H) 3.81-3.89 (m, 1H) 3.97-4.02 (m, 2H) 4.76 (s, 2H) 6.02 (br. s, 1H) 6.27 (br. s, 1H) 7.09-7.13 (m, 1H) 7.24-7.30 (m, 1H) 7.47-7.56 (m, 1H).

Synthesis of 2-(1-(2-ethoxy-5-methylquinazolin-4-yl)piperidin-2-yl)-9-morpholino-6,8-dihydro-5H-pyrano[4,3-d]pyrazolo[1,5-a]pyrimidine P33

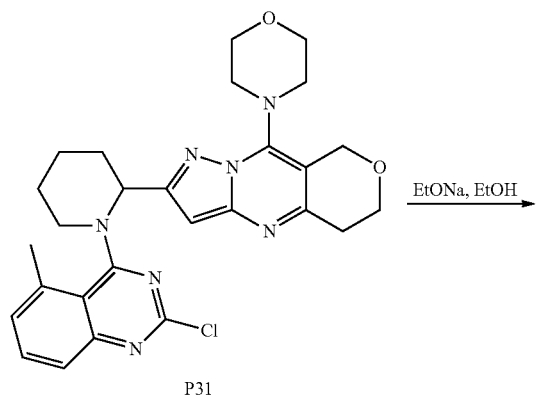

P31

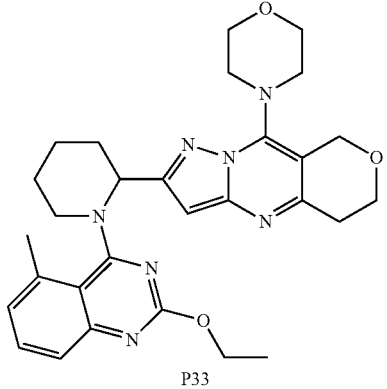

P33

To a solution of compound P31 (100 mg, 0.192 mmol) in ethanol (5 ml) sodium ethoxide (0.36 ml, 0.961 mmol) was added. The resulting mixture was stirred at 80° C. overnight. The reaction mixture was allowed to cool down to room temperature and the solvent was evaporated. The resulting residue was purified by column chromatography using dichloromethane and methanol to give compound P33 (30 mg, 30%).

LCMS m/z=530 (M+H)+

$^1$H NMR (420 K, 400 MHz, DMSO-d$_6$) δ ppm 1.30 (t, J=1.00 Hz, 3H) 1.55-1.66 (m, 1H) 1.67-1.77 (m, 2H) 1.82-1.94 (m, 1H) 2.23-2.33 (m, 2H) 2.85 (s, 3H) 2.89 (t, J=6.05 Hz, 2H) 3.32-3.43 (m, 4H) 3.47-3.58 (m, 2H) 3.68-3.75 (m, 4H) 3.97 (t, J=6.05 Hz, 2H) 4.37 (q, J=6.90 Hz, 2H) 4.73 (s, 2H) 5.47-5.56 (m, 1H) 6.14 (br. s., 1H) 7.13 (d, J=7.04 Hz, 1H) 7.38 (d, J=8.14 Hz, 1H) 7.52 (t, J=7.70 Hz, 1H)

Synthesis of N-(4-methyl-2-(2-(9-morpholino-6,8-dihydro-5H-pyrano[4,3-d]pyrazolo-[1,5-a]pyrimidin-2-yl)piperidine-1-carbonyl)phenyl)methanesulfonamide P34

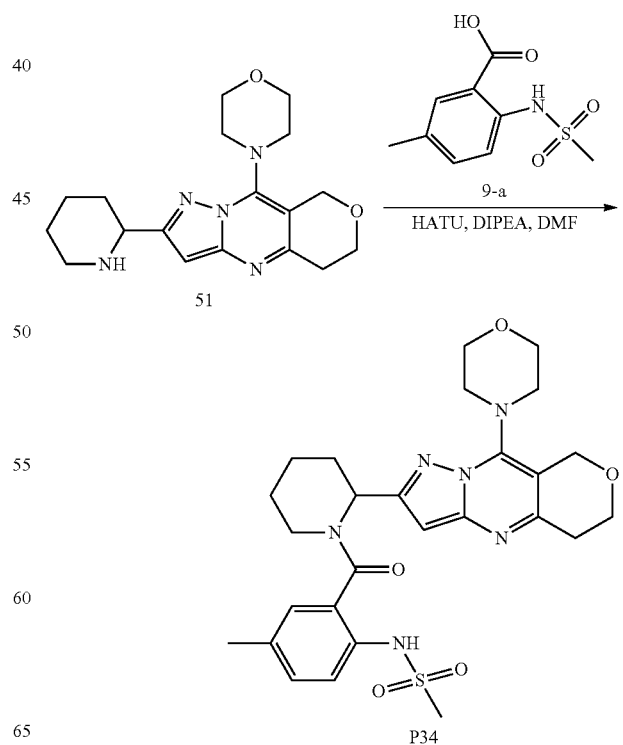

To a solution of intermediate 51 (100 mg, 0.262 mmol) in dry DMF (4 mL), 2-(methanesulfonamido)-5-methyl-benzoic acid 9-a (72 mg, 0.31 mmol, 1.2 eq.), DIPEA (0.13 mL, 0.786 mmol, 3 eq.) and HATU (200 mg, 0.52 mmol, 2 eq.) were added. The reaction mixture was stirred at room temperature for 3 hours then quenched with water, extracted with dichloromethane, washed with brine (3×20 mL). The combined organics were dried over magnesium sulfate and concentrated in vacuo. The crude was purified on silica column with a gradient from pure DCM to DCM/MeOH (9/1) to yield compound P34 (50 mg, 34%) as white powder.

LCMS (M+1)=556.

$^{1}$H NMR (400 MHz, DMSO-$d_6$, 320K) δ ppm 1.50-1.71 (m, 4H) 1.95-2.06 (m, 2H) 2.26 (s, 3H) 2.29-2.35 (m, 1H) 2.89-2.94 (m, 2H) 2.99 (s, 3H) 3.15-3.25 (m, 1H) 3.48-3.53 (m, 3H) 3.76-3.81 (m, 4H) 3.87-3.93 (m, 1H) 3.99 (t, J=6.20 Hz, 2H) 4.76 (s, 2H) 5.61-5.69 (m, 1H) 6.34 (s, 1H) 7.14-7.24 (m, 2H) 7.31-7.38 (m, 1H) 8.13-8.30 (m, 1H)

Synthesis of 9-methyl-2-(1-(5-methylquinazolin-4-yl)piperidin-2-yl)-5,6,7,8-tetrahydropyrazolo[5,1-b]quinazoline P35 and 5-methyl-2-(1-(5-methylquinazolin-4-yl)piperidin-2-yl)-6,7,8,9-tetrahydropyrazolo[1,5-a]quinazoline P36

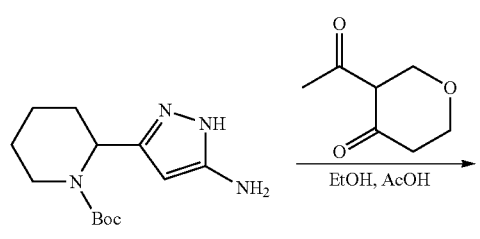

4

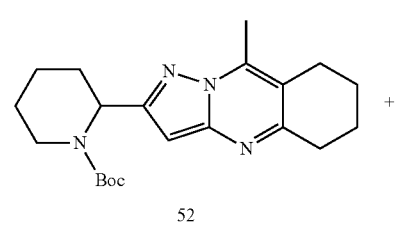

52

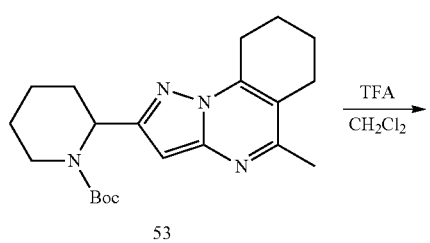

53

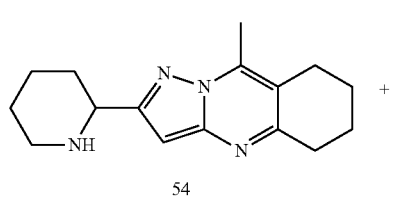

54

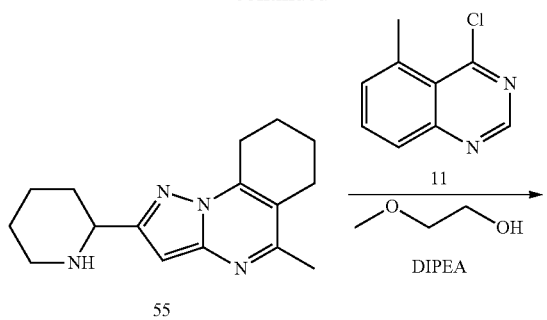

55

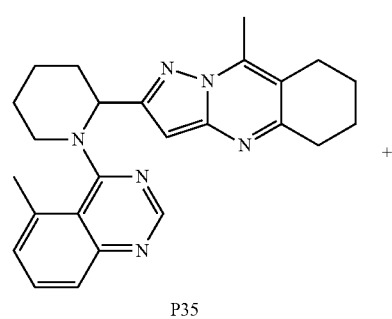

P35

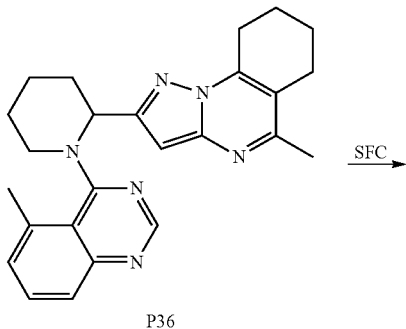

P36

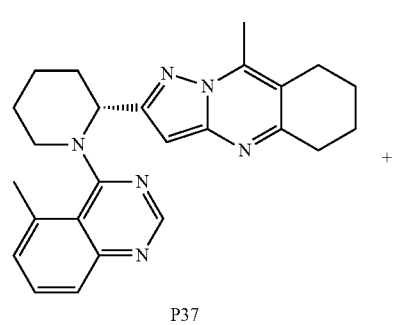

P37

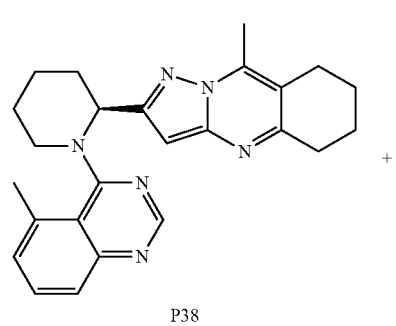

P38

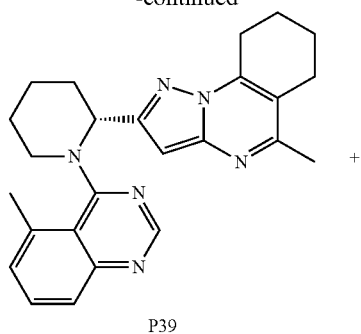

P39

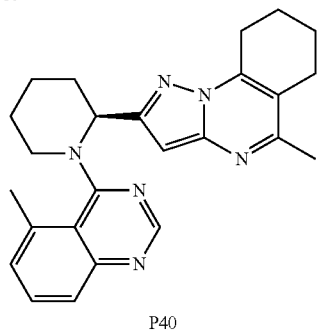

P40

Step 1: Synthesis of tert-butyl 2-(9-methyl-5,6,7,8-tetrahydropyrazolo[5,1-b]quinazolin-2-yl)-piperidine-1-carboxylate 52 and tert-butyl 2-(5-methyl-6,7,8,9-tetrahydropyrazolo[1,5-a]-quinazolin-2-yl) piperidine-1-carboxylate 53

To a solution of intermediate 4 (1.5 g, 5.6 mmol) in ethanol (100 mL), 2-acetylcyclohexanone (0.85 ml, 6.73 mmol, 1.2 eq.) and acetic acid (3.2 ml, 10 eq.) were added. The resulting mixture was stirred for 4 hours at reflux. The solution was then concentrated in vacuo and triturated in di-isopropyl ether. The solid was filtered off and dried into the oven to give the mixture of intermediate 52 and intermediate 53 (2 g, 96%).

LCMS m/z=371 (M+H)

Step 2: Synthesis of 9-methyl-2-(piperidin-2-yl)-5,6,7,8-tetrahydropyrazolo[5,1-b]quinazoline 54 and 5-methyl-2-(piperidin-2-yl)-6,7,8,9-tetrahydropyrazolo[1,5-a]quinazoline 55

To a solution of the mixture of intermediate 52 and intermediate 53 (2 g, 5.4 mmol) in dichloromethane (100 ml), TFA (2.6 ml, 27 mmol, 10 eq.) was added at room temperature under inert atmosphere. The resulting mixture was stirred for night at room temperature. The solution was then adjusted to pH=7 with saturated Na$_2$CO$_3$ solution. The combined organics were collected, dried with anhydrous MgSO4, filtered off and concentrated in vacuo to yield the mixture of intermediate 54 and intermediate 55 (1900 mg) which was used as such into the next step.

LCMS m/z=271 (M+H)

Step 3: Synthesis of 9-methyl-2-(1-(5-methylquinazolin-4-yl)piperidin-2-yl)-5,6,7,8-tetrahydropyrazolo[5,1-b]quinazoline P35 and 5-methyl-2-(1-(5-methylquinazolin-4-yl)piperidin-2-yl)-6,7,8,9-tetrahydropyrazolo[1,5-a]quinazoline P36

To a solution of the mixture of intermediate 54 and intermediate 55 (1800 mg, 3.32 mmol) in 2-methoxy ethanol (40 ml), DIPEA (0.86 ml, 5 mmol, 3 eq.) and 4-chloro-5-methyl-quinazoline 11 (100 mg, 0.5 mmol, 1.3 eq.) were added at room temperature. The resulting mixture was stirred at 50° C. for 24 hours. After concentration in vacuo the crude (1.4 g, 50% pure, the ratio of P35/P36 is 60/40) was purified by HPLC to give the mixture of compound P35 and compound P36 as a racemic mixture which was further purified by SFC to get the enantiomerically pure compounds P37 (120 mg, 20%), P38 (122 mg, 21%), P39 (80 mg, 15%) and P40 (83 mg, 16%).

LCMS m/z=413 (M+H)$^+$

P35: $^1$H NMR (400 MHz, DMSO-d$_6$) δ ppm 1.50 (br. s., 1H), 1.58-1.72 (m, 2H), 1.73-1.90 (m, 6H), 2.12-2.35 (m, 2H), 2.53 (s, 3H), 2.62 (br. s., 4H), 2.71 (br. s., 2H), 2.79 (br. s., 2H), 2.86 (s, 3H), 5.67 (br. s., 1H), 6.11 (br. s., 1H), 6.01-6.19 (m, 1H), 7.19-7.34 (m, 1H), 7.47-7.62 (m, 2H), 8.46 (s, 1H)

P36: $^1$H NMR (400 MHz, DMSO-d$_6$) δ ppm 1.51 (d, J=6.5 Hz, 1H), 1.58-1.71 (m, 2H), 1.75-1.92 (m, 6H), 2.16-2.34 (m, 2H), 2.38 (s, 3H), 2.56-2.69 (m, 7H), 2.86 (s, 3H), 3.44-3.59 (m, 2H), 5.68 (br. s., 1H), 6.13 (br. s., 1H), 7.23-7.33 (m, 1H), 7.52-7.63 (m, 2H), 8.46 (s, 1H)

Synthesis of N-(5-methyl-4-(2-(8-morpholino-6,7-dihydro-5H-cyclopenta[d]pyrazolo-[1,5-a]pyrimidin-2-yl)piperidin-1-yl)quinazolin-2-yl)methanesulfonamide P41

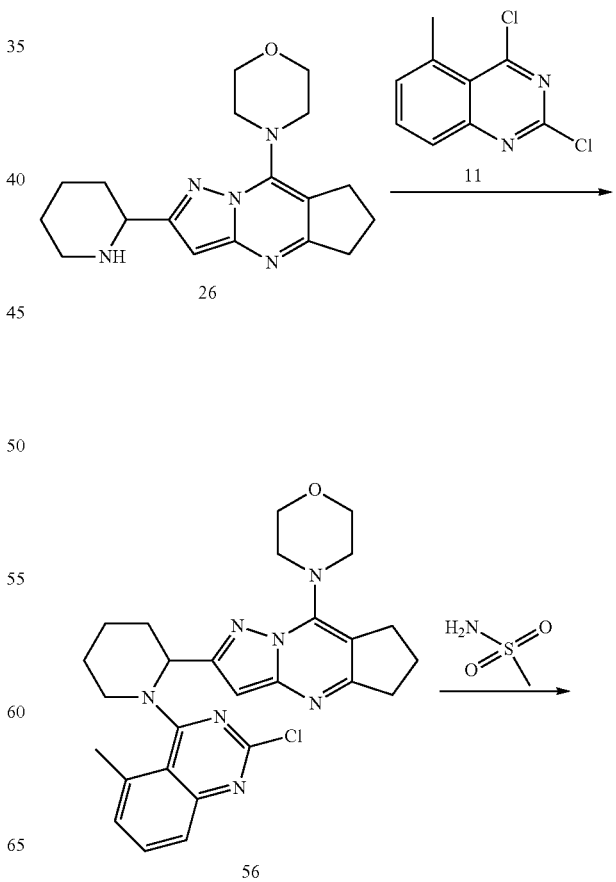

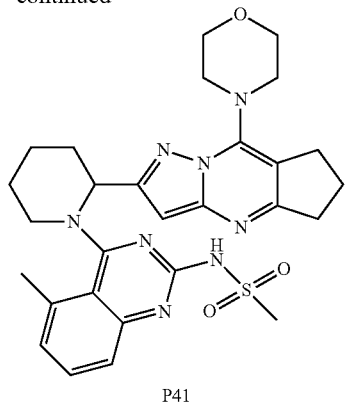

P41

Step 1: Synthesis of 4-(2-(1-(2-chloro-5-methylqui-nazolin-4-yl)piperidin-2-yl)-6,7-dihydro-5H-cyclopenta[d]pyrazolo[1,5-a]pyrimidin-8-yl)morpholine 56

Intermediate 26 (500 mg, 1.37 mmol) was dissolved in 2-methoxyethanol (25 mL). Then 2,4-dichloro-5-methylquinazoline 11 (1.46 g, 3.43 mmol, 2.5 eq.) and DIPEA (0.71 mL, 4.12 mmol, 3 eq.) were added. The reaction mixture was stirred at 50° C. during 16 hours then evaporated under reduce pressure. The crude was dissolved in DCM, washed two times with a saturated solution of sodium carbonate. The combined organic layers were dried over magnesium sulfate, filtered and concentrated in vacuo. The residue was purified by reverse phase HPLC to give intermediate 56 (160 mg, 23%).

LCMS (M+1)=505.

Step 2: N-(5-methyl-4-(2-(8-morpholino-6,7-dihydro-5H-cyclopenta[d]pyrazolo[1,5-a]-pyrimidin-2-yl)piperidin-1-yl)quinazolin-2-yl)methanesulfonamide P41

Intermediate 56 (150 mg, 0.298 mmol) was dissolved in 1,4-dioxane (5 mL) in a sealed tube. Methane sulfonamide (56.6 mg, 0.59 mmol, 2 eq.), Cs$_2$CO$_3$ (242 mg, 0.74 mmol, 2.5 eq.), 4,5-bis(diphenylphosphino)-9,9-dimethylxanthene (51.6 mg, 0.089 mmol, 0.3 eq.) and palladium acetate (20 mg, 0.089 mmol, 0.3 eq.) were then added. The reaction mixture was heated to 110° C. in the microwave during 10 minutes. Then the mixture was filtered over decalite, rinsed with DCM. The solution was evaporated under reduce pressure. The crude was purified by reverse phase HPLC giving compound P41 (40 mg, 25%).

LCMS (M+1)=563.

$^1$H NMR (400 MHz, DMSO-d$_6$) δ ppm NMR: 1.58-1.70 (m, 1H) 1.71-1.82 (m, 2H) 1.84-1.99 (m, 1H) 2.09-2.20 (m, 2H) 2.22-2.35 (m, 1H) 2.40-2.48 (m, 1H) 2.73 (s, 3H) 2.88 (t, J=7.71 Hz, 2H) 2.99 (s, 3H) 3.12 (t, J=7.25 Hz, 2H) 3.59-3.73 (m, 5H) 3.77-3.82 (m, 4H) 3.88 (m, J=11.35 Hz, 1H) 6.00 (m, J=3.62 Hz, 1H) 6.22 (s, 1H) 7.14 (d, J=7.31 Hz, 1H) 7.31 (d, J=8.12 Hz, 1H) 7.49-7.61 (m, 1H) 9.97-11.23 (m, 1H)

Synthesis of N,N,5-trimethyl-2-(1-(5-methylquinazolin-4-yl)piperidin-2-yl)-6,7-dihydro-5H-pyrazolo[1,5-a]pyrrolo[2,3-d]pyrimidin-8-amine P42

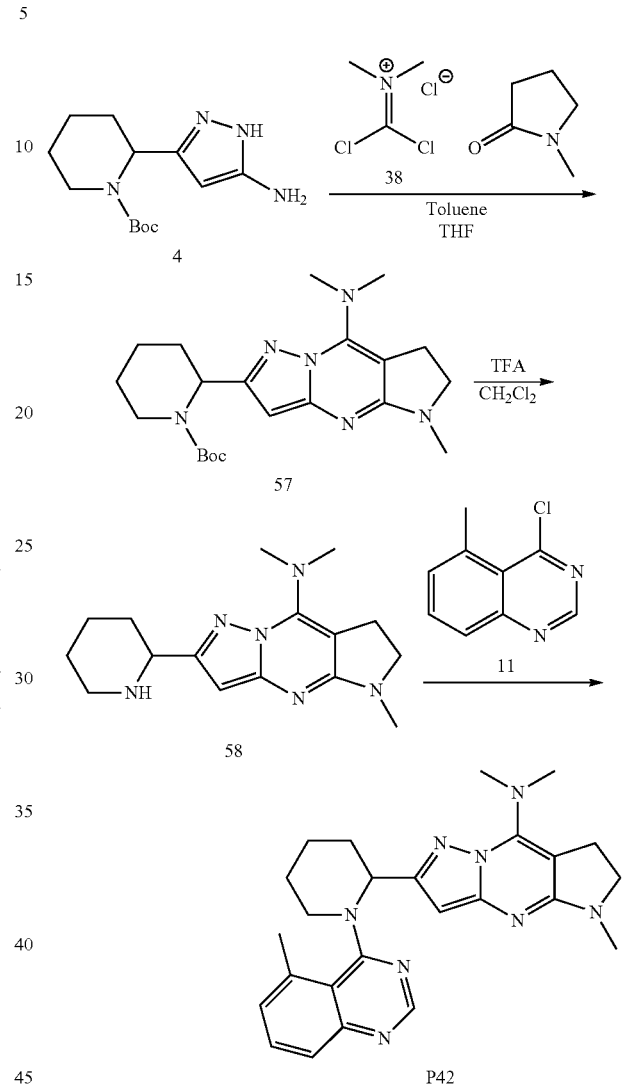

P42

Step 1: Synthesis of tert-butyl 2-(8-(dimethylamino)-5-methyl-6,7-dihydro-5H-pyrazolo-[1,5-a]pyrrolo[2,3-d]pyrimidin-2-yl)piperidine-1-carboxylate 57

A solution of (dichloromethylene)dimethylammonium chloride 38 (3.6 g, 22.5 mmol) was dissolved in toluene (75 mL) and 1-methyl-2-pyrrolidinone (1.084 mL, 11.3 mmol, 0.5 eq.) was added under inert atmosphere at room temperature. The solution was warmed to 80° C. and stirred for 1 hour until a red solution was observed. The solution was cooled to room temperature and then added dropwise into a solution of intermediate 4 (1.5 g, 5.6 mmol, 0.25 eq.) in DMF (20 mL) and the solution was stirred at room temperature for 1 hour. After concentration in vacuo the crude was extracted with EtOAc (200 mL) and washed with aqueous saturated solution of NaHCO$_3$. The aqueous phase was further extracted with dichloromethane (100 mL) and the combined organics were concentrated in vacuo and purified by column chromatography eluting with a gradient starting from 0% to 10% MeOH and DCM to give intermediate 57 (530 mg, 20%, 82% purity) which was used as such into the next step.

LCMS m/z=401 (M+H)$^+$

Step 2: Synthesis of N,N,5-trimethyl-2-(piperidin-2-yl)-6,7-dihydro-5H-pyrazolo[1,5-a]-pyrrolo[2,3-d]pyrimidin-8-amine 58

To a solution of intermediate 57 (530 mg, 1.08 mmol) in DCM (30 mL) was added TFA (0.41 mL, 5.4 mmol, 5 eq.) and the solution was stirred for 48 hours at room temperature. The solution was then concentrated in vacuo and adjusts to pH=7 with aqueous saturated solution of NaHCO$_3$. The mixture was then extracted with DCM (100 mL) and the combined organics were dried with MgSO$_4$, filtered off and concentrated in vacuo giving intermediate 58 (320 mg, 88%, 90% purity) which was used as such into the next step.

LCMS m/z=301 (M+H)$^+$

Step 3: Synthesis of N,N,5-trimethyl-2-(1-(5-methylquinazolin-4-yl)piperidin-2-yl)-6,7-dihydro-5H-pyrazolo[1,5-a]pyrrolo[2,3-d]pyrimidin-8-amine P42

To a solution of intermediate 58 (320 mg, 0.95 mmol) in 2-methoxy ethanol (50 mL), 4-chloro-5-methylquinazoline 11 (513 mg, 1.4 mmol, 1.5 eq.) was added. The resulting mixture was stirred at 50° C. After 16 hours, the solution was concentrated in vacuo and diluted with DCM (50 mL) and washed three times with Na$_2$CO$_3$ solution. The combined organics were dried over MgSO$_4$, filtered off and purified on HPLC to give compound P42 (35 mg, 9%).

LCMS m/z=443 (M+H)$^+$ $^1$H NMR (400 MHz, DMSO-d$_6$, 420 K) δ ppm 1.44-1.60 (m, 1H) 1.61-1.75 (m, 2H) 1.84-1.98 (m, 1H) 2.13-2.31 (m, 2H) 2.84 (s, 3H) 2.85 (s, 3H) 3.04 (s, 6H) 3.08-3.15 (m, 2H) 3.46-3.66 (m, 4H) 5.49-5.59 (m, 2H) 7.28-7.33 (m, 1H) 7.57-7.62 (m, 2H) 8.48 (s, 1H)

B. Pharmacological Examples

B.1 Antiviral Activity

Black 384-well clear-bottom microtiter plates (Corning, Amsterdam, The Netherlands) were filled via acoustic drop ejection using the echo liquid handler (Labcyte, Sunnyvale, Calif.). 200 nL of compound stock solutions (100% DMSO) were transferred to the assay plates. 9 serial 4-fold dilutions of compound were made, creating per quadrant the same compound concentration. The assay was initiated by adding 10 µL of culture medium to each well (RPMI medium without phenol red, 10% FBS-heat inactivated, 0.04% gentamycin (50 mg/mL). All addition steps are done by using a multidrop dispenser (Thermo Scientific, Erembodegem, Belgium). Next, rgRSV224 virus (MOI=1) diluted in culture medium was added to the plates. rgRSV224 virus is an engineered virus that includes an additional GFP gene (Hallak L K, Spillmann D, Collins P L, Peeples M E. Glycosaminoglycan sulfation requirements for respiratory syncytial virus infection; Journal of virology (2000), 74(22), 10508-13) and was in-licensed from the NIH (Bethesda, Md., USA). Finally, 20 µL of a HeLa cell suspension (3,000 cells/well) were plated. Medium, virus- and mock-infected controls were included in each test. The wells contain 0.05% DMSO per volume. Cells were incubated at 37° C. in a 5% CO2 atmosphere. Three days post-virus exposure, viral replication was quantified by measuring GFP expression in the cells by an in house developed MSM laser microscope (Tibotec, Beerse, Belgium). The EC50 was defined as the 50% inhibitory concentration for GFP expression. In parallel, compounds were incubated for three days in a set of white 384-well microtiter plates (Corning) and the cytotoxicity of compounds in HeLa cells was determined by measuring the ATP content of the cells using the ATPlite kit (Perkin Elmer, Zaventem, Belgium) according to the manufacturer's instructions. The CC50 was defined as the 50% concentration for cytotoxicity.

TABLE B-1 antiviral data and selectivity index

| Compound | RSV HELA pEC$_{50}$ | TOX HELA pCC50 |
| --- | --- | --- |
| P1 | 8.75 | 4.4 |
| P2 | 7.88 | 4.3 |
| P3 | 9.25 | 4.5 |
| P4 | 6.78 | 4.7 |
| P5 | 6.56 | 4.6 |
| P6 | 5.92 | 4.8 |
| P7 | 8.22 | 4.2 |
| P8 | 6.79 | 4.5 |
| P9 | 7.87 | 4.3 |
| P10 | 6.05 | 4.6 |
| P11 | 6.17 | 4.7 |
| P12 | 7.12 | 4.4 |
| P13 | 6.14 | 4.7 |
| P14 | 7.39 | 4.3 |
| P15 | 8.75 | 4.6 |
| P16 | 6.39 | 4 |
| P17 | 7.01 | 4.6 |
| P18 | 5.41 | 4.3 |
| P19 | 7.71 | 4.3 |
| P20 | 7.64 | 4.2 |
| P21 | 6.15 | 4.6 |
| P22 | 6.55 | 4.6 |
| P23 | 7.18 | 4.6 |
| P24 | 5.02 | 4.8 |
| P25 | 6.33 | 4 |
| P26 | 8.8 | 4.4 |
| P27 | 8.69 | 4.3 |
| P28 | 6.45 | 4.6 |
| P29 | 5.43 | 4 |
| P30 | 6.55 | 4 |
| P31 | 6.02 | 4.9 |
| P32 | 7.26 | 4 |
| P33 | 6.09 | 4.4 |
| P34 | 7.68 | 4.6 |
| P35 | 6.11 | 4.6 |
| P36 | 6.01 | 4.6 |
| P37 | 5.11 | 4.4 |
| P38 | 6.79 | 4.6 |
| P39 | 5.55 | 4.9 |
| P40 | 6.7 | 4.7 |
| P41 | 6.64 | 4 |
| P42 | 7.78 | 4.6 |

C. Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

| C.1. Tablets | |
|---|---|
| Active ingredient | 5 to 50 mg |
| Di calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

C.2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

C.3. Injectable

A parenteral composition is prepared by stirring 1.5% by weight of active ingredient of the invention in 10% by volume propylene glycol in water.

| C.4. Ointment | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula (I-a) or formula (I-b), wherein

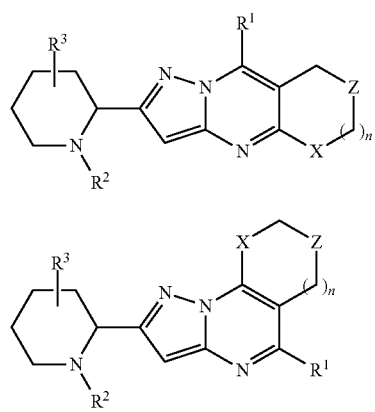

n is an integer 0, 1 or 2;
X is selected from the group consisting of: $CH_2$, O, $CH_2O$ and $NR^4$, wherein $R^4$ is hydrogen, $C_{1-4}$alkyl or benzyl;
Z is selected from the group consisting of: $CH_2$, O and $NR^4$, wherein $R^4$ is hydrogen, $C_{1-4}$alkyl or benzyl;
and at least one of X or Z is $CH_2$;
$R^1$ is selected from the group consisting of: hydrogen, hydroxy, $C_{1-4}$alkyl, amino, mono- or di($C_{1-4}$alkyl) amino, and Heterocyclyl$^1$;
Heterocyclyl$^1$ is selected from the group consisting of: azetidinyl, pyrrolidinyl, piperidinyl, piperazinyl, or morpholinyl; wherein each azetidinyl, pyrrolidinyl, piperidinyl, piperazinyl, or morpholinyl is optionally substituted with one or two substituents each independently selected from the group consisting of: $C_{1-4}$alkyl, hydroxy, halo, trifluoromethyl, $C_{1-4}$alkyloxycarbonyl, amino, $C_{1-4}$alkylaminocarbonyl, and $C_{1-4}$alkylsulfonyl;
$R^2$ is phenyl-(CO)—, wherein the phenyl is substituted with one or two substituents each independently selected from the group consisting of: hydrogen, halo, trifluoromethyl, $C_{1-4}$alkyl, $C_{1-4}$alkyloxy, and $C_{1-4}$alkylsulfonylamino;
or $R^2$ is a bicyclic heterocycle selected from cinnolinyl, quinazolinyl, or quinoxalinyl, wherein said cinnolinyl, quinazolinyl, or quinoxalinyl is substituted with one or two substituents each independently selected from the group consisting of: hydrogen, halo, trifluoromethyl, $C_{1-4}$alkyl, $C_{1-4}$alkyloxy, and $C_{1-4}$alkylsulfonylamino; and
$R^3$ is selected from the group consisting of: hydrogen, $C_{1-6}$alkyl, hydroxy, and halo;
and a pharmaceutically acceptable salt thereof.

2. The compound as claimed in claim 1 wherein
n is an integer 0, 1 or 2;
X is $CH_2$, O, $CH_2O$ or $NR^4$, wherein $R^4$ is $C_{1-4}$alkyl;
Z is $CH_2$, O or $NR^4$, wherein $R^4$ is $C_{1-4}$alkyl;
and at least one of X or Z is $CH_2$;
$R^1$ is hydrogen, hydroxy, $C_{1-4}$alkyl, amino, mono- or di($C_{1-4}$alkyl)amino, or Heterocyclyl$^1$;
Heterocyclyl$^1$ is pyrrolidinyl, or morpholinyl;
$R^2$ is phenyl-(CO)— wherein the phenyl is substituted with one or two substituents each independently selected from hydrogen, $C_{1-4}$alkyl, or $C_{1-4}$alkylsulfonylamino;
or $R^2$ is a bicyclic heterocycle selected from cinnolinyl, quinazolinyl, or quinoxalinyl, wherein said bicyclic heterocycle is substituted with one or two substituents each independently selected from hydrogen, halo, trifluoromethyl, $C_{1-4}$alkyloxy, and $C_{1-4}$alkylsulfonylamino; and
$R^3$ is hydrogen;
or a pharmaceutically acceptable salt thereof.

3. The compound as claimed in claim 1 wherein the compound is of formula (I-a) wherein $R^1$ is Heterocyclyl$^1$; n is 0; X is $CH_2$; and Z is $CH_2$.

4. The compound as claimed in claim 1 wherein the compound is of formula (I-a) wherein $R^1$ is Heterocyclyl$^1$; n is 1; X is $CH_2$; and Z is $CH_2$.

5. The compound as claimed in claim 1 wherein the compound is of formula (I-a) wherein $R^1$ is Heterocyclyl$^1$; n is 2; X is $CH_2$; and Z is $CH_2$.

6. The compound as claimed in claim 1 wherein the compound is of formula (I-a) wherein $R^1$ is Heterocyclyl$^1$; n is 0; X is $CH_2$; and Z is O.

7. The compound as claimed in claim 1 wherein the compound is of formula (I-a) wherein $R^1$ is Heterocyclyl$^1$; n is 1; X is $CH_2$; and Z is O.

8. The compound as claimed in claim 1 wherein the compound is of formula (I-a) wherein $R^1$ is Heterocyclyl$^1$; n is 2; X is $CH_2$; and Z is O.

9. The compound as claimed in claim 1 wherein the compound is of formula (I-a) wherein $R^1$ is di($C_{1-4}$alkyl)amino; n is 1; X is $NR^4$; $R^4$ is $C_{1-4}$alkyl; and Z is $CH_2$.

10. The compound as claimed in claim 1 wherein the compound is of formula (I-a) wherein $R^1$ is $C_{1-4}$alkyl; n is 1; X is $CH_2$; and Z is $CH_2$.

11. The compound as claimed in claim 1 wherein the compound is of formula (I-b) wherein $R^1$ is $C_{1-4}$alkyl; n is 1; X is $CH_2$; and Z is $CH_2$.

12. A pharmaceutical composition comprising a pharmaceutically acceptable carrier and a therapeutically active amount of a compound as claimed in claim 1 or a pharmaceutically acceptable salt thereof.

13. A process for preparing a pharmaceutical composition as claimed in claim 12 wherein a therapeutically active amount of a compound as claimed in claim 1, or a pharmaceutically acceptable salt thereof, is mixed with a pharmaceutically acceptable carrier.

14. A method of treating a respiratory syncytial virus infection in a patient comprising administering the compound as claimed in claim 1 or a pharmaceutically acceptable salt thereof to said patient.

15. A compound selected from the group consisting of:
- N-(4-methyl-2-(2-(9-morpholino-5,6,7,8-tetrahydropyrazolo[5,1-b]quinazolin-2-yl)piperidine-1-carbonyl)phenyl)methanesulfonamide;
- (R)—N-(4-methyl-2-(2-(9-morpholino-5,6,7,8-tetrahydropyrazolo[5,1-b]quinazolin-2-yl)-piperidine-1-carbonyl)phenyl)methanesulfonamide;
- (S)—N-(4-methyl-2-(2-(9 morpholino-5,6,7,8-tetrahydropyrazolo[5,1-b]quinazolin-2-yl)piperidine-1-carbonyl)phenyl)methanesulfonamide;
- 4-(2-(1-(6-methylquinazolin-4-yl)piperidin-2-yl)-5,6,7,8-tetrahydropyrazolo [5,1-b]quinazolin-9-yl)morpholine;
- 4-(2-(1-(5-methylquinazolin-4-yl)piperidin-2-yl)-5,6,7,8-tetrahydropyrazolo[5,1-b]quinazolin-9-yl)morpholine;
- 4-(2-(1-(2-chloro-5-methylquinazolin-4-yl)piperidin-2-yl)-5,6,7,8-tetrahydropyrazolo[5,1-b]quinazolin-9-yl)morpholine;
- N-(5-methyl-4-(2-(9-morpholino-5,6,7,8-tetrahydropyrazolo[5, 1 b]¬quinazolin-2-yl)piperidin-1-yl)quinazolin-2-yl)methanesulfonamide;
- 4-(2-(1-(2-chloro-6-methylquinazolin-4-yl)piperidin-2-yl)-5,6,7,8-tetrahydropyrazolo[5,1-b]quinazolin-9-yl)morpholine;
- N-(6-methyl-4-(2-(9-morpholino-5,6,7,8-tetrahydropyrazolo[5, 1 b]¬quinazolin-2-yl)piperidin-1-yl)quinazolin-2-yl)methanesulfonamide;
- 4-(2-(1-(5-fluoroquinazolin-4-yl)piperidin-2-yl)-5,6,7,8-tetrahydropyrazolo¬[5,1-n]-quinazolin-9-yl)morpholine;
- 4-(2-(1-(5-(trifluoromethyl)quinazolin-4-yl)piperidin-2-yl)-5,6,7,8-tetrahydropyrazolo[5,1-b]quinazolin-9-yl)morpholine;
- 4-(2-(1-(5-methoxyquinazolin-4-yl)piperidin-2-yl)-5,6,7,8-tetrahydro¬pyrazolo[5,1-b]quinazolin-9-yl)morpholine;
- 4-(2-(1-(6-ethyl-5-methylquinazolin-4-yl)piperidin-2-yl)-5,6,7,8-tetrahydro¬pyrazolo[5,1-b]quinazolin-9-yl)morpholine;
- N-(2-(2-(9-hydroxy-5,6,7,8-tetrahydropyrazolo[5,1-b]quinazolin-2 yl)¬piperidine-1-carbonyl)-4-methylphenyl)methanesulfonamide;
- N-(2-(2-(9-(dimethylamino)-5,6,7,8-tetrahydropyrazolo [5,1-b]quinazolin-2 yl)piperidine-1-carbonyl)-4-methylphenyl)methanesulfonamide;
- N,N-dimethyl-2-(1-(5-methylquinazolin-4-yl)piperidin-2-yl)-5,6,7,8-tetra-hydropyrazolo[5,1-b]quinazolin-9-amine;
- N-(4-methyl-2-(2-(5,6,7,8-tetrahydropyrazolo[5,1-b]quinazolin-2-yl)¬piperidine-1-carbonyl)phenyl)methanesulfonamide;
- 2-(1-(5-methylquinazolin-4-yl)piperidin-2-yl)-5,6,7,8-tetrahydropyrazolo¬[5,1-b]quinazoline;
- N-(2-(2-(9-amino-5,6,7,8-tetrahydropyrazolo[5,1-b]quinazolin-2-yl)¬piperidine-1-carbonyl)-4-methylphenyl)methanesulfonamide;
- N-(4-methyl-2-(2-(8-morpholino-6,7-dihydro-5H-cyclopenta[d]pyrazolo¬[1,5 a]pyrimidin-2-yl)piperidine-1-carbonyl)phenyl)methanesulfonamide;
- 4-(2-(1-(5-methylquinazolin-4-yl)piperidin-2-yl)-6,7-dihydro-5H-cyclo-penta[d]pyrazolo[1,5-a]pyrimidin-8-yl)morpholine;
- 2-(1-(5-methylquinazolin-4-yl)piperidin-2-yl)-8-(pyrrolidin-1-yl)-6,7 dihydro-5H-cyclopenta[d]pyrazolo[1,5-a]pyrimidine;
- N-(4-methyl-2-(2-(10-morpholino-6,7,8,9-tetrahydro-5H cyclohepta¬[d]¬pyrazolo[1,5-a]pyrimidin-2-yl)piperidine-1-carbonyl)phenyl)-methanesulfonamide;
- 4-(2-(1-(5-methylquinazolin-4-yl)piperidin-2-yl)-6,7,8,9-tetrahydro-5H cyclohepta[d]pyrazolo[1,5-a]pyrimidin-10-yl)morpholine;
- N-(4-methyl-2-(2-(8-morpholino-5,7-dihydrofuro[3,4-d]pyrazolo[1,5 a]¬pyrimidin-2-yl)piperidine-1-carbonyl)phenyl)methanesulfonamide;
- N-(2-(2-(9-(dimethylamino)-5-methyl-5,6,7,8-tetrahydropyrazolo¬[1,5 a]pyrido[2,3-d]pyrimidin-2-yl)piperidine-1-carbonyl)-4-methylphenyl)-methane¬sulfonamide;
- N-(2-(2-(5-(dimethylamino)-9-methyl-6,7,8,9-tetrahydro¬pyrazolo¬[1,5-a]pyrido[3,2-e]pyrimidin-2-yl)piperidine-1-carbonyl)-4 methylphenyl)methane¬sulfonamide;
- N-(4-methyl-2-(2-(9-morpholino-7,8-dihydro-5H-pyrano[3,4-d]pyrazolo¬[1,5 a]pyrimidin-2-yl)piperidine-1-carbonyl)phenyl)methane-sulfonamide;
- 2-(1-(5-methylquinazolin-4-yl)piperidin-2-yl)-9-morpholino-7,8-dihydro-5H-pyrano[3,4-d]pyrazolo[1,5-a]pyrimidine;
- 2-(1-(5-methylquinazolin-4-yl)piperidin-2-yl)-9-morpholino-6,8-dihydro-5H-pyrano[4,3-d]pyrazolo[1,5-a]pyrimidine;
- 2-(1-(2-chloro-5-methylquinazolin-4-yl)piperidin-2-yl)-9-morpholino-6,8-dihydro-5H-pyrano[4,3-d]pyrazolo[1,5-a]pyrimidine;
- N-(5-methyl-4-(2-(9-morpholino-6,8-dihydro-5H-pyrano[4,3-d]pyrazolo¬[1,5 a]pyrimidin-2-yl)piperidin-1-yl)quinazolin-2-yl)methanesulfonamide;
- 2-(1-(2-ethoxy-5-methylquinazolin-4-yl)piperidin-2-yl)-9-morpholino-6,8-dihydro-5H-pyrano[4,3-d]pyrazolo[1,5-a]pyrimidine;
- N-(4-methyl-2-(2-(9-morpholino-6,8-dihydro-5H-pyrano[4,3-d]pyrazolo¬[1,5 a]pyrimidin-2-yl)piperidine-1-carbonyl)phenyl)methanesulfonamide;
- 9-methyl-2-(1-(5-methylquinazolin-4-yl)piperidin-2-yl)-5,6,7,8-tetrahydro¬pyrazolo[5,1-b]quinazoline;
- 5-methyl-2-(1-(5-methylquinazolin-4-yl)piperidin-2 yl)-6,7,8,9-tetrahydropyrazolo[1,5-a]quinazoline;
- (S)-9-methyl-2-(1-(5-methylquinazolin-4-yl)piperidin-2-yl)-5,6,7,8-tetrahydropyrazolo[5,1-b]quinazoline;
- (R)-9-methyl-2-(1-(5-methylquinazolin-4-yl)piperidin-2-yl)-5,6,7,8-tetrahydropyrazolo[5,1-b]quinazoline;

(S)-5-methyl-2-(1-(5-methylquinazolin-4-yl)piperidin-2-yl)-6,7,8,9-tetrahydropyrazolo[1,5-a]quinazoline;

(R)-5-methyl-2-(1-(5-methylquinazolin-4-yl)piperidin-2-yl)-6,7,8,9-tetrahydropyrazolo[1,5-a]quinazoline;

N-(5-methyl-4-(2-(8-morpholino-6,7-dihydro-5H-cyclopenta[d]pyrazolo-[1,5a]pyrimidin-2-yl)piperidin-1-yl)quinazolin-2-yl)methanesulfonamide; and N,N,5-trimethyl-2-(1-(5-methylquinazolin-4-yl)piperidin-2-yl)-6,7-dihydro-5H-pyrazolo[1,5-a]pyrrolo[2,3-d]pyrimidin-8-amine;

and pharmaceutically acceptable salts thereof.

16. A pharmaceutical composition comprising (a) a therapeutically active amount of at least one compound of claim 15 or a pharmaceutically acceptable salt thereof; and (b) at least one pharmaceutically acceptable carrier.

17. A method of treatment of a subject suffering from a respiratory syncytial virus infection, comprising administering to the subject a therapeutically active amount of a compound as claimed in claim 15 or a pharmaceutically acceptable salt thereof.

* * * * *